US012807624B2

(12) United States Patent
Xie et al.

(10) Patent No.: US 12,807,624 B2
(45) Date of Patent: Nov. 24, 2026

(54) FUSED RING COMPOUND ACTING AS SHP2 INHIBITOR

(71) Applicant: WIGEN BIOMEDICINE TECHNOLOGY (SHANGHAI) CO., LTD., Shanghai (CN)

(72) Inventors: Yuli Xie, Shanghai (CN); Yingming Wu, Shanghai (CN); Lihui Qian, Shanghai (CN)

(73) Assignee: WIGEN BIOMEDICINE TECHNOLOGY (SHANGHAI) CO., LTD., Shanghai (CN)

(*) Notice: Subject to any disclaimer, the term of this patent is extended or adjusted under 35 U.S.C. 154(b) by 335 days.

(21) Appl. No.: 18/700,689

(22) PCT Filed: Sep. 29, 2022

(86) PCT No.: PCT/CN2022/122714
§ 371 (c)(1),
(2) Date: Apr. 11, 2024

(87) PCT Pub. No.: WO2023/051717
PCT Pub. Date: Apr. 6, 2023

(65) Prior Publication Data

US 2025/0059206 A1 Feb. 20, 2025

(30) Foreign Application Priority Data

Sep. 29, 2021 (CN) .......................... 202111150390.7

(51) Int. Cl.
*C07D 519/00* (2006.01)
*A61K 31/4985* (2006.01)
*A61P 35/00* (2006.01)

(52) U.S. Cl.
CPC ........ *C07D 519/00* (2013.01); *A61K 31/4985* (2013.01); *A61P 35/00* (2018.01)

(58) Field of Classification Search
None
See application file for complete search history.

(56) References Cited

FOREIGN PATENT DOCUMENTS

| | | | |
|---|---|---|---|
| CN | 111704611 | A | 9/2020 |
| CN | 112839935 | A | 5/2021 |
| WO | 2018081091 | A1 | 5/2018 |
| WO | 2018218133 | A1 | 11/2018 |
| WO | 2019183364 | A1 | 9/2019 |
| WO | 2019183367 | A1 | 9/2019 |

*Primary Examiner* — Samantha L Shterengarts
(74) *Attorney, Agent, or Firm* — SZDC Law P.C.

(57) ABSTRACT

Disclosed are fused cyclic compounds as SHP2 inhibitors. Specifically, the present invention relates to a compound of general formula (1), a method for preparing same, and use of the compound of general formula (1) and isomers, crystalline forms, pharmaceutically acceptable salts, hydrates or solvates thereof as SHP2 inhibitors. The compounds and the isomers, the crystalline forms, the pharmaceutically acceptable salts, the hydrates or the solvates thereof of the present invention can be used for preparing a medicament for treating or preventing a disease related to SHP2 protein.

(1)

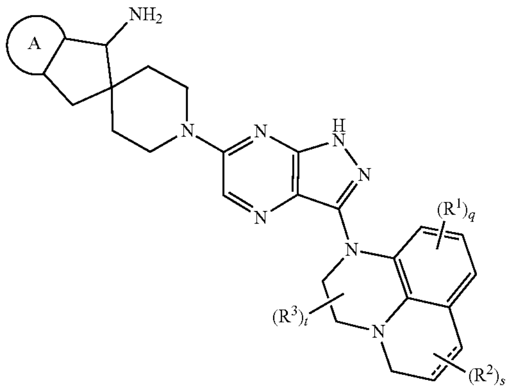

12 Claims, No Drawings

FUSED RING COMPOUND ACTING AS SHP2 INHIBITOR

The present application is the National Stage Application of PCT/CN2022/122714, filed on Sep. 29, 2022, which claims priority to Chinese Patent Application No. 202111150390.7 filed on Sep. 29, 2021, which is incorporated herein by reference in its entirety.

TECHNICAL FIELD

The present invention relates to the field of pharmaceutical chemistry, and particularly relates to a class of fused cyclic compounds with an inhibitory effect on SHP2 protein, a preparation method therefor, and use of the compounds in the preparation of a medicament for treating or preventing a related disease mediated by SHP2.

BACKGROUND

Src homology region 2-containing protein tyrosine phosphatase 2 (SHP2) is a non-receptor protein tyrosine phosphatase encoded by a PTPN11 gene, which encodes an SHP2 protein containing an N-terminal SH2 domain (N—SH2), a C-terminal SH2 domain (C—SH2), a protein phosphatase catalytic domain (PTP) and a C-terminal tail. The two SH2 domains determine the subcellular localization and functional regulation of SHP2. In an inactivated state, the N-terminal SH2 domain blocks the binding of the PTP domain and inactivates it. When the SH2 domain binds to a specific tyrosine residue on a receptor or a receptor-associated linker protein, the PTP domain is released and autoinhibition is relieved. The activation of SHP2, e.g., stimulation with cytokines and growth factors leading to the exposure of a catalytic site, results in the enzymatic activation of SHP2.

SHP2 is widely expressed and is involved in multiple cell signaling processes. The SHP2 protein not only regulates the Ras/ERK signaling pathway, but also has been reported to regulate multiple signaling pathways such as JAK-STAT3, NF-κB, PI3K/Akt, FGFR, EGFR, RHO and NFAT, etc., thereby regulating physiological functions such as cell proliferation, differentiation, migration and apoptosis.

SHP2 has been shown to be associated with a variety of diseases, and hyperactivation of catalytic activity of SHP2 caused by germline or somatic mutations has been found in Noonan syndrome, LEOPARD syndrome, myelodysplastic syndrome, juvenile myelomonocytic leukemia, myelodysplastic syndrome, B-cell precursor acute lymphoblastic leukemia and acute myeloid leukemia. With intensive studies on PTPN11/SHP2, activating mutations in PTPN11 have also been found in solid tumors, such as lung cancer, colon cancer, melanoma, neuroblastoma and liver cancer. Therefore, activated SHP2 or up-regulated SHP2 proteins in human tumors or in other diseases become new therapeutic targets. There is therefore an urgent need to study and discover compounds with good activity targeting SHP2.

SUMMARY

The present invention provides a compound of general formula (1) or an isomer, a crystalline form, a pharmaceutically acceptable salt, a hydrate or a solvate thereof:

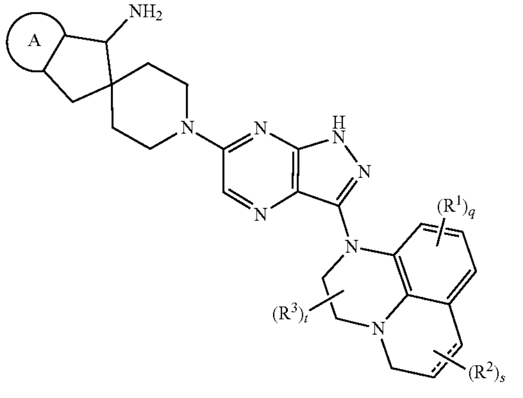

(1)

wherein in general formula (1):

each $R^1$ is independently —H, halogen, —OH, —$OR^4$, —$NR^4R^5$, —CN, —$S(O)_pR^4$, (C1-C3) alkyl, (C1-C3) haloalkyl, (C2-C4) alkenyl, (C2-C4) alkynyl or (C3-C5) cycloalkyl, wherein the (C1-C3) alkyl, (C1-C3) haloalkyl, (C2-C4) alkenyl, (C2-C4) alkynyl or (C3-C5) cycloalkyl is each independently and optionally substituted with 1, 2, 3 or 4 of the following groups: —H, halogen, —OH, —$OCH_3$ and —CN;

each $R^2$ is independently —H, halogen, —OH, —$OR^4$, —$NR^4R^5$, —CN, —$S(O)_pR^4$ or (C1-C3) alkyl, wherein the (C1-C3) alkyl is independently and optionally substituted with 1, 2, 3 or 4 of the following groups: —H, halogen, —OH, —$OCH_3$ and —CN; or two $R^2$ linked to the same carbon atom form one oxo;

each $R^3$ is independently —H, halogen, —OH, —$OR^4$, —$NR^4R^5$, —CN, —$S(O)_pR^4$ or (C1-C3) alkyl, wherein the (C1-C3) alkyl is independently and optionally substituted with 1, 2, 3 or 4 of the following groups: —H, halogen, —OH, —$OCH_3$ and —CN; or two $R^3$ linked to the same carbon atom form one oxo;

ring A is phenyl or (5-6 membered) heteroaryl, wherein the phenyl or (5-6 membered) heteroaryl is each independently and optionally substituted with 1, 2, 3 or 4 of the following groups: —H, halogen, —OH, —$OR^4$, —$NR^4R^5$, —CN, —$S(O)_pR^4$, (C1-C3) alkyl, (C1-C3) haloalkyl, (C2-C4) alkenyl, (C2-C4) alkynyl or (C3-C5) cycloalkyl, wherein the (C1-C3) alkyl, (C1-C3) haloalkyl, (C2-C4) alkenyl, (C2-C4) alkynyl or (C3-C5) cycloalkyl is each independently and optionally substituted with 1, 2, 3 or 4 of the following groups: —H, halogen, —OH, —$OCH_3$ and —CN;

$R^4$ and $R^5$ are each independently —H, (C1-C3) alkyl, (C1-C3) haloalkyl or (C3-C5) cycloalkyl, or $R^4$ and $R^5$ on the same nitrogen atom, together with the N atom to which they are linked, form (3-6 membered) heterocycloalkyl, wherein the (3-6 membered) heterocycloalkyl is optionally substituted with 1, 2, 3 or 4 of the following groups: —H, halogen, $R^6$ and —$OR^6$;

$R^6$ is —H, (C1-C3) alkyl or (C3-C5) cycloalkyl; and p is an integer of 0, 1 or 2, q is an integer of 0, 1, 2 or 3, s is an integer of 0, 1, 2, 3 or 4, and t is an integer of 0, 1, 2, 3 or 4.

In another preferred embodiment, in general formula (1), each $R^1$ is independently —H, halogen, —OH, —$OR^4$, —$NR^4R^5$, —CN, —$S(O)_pR^4$, (C1-C3) alkyl, (C1-C3) haloalkyl, (C2-C4) alkenyl, (C2-C4) alkynyl or (C3-C5) cycloalkyl, wherein the (C1-C3) alkyl, (C1-C3) haloalkyl, (C2-C4) alkenyl, (C2-C4) alkynyl or (C3-C5) cycloalkyl is each independently and optionally substituted with 1, 2, 3 or 4 of the following groups: —H, —F, —OH, —$OCH_3$ and —CN. In another preferred embodiment, in general formula (1), each $R^1$ is independently —H, —F, —OH, $OCH_3$, —$N(CH_3)_2$, —CN, —$S(O)_2CH_3$,

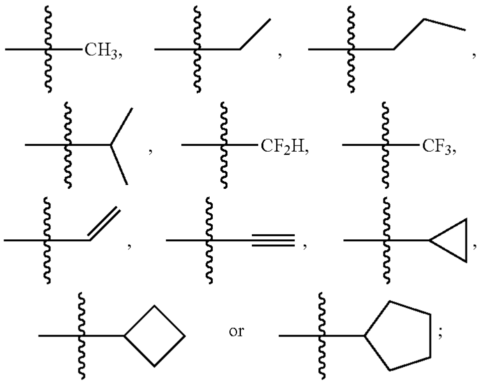

preferably, q is 1, and $R^1$ is independently —H or —F.

In another preferred embodiment, in general formula (1), each $R^2$ is independently —H, halogen, —OH, —$OR^4$, —$NR^4R^5$, —CN, —$S(O)_pR^4$ or (C1-C3) alkyl, wherein the (C1-C3) alkyl is independently and optionally substituted with 1, 2, 3 or 4 of the following groups: —H, —F, —OH, —$OCH_3$ and —CN; or two $R^2$ linked to the same carbon atom form one oxo.

In another preferred embodiment, in general formula 1), each $R^2$ is independently: —H, —F, —OH, —$OCH_3$, —$N(CH_3)_2$, —CN, —$S(O)_2CH_3$,

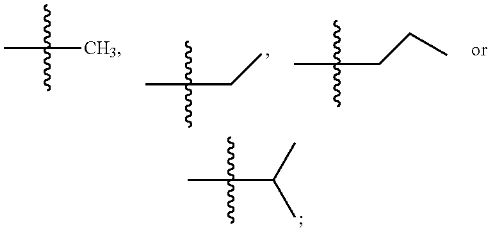

preferably, s is 2, and both $R^2$ are —H, or two $R^2$ linked to the same carbon atom form one oxo; more preferably, s is 2, and two $R^2$ linked to the same carbon atom form one oxo.

In another preferred embodiment, in general formula (1), each $R^3$ is independently —H, halogen, —OH, —$OR^4$, —$NR^4R^5$, —CN, —$S(O)_pR^4$ or (C1-C3) alkyl, wherein the (C1-C3) alkyl is independently and optionally substituted with 1, 2, 3 or 4 of the following groups: —H, —F, —OH, —$OCH_3$ and —CN; or two $R^3$ linked to the same carbon atom form one oxo.

In another preferred embodiment, in general formula (1), each $R^3$ is independently: —H, —F, —OH, —$OCH_3$, —$N(CH_3)_2$, —CN, —$S(O)_2CH_3$

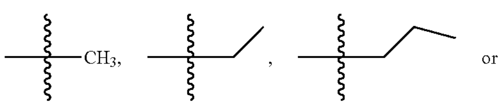

-continued

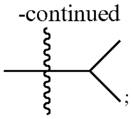

preferably, t is 1, and $R^3$ is —H; or t is 2, and two $R^3$ linked to the same carbon atom form one oxo.

In another preferred embodiment, in general formula (1), structural unit

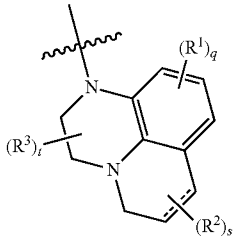

is:

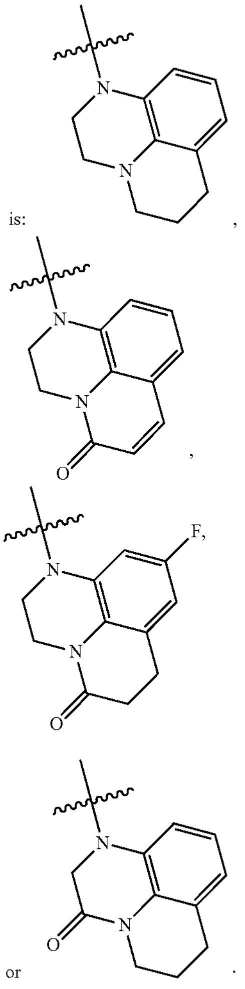

In another preferred embodiment, in general formula (1), ring A is phenyl or (5-6 membered) heteroaryl, wherein the phenyl or (5-6 membered) heteroaryl is each independently and optionally substituted with 1, 2, 3 or 4 of the following groups: —H, —F, —Cl, —OH, —$OCH_3$, —$N(CH_3)_2$, —CN, —$S(O)_2CH_3$,

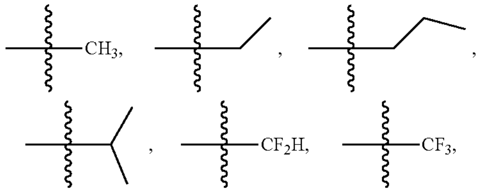

-continued
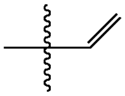, 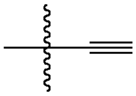, 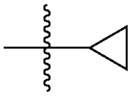,
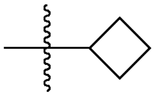 or 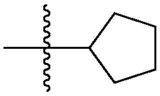;
the substituent is preferably —H, —F, —Cl, —OH, $—OCH_3$, —CN,
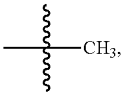, 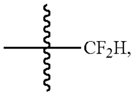, 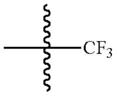 or
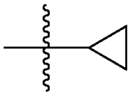;
and more preferably —H, —F, —Cl, —OH, $—OCH_3$, —CN or
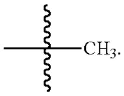.
In another preferred embodiment, in general formula (1), structural unit is:
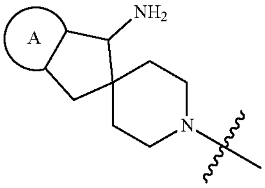
is:
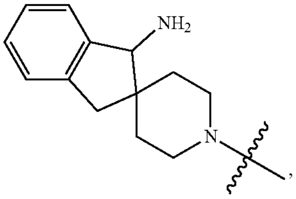
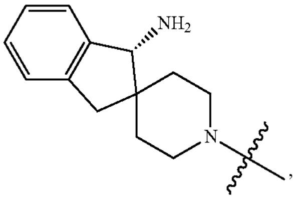
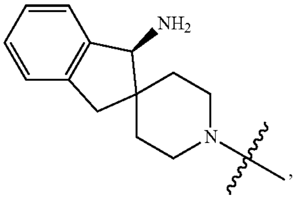
-continued
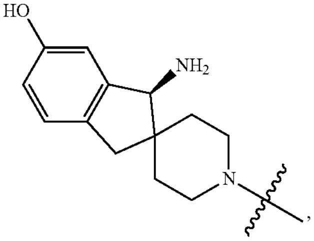
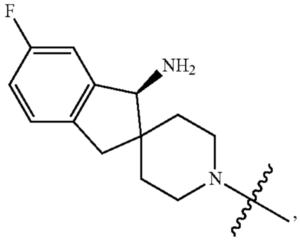
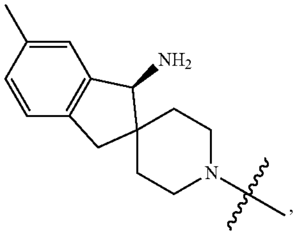
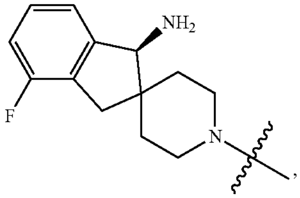
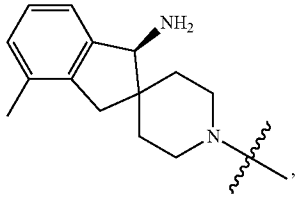
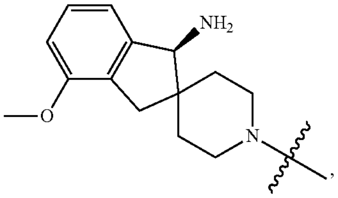
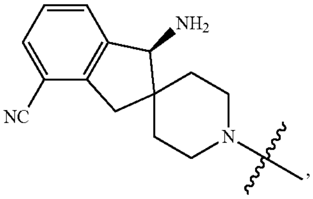
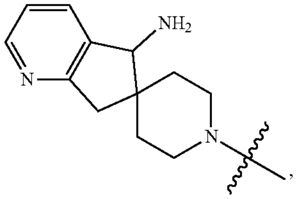

-continued
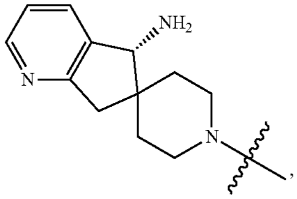,
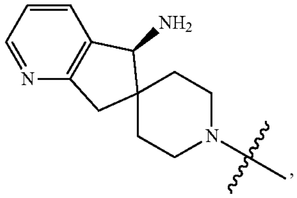,
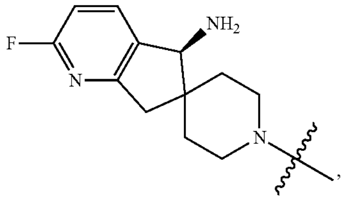,
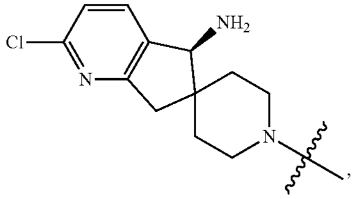,
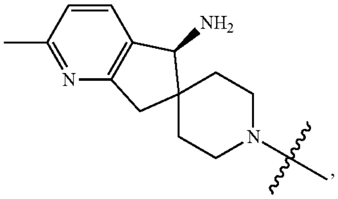,
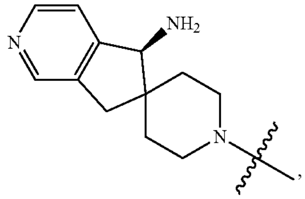,
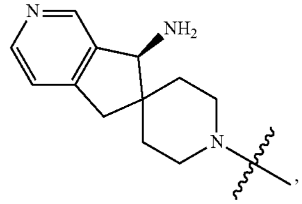,
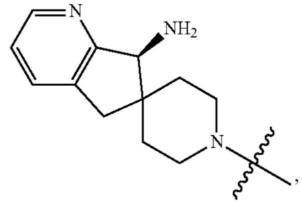,
-continued
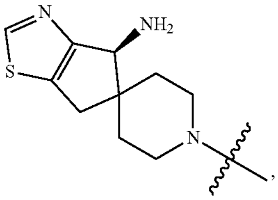, 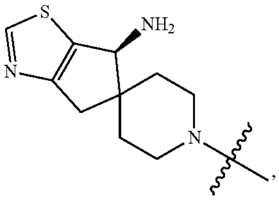,
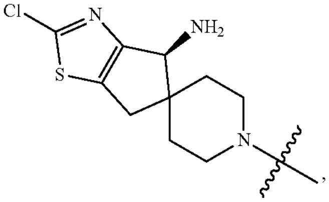,
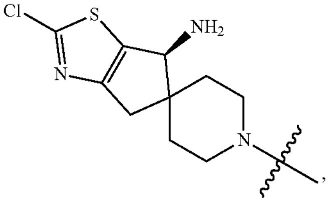,
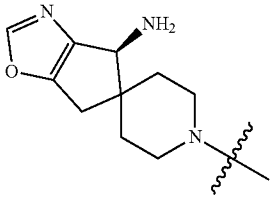 or
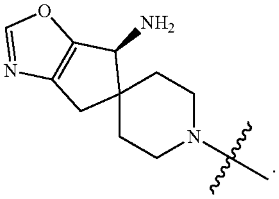.
In another preferred embodiment of the present invention, general formula (1) has a structure represented by general formula (2a), general formula (2b) and general formula (2c):
(2a)
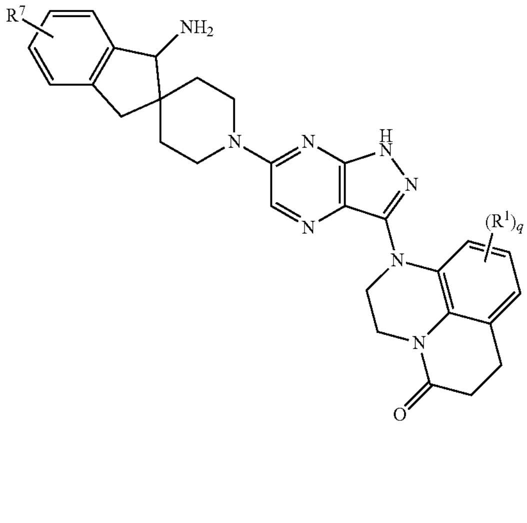

-continued
(2b)
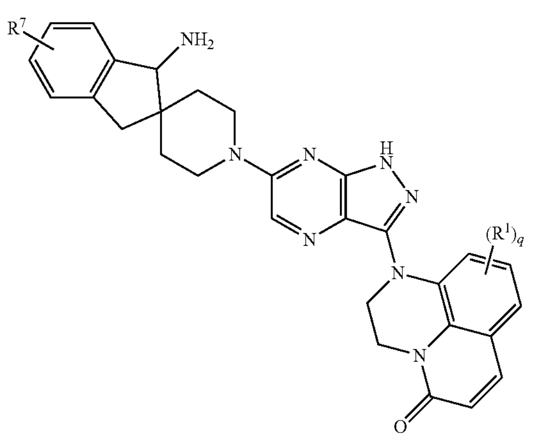
(2c)
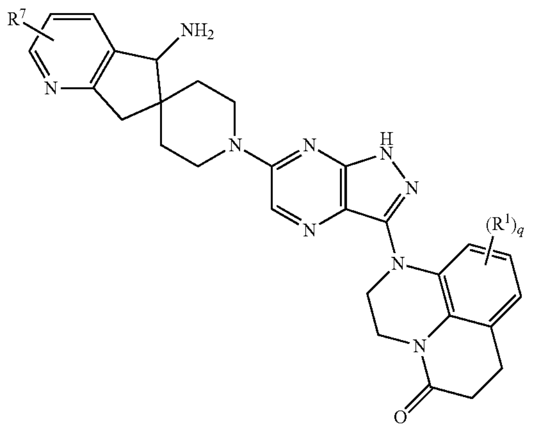
wherein $R^1$ and q are as defined above, and $R^7$ is —H, —F, —Cl, —OH, —$OCH_3$, —CN
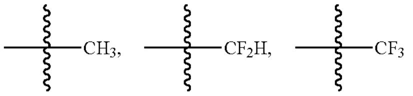
or
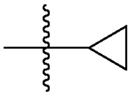
;
$R^7$ is preferably —H, —F, —Cl, —OH, —$OCH_3$, —CN or
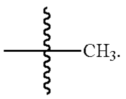
In another specific embodiment of the present invention, the compound of general formula (1) has one of the following structures:
1
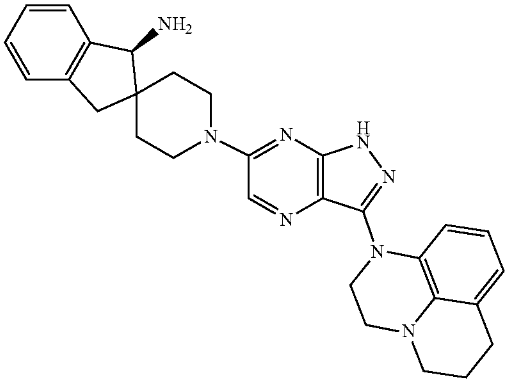
2
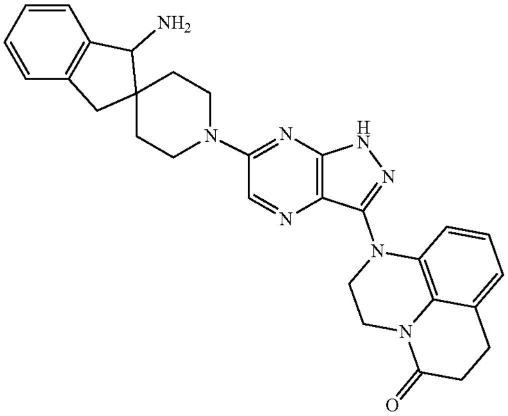
3
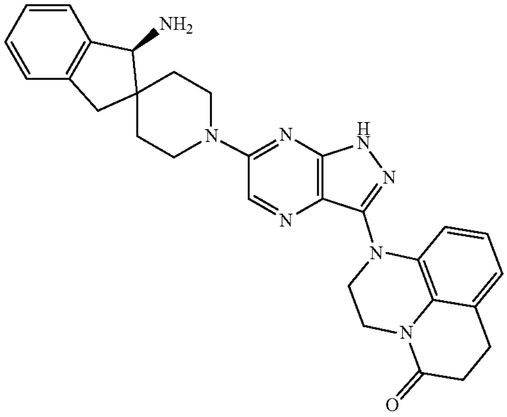
4
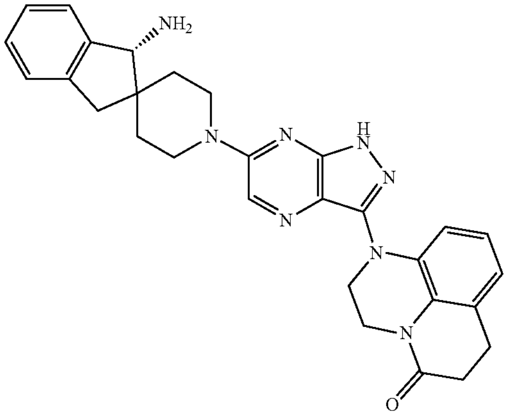

-continued
5
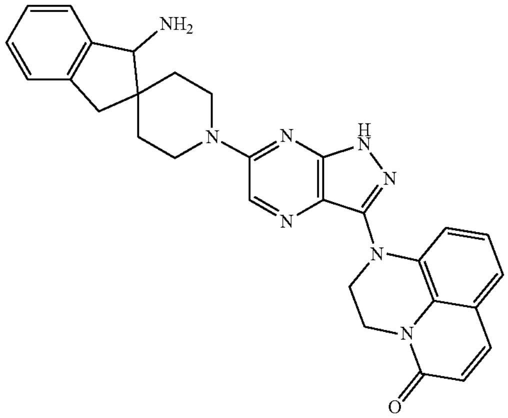
6
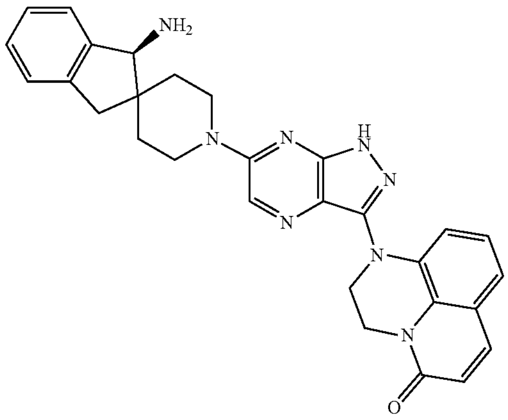
7
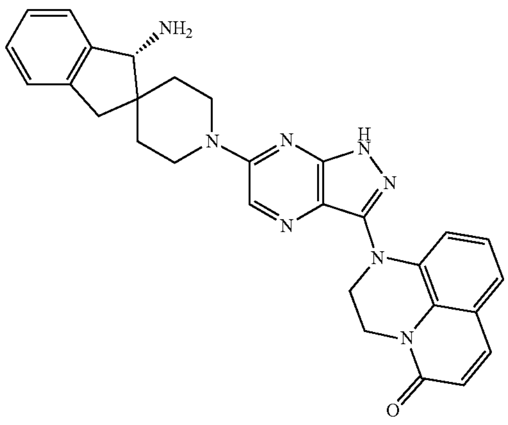
-continued
8
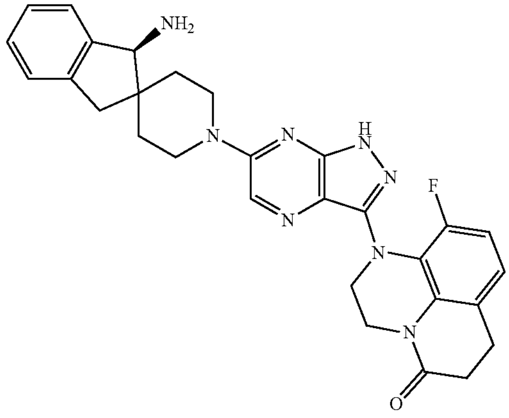
9
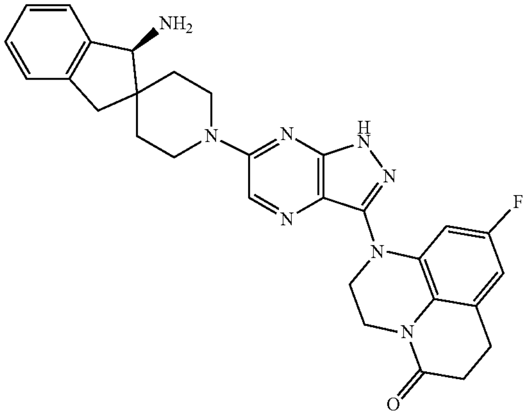
10
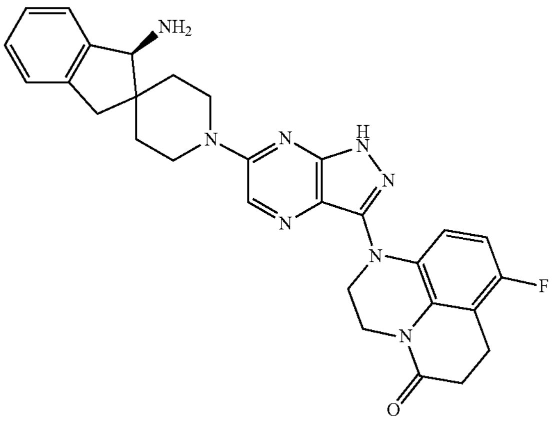

-continued
11
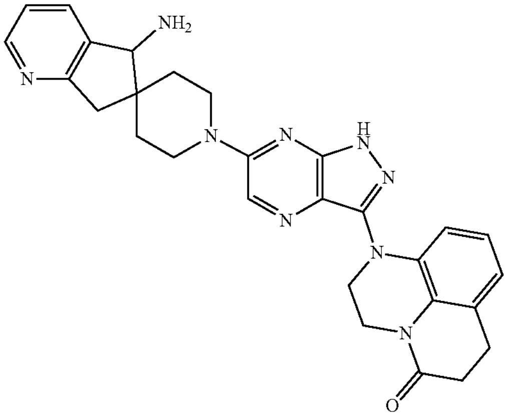
12
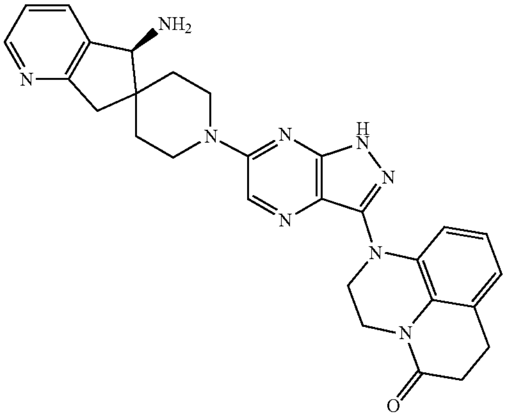
13
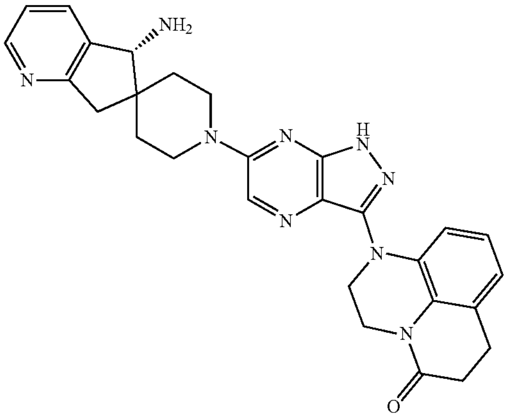
-continued
14
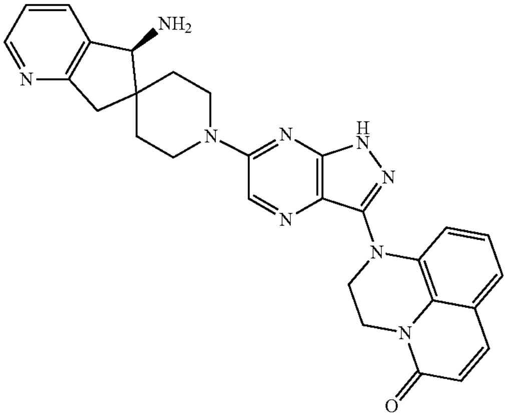
15
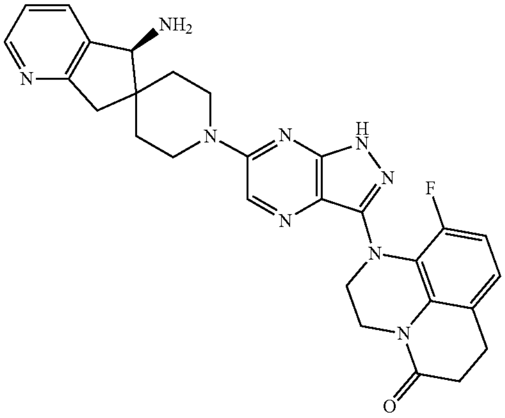
16
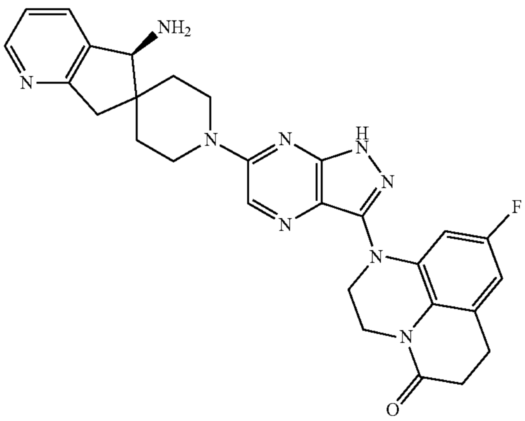

-continued
17
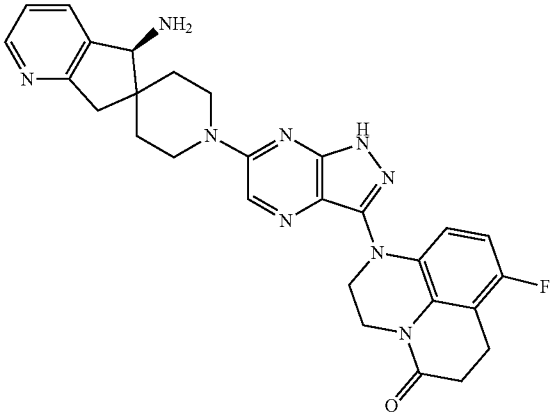
18
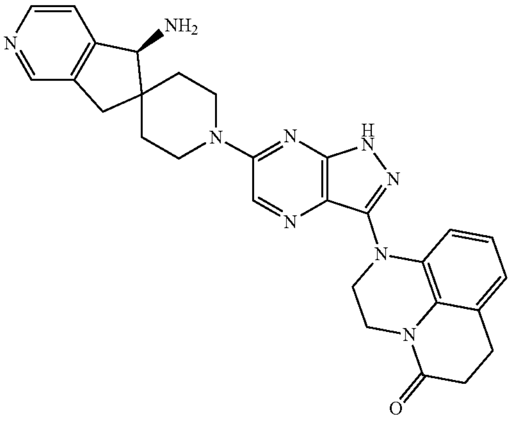
19
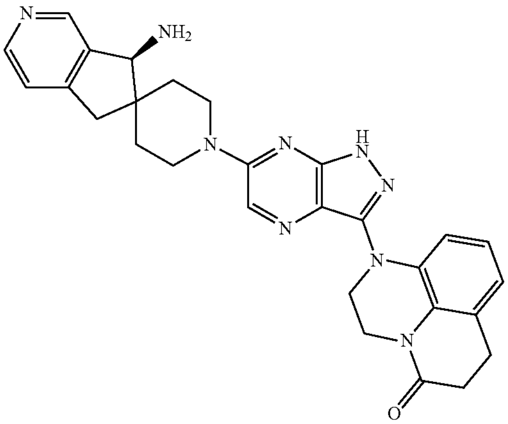
-continued
20
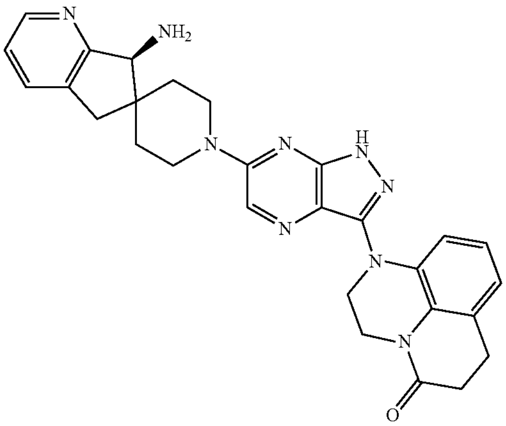
21
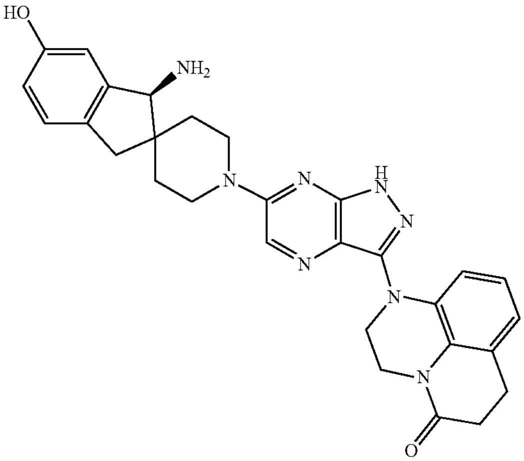
22
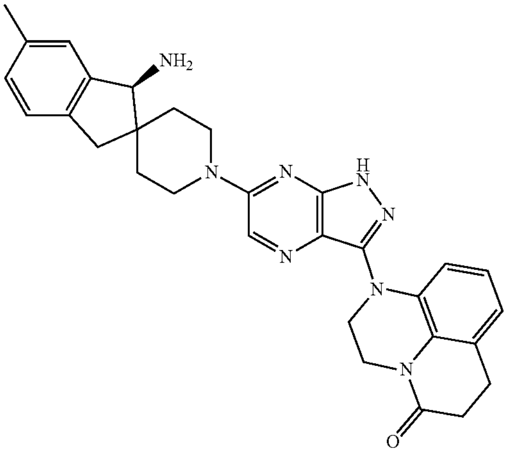

-continued
23
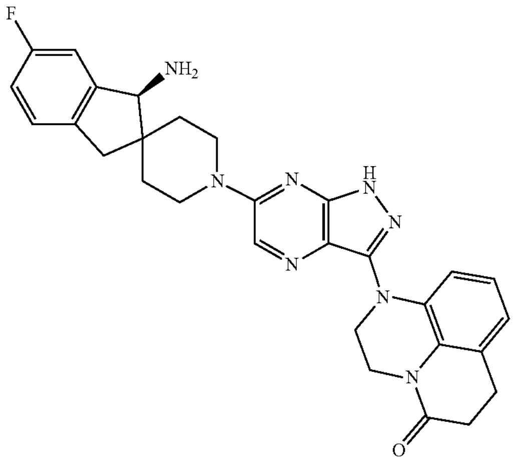
24
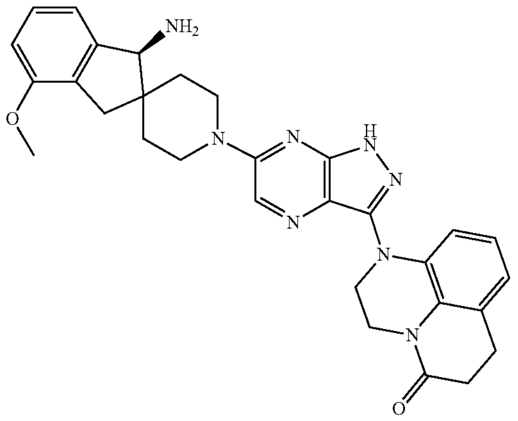
25
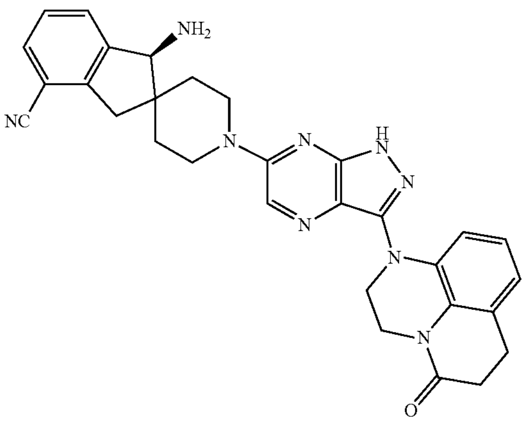
-continued
26
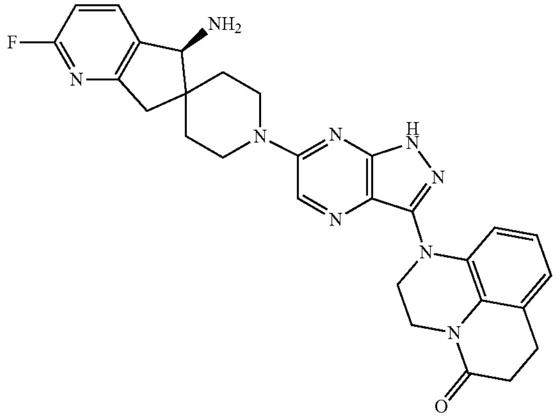
27
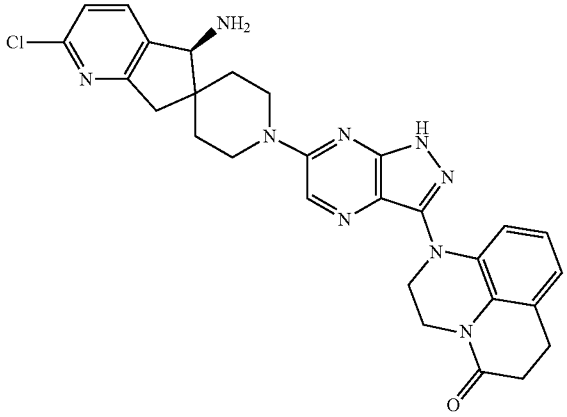
28
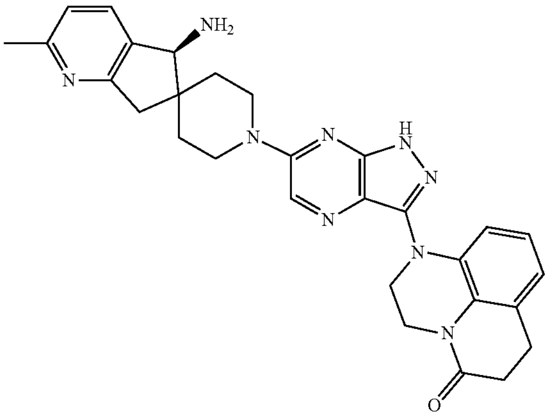

-continued
29
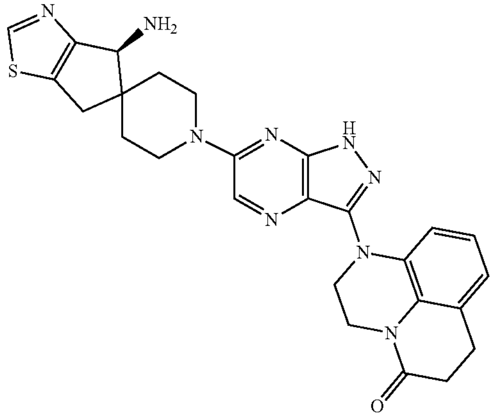
30
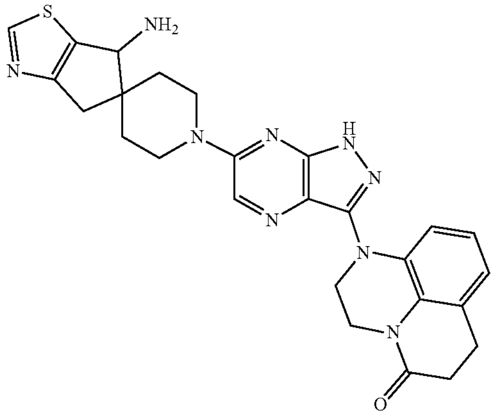
31
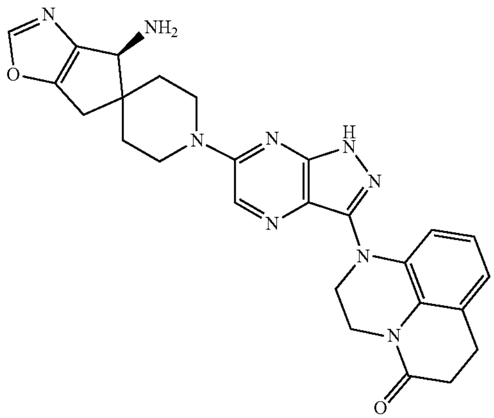
-continued
32
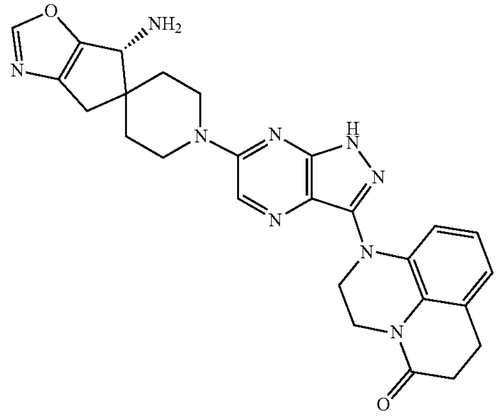
33
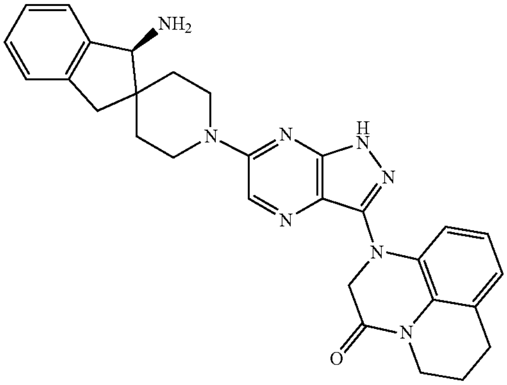
34
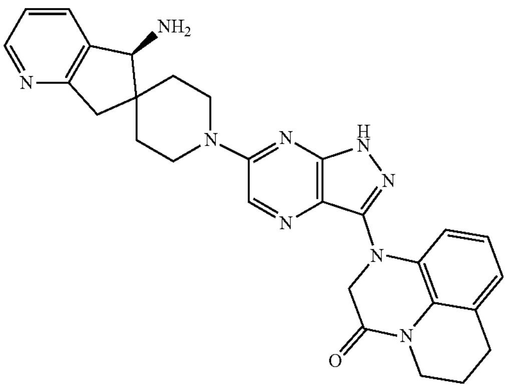

35
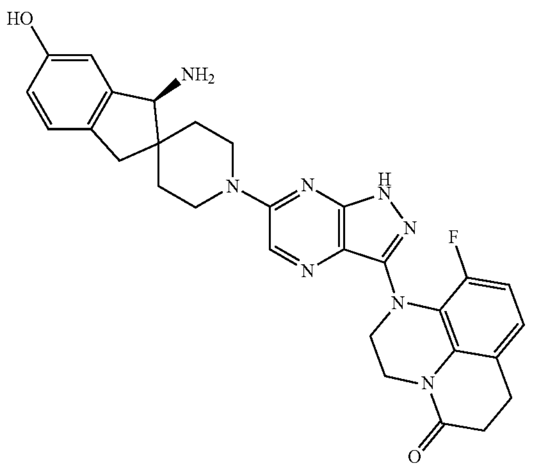
36
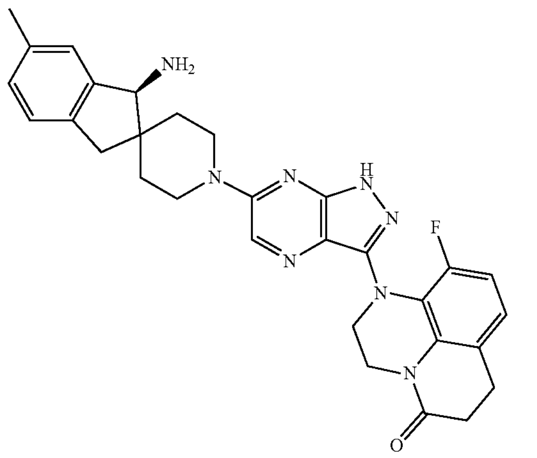
37
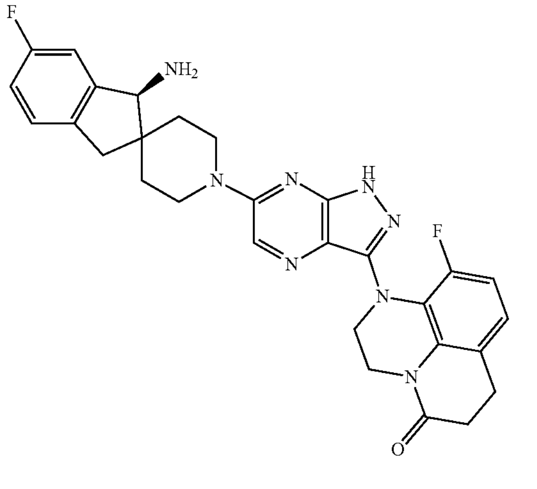
38
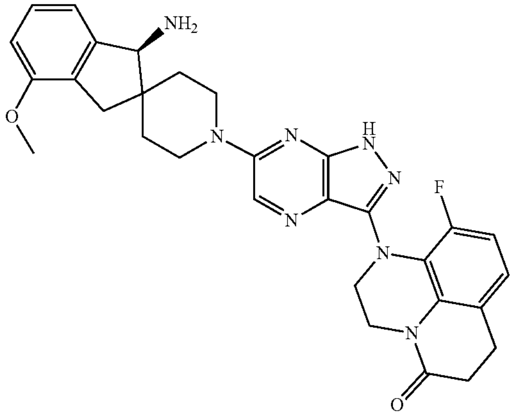
39
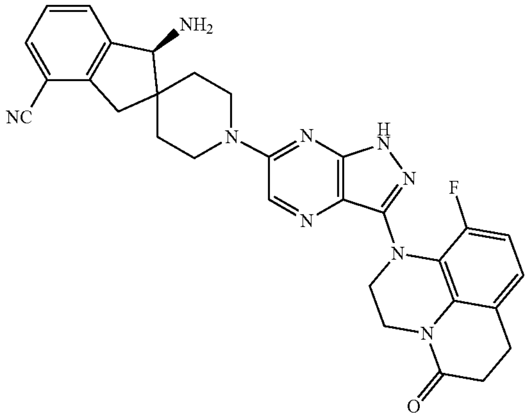
40
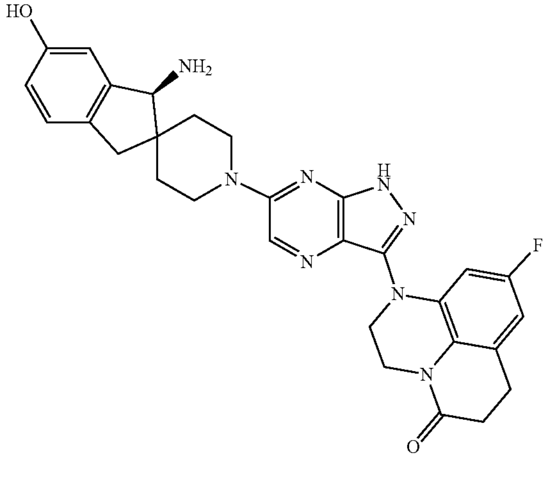

-continued
41
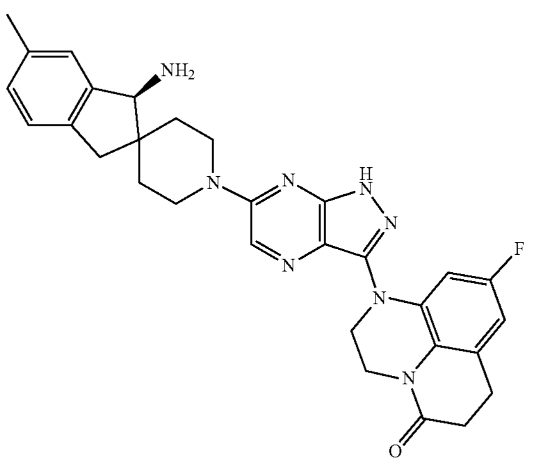
42
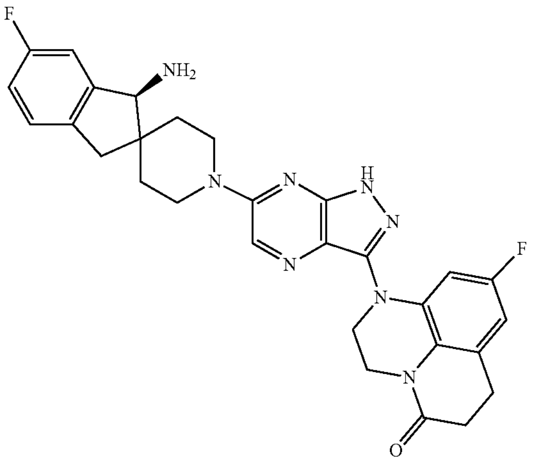
43
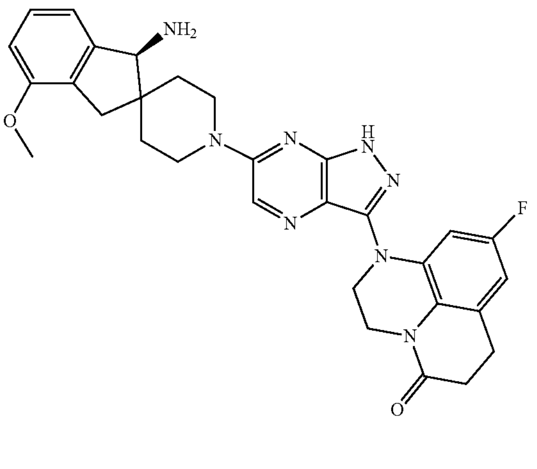
-continued
44
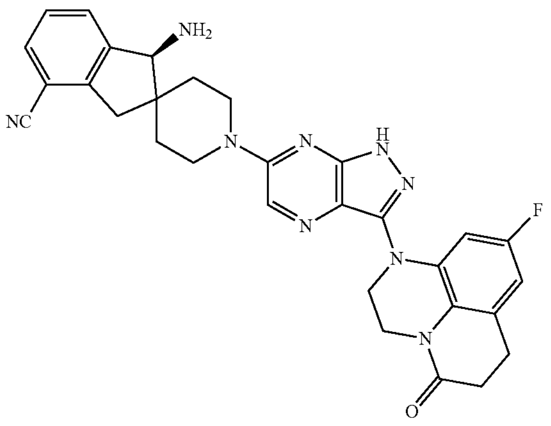
45
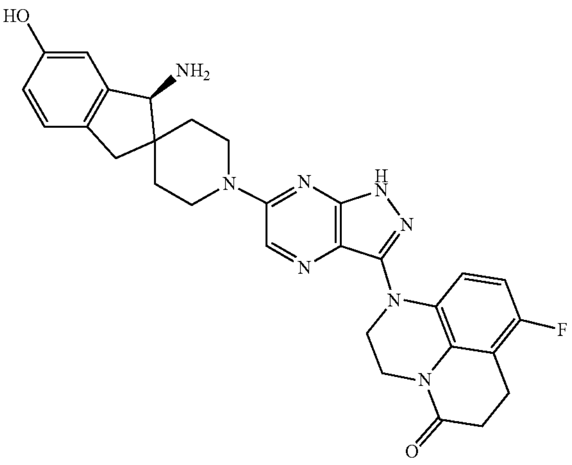
46
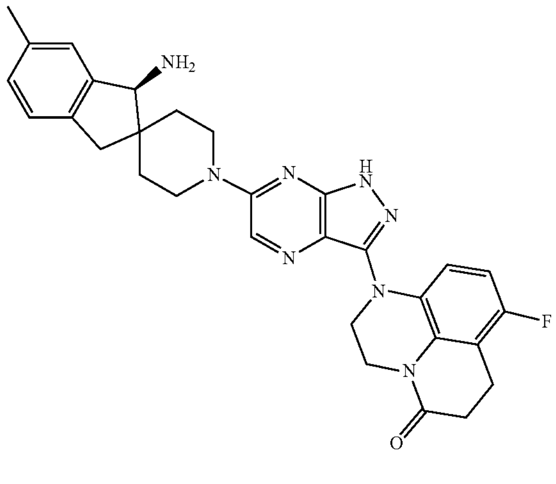

-continued

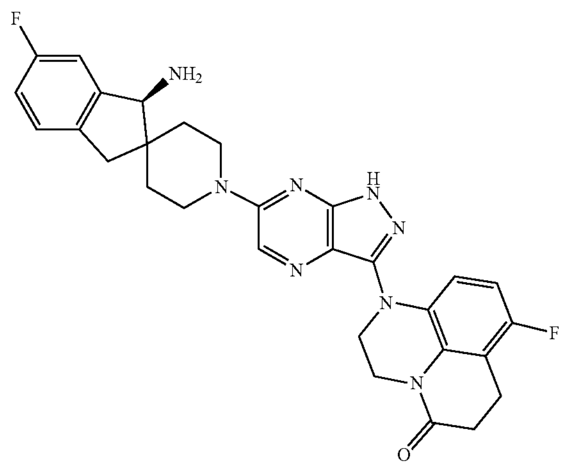

47

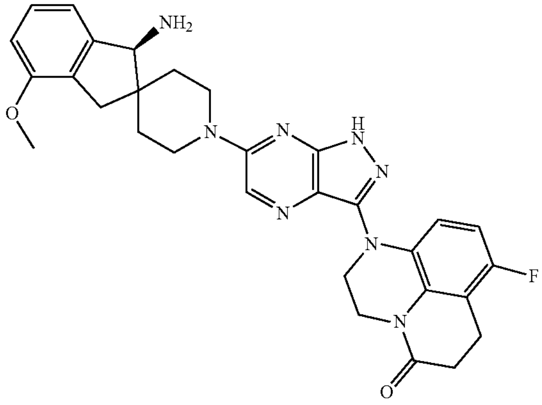

48 or

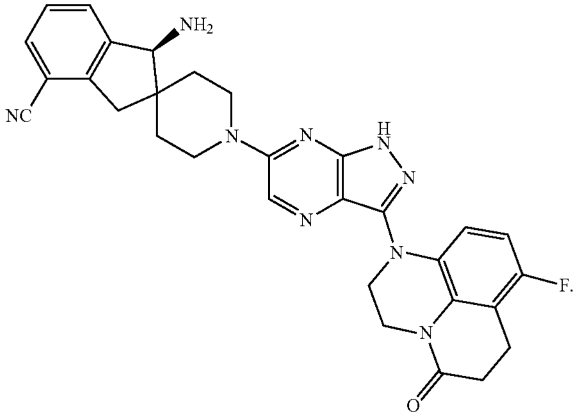

49

The present invention is further intended to provide a pharmaceutical composition including a pharmaceutically acceptable carrier, diluent and/or excipient, and the compound of general formula (1) or the isomer, the crystalline form, the pharmaceutically acceptable salt, the hydrate or the solvate thereof of the present invention as an active ingredient.

The present invention is still further intended to provide use of the compound of general formula (1) or the isomer, the crystalline form, the pharmaceutically acceptable salt, the hydrate or the solvate thereof of the present invention, or the pharmaceutical composition described above in the preparation of a medicament for treating, regulating, or preventing a disease related to SHP2 protein, wherein the disease is preferably a cancer, and the cancer is a hematologic cancer or a solid tumor.

The present invention is even further intended to provide a method for treating, regulating, or preventing a disease related to SHP2 protein, including: administering to a subject a therapeutically effective amount of the compound of general formula (1) or the isomer, the crystalline form, the pharmaceutically acceptable salt, the hydrate or the solvate thereof of the present invention, or the pharmaceutical composition described above.

Through synthesis and careful studies of various classes of novel compounds with inhibitory effects on SHP2, the inventors have discovered that the compound of general formula (1) has surprisingly strong inhibitory activity against SHP2.

It should be understood that both the above general description and the following detailed description of the present invention are exemplary and explanatory, and are intended to provide further explanation of the present invention claimed.

Synthesis of Compounds

Methods for preparing the compounds of general formula (1) of the present invention are specifically described below, but these specific methods do not limit the present invention in any way.

The compounds of general formula (1) described above can be synthesized using standard synthetic techniques or well-known techniques in combination with the methods described herein. In addition, the solvents, temperatures and other reaction conditions mentioned herein can vary. Starting materials for the synthesis of the compounds can be obtained synthetically or commercially. The compounds described herein and other related compounds with different substituents can be synthesized using well-known techniques and starting materials, including the methods found in March, ADVANCED ORGANIC CHEMISTRY, $4^{th}$ Ed., (Wiley 1992); Carey and Sundberg, ADVANCED ORGANIC CHEMISTRY, $4^{th}$ Ed., Vols. A and B (Plenum 2000, 2001); and Green and Wuts, PROTECTIVE GROUPS IN ORGANIC SYNTHESIS, $3^{rd}$ Ed., (Wiley 1999). General methods for preparing the compounds can be changed by using appropriate reagents and conditions for introducing different groups into the molecular formulas provided herein. In one aspect, the compounds described herein are prepared according to methods well known in the art. However, the conditions of the methods, such as reactants, solvents, bases, the amount of the compounds used, reaction temperature and time required for the reaction are not limited to the following explanation. The compounds of the present invention can also be conveniently prepared by optionally combining various synthetic methods described herein or known in the art, and such combinations can be easily determined by those skilled in the art to which the present invention pertains. In one aspect, the present invention further provides a method for preparing the compound of general formula (1), which is prepared using general reaction scheme 1 below:

General Reaction Scheme 1

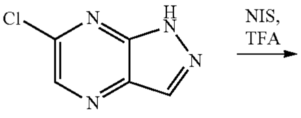

1-1

-continued

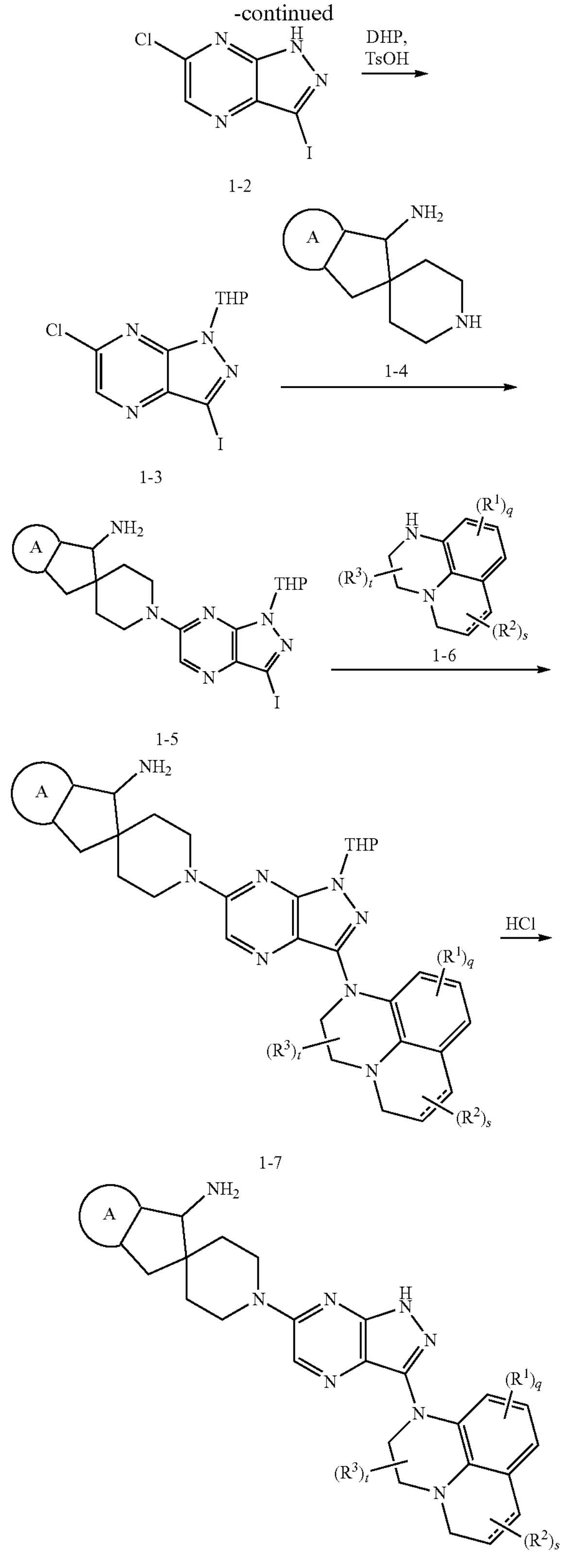

1-2

1-4

1-3

1-6

1-5

1-7

1-8

Embodiments of the compound of general formula (1) can be prepared according to general reaction scheme 1, wherein $R^1$, $R^2$, $R^3$, q, s, t and ring A are as defined above, H represents hydrogen, N represents nitrogen, Cl represents chlorine, I represents iodine, DHP represents 3,4-dihydro-2H-pyran, and THP represents tetrahydropyran. As shown in general reaction scheme 1, compound 1-1 is subjected to a substitution reaction with NIS under an acidic condition to generate compound 1-2, compound 1-2 reacts with DHP under an acidic condition to generate compound 1-3, compound 1-3 reacts with compound 1-4 under a basic condition to generate compound 1-5, compound 1-5 reacts with compound 1-6 to generate compound 1-7, and compound 1-7 is subjected to THP removal under an acidic condition to generate target compound 1-8.

Further Forms of Compounds

"Pharmaceutically acceptable" herein refers to a substance, such as a carrier or diluent, which will not lead to loss of biological activity or properties of a compound and is relatively non-toxic. For example, when an individual is given a substance, the substance will not cause undesired biological effects or interact with any component contained therein in a deleterious manner.

The term "pharmaceutically acceptable salt" refers to a form of a compound that does not cause significant irritation to the organism receiving the administration or eliminate the biological activity and properties of the compound. In certain specific aspects, the pharmaceutically acceptable salt is obtained by subjecting the compound of general formula (1) to a reaction with acids, e.g., inorganic acids such as hydrochloric acid, hydrobromic acid, hydrofluoric acid, sulfuric acid, phosphoric acid, nitric acid, carbonic acid and the like; organic acids such as formic acid, acetic acid, propionic acid, oxalic acid, trifluoroacetic acid, malonic acid, succinic acid, fumaric acid, maleic acid, lactic acid, malic acid, tartaric acid, citric acid, picric acid, methanesulfonic acid, benzenesulfonic acid, p-toluenesulfonic acid and the like; and acidic amino acids such as aspartic acid, glutamic acid and the like.

It should be understood that references to pharmaceutically acceptable salts include solvent addition forms or crystalline forms, especially solvates or polymorphs. A solvate contains either stoichiometric or non-stoichiometric amount of solvent and is selectively formed during crystallization in a pharmaceutically acceptable solvent such as water and ethanol. Hydrates are formed when the solvent is water, or alcoholates are formed when the solvent is ethanol. The solvates of the compound of general formula (1) are conveniently prepared or formed according to the methods described herein. For example, hydrates of the compound of general formula (1) are conveniently prepared by recrystallization in a mixed solvent of water/organic solvent, wherein the organic solvent used includes, but is not limited to, tetrahydrofuran, acetone, ethanol or methanol. Furthermore, the compounds described herein may be present in either a non-solvated form or a solvated form. In general, the solvated forms are considered equivalent to the non-solvated forms for purposes of the compounds and methods provided herein.

In other specific examples, the compound of general formula (1) is prepared in different forms including, but not limited to, amorphous, pulverized and nanoparticle forms. In addition, the compound of general formula (1) includes crystalline forms, and may also be polymorphs. Polymorphs include different lattice arrangements of the same elements of a compound. The polymorphs generally have different X-ray diffraction spectra, infrared spectra, melting points, density, hardness, crystalline forms, optical and electrical properties, stability and solubility. Different factors such as a recrystallization solvent, crystallization rate, and storage temperature may lead to a single dominant crystalline form.

In another aspect, the compound of general formula (1) may have a chiral center and/or axial chirality, and thus may be present in the form of a racemate, a racemic mixture, a single enantiomer, a diastereomeric compound, a single diastereomer and a cis-trans isomer. Each chiral center or axial chirality will independently produce two optical isomers, and all possible optical isomers, diastereomeric mixtures, and pure or partially pure compounds are included within the scope of the present invention. The present invention is meant to include all such isomeric forms of these compounds.

The compound of the present invention may contain unnatural proportions of atomic isotopes at one or more of the atoms that constitute the compound. For example, the compound may be labeled with radioactive isotopes, such as tritium ($^{3}H$), iodine-125 ($^{125}I$), and C-14 ($^{14}C$). For another example, deuterium can be used to substitute a hydrogen atom to form a deuterated compound. The bond formed by deuterium and carbon is stronger than that formed by common hydrogen and carbon, and compared with an undeuterated medicament, the deuterated medicament generally has the advantages of reduced adverse effects, increased medicament stability, enhanced efficacy, prolonged in vivo half-life, and the like. All isotopic variations of the compound of the present invention, whether radioactive or not, are contained within the scope of the present invention.

TERMINOLOGY

Unless otherwise stated, the terms used in the present application, including those in the specification and claims, are defined as follows. It must be noted that in the specification and the appended claims, the singular forms "a" and "an" include plural meanings unless clearly indicated otherwise. Unless otherwise stated, conventional methods for mass spectrometry, nuclear magnetic resonance spectroscopy, HPLC, protein chemistry, biochemistry, recombinant DNA technology and pharmacology are used. As used herein, "or" or "and" refers to "and/or" unless otherwise stated.

Unless otherwise specified, for the convenience of compound nomenclature, ring A is defined in the present application assuming that ring A is named as a separate group (not fused to other rings). In general formula (1), ring A is fused to an adjacent group.

Unless otherwise specified, "alkyl" refers to a saturated aliphatic hydrocarbon group, including linear and branched groups containing 1 to 6 carbon atoms. Lower alkyl groups containing 1 to 4 carbon atoms, such as methyl, ethyl, propyl, 2-propyl, n-butyl, isobutyl, or tert-butyl, are preferred. As used herein, "alkyl" includes unsubstituted and substituted alkyl, particularly alkyl substituted with one or more halogens. Preferred alkyl is selected from $CH_3$, $CH_3CH_2$, $CF_3$, $CHF_2$, $CF_3CH_2$, $CF_3(CH_3)CH$, $^{i}$Pr, $^{n}$Pr, $^{i}$Bu, $^{n}$Bu or $^{t}$Bu.

Unless otherwise specified, "alkenyl" refers to an unsaturated aliphatic hydrocarbon group containing carbon-carbon double bonds, including linear or branched groups containing 1 to 14 carbon atoms. Lower alkenyl groups containing 1 to 4 carbon atoms, such as vinyl, 1-propenyl, 1-butenyl, or 2-methylpropenyl, are preferred.

Unless otherwise specified, "alkynyl" refers to an unsaturated aliphatic hydrocarbon group containing carbon-carbon triple bonds, including linear and branched groups containing 1 to 14 carbon atoms. Lower alkynyl groups containing 1 to 4 carbon atoms, such as ethynyl, 1-propynyl, or 1-butynyl, are preferred.

Unless otherwise specified, "cycloalkyl" refers to a non-aromatic hydrocarbon ring system (monocyclic, bicyclic or polycyclic), and partially unsaturated cycloalkyl may be referred to as "cycloalkenyl" if the carbocyclic ring contains at least one double bond, or "cycloalkynyl" if the carbocyclic ring contains at least one triple bond. Cycloalkyl may include monocyclic or polycyclic groups (e.g., having 2, 3 or 4 fused rings) and spiro rings. In some embodiments, cycloalkyl is monocyclic. In some embodiments, cycloalkyl is monocyclic or bicyclic. The ring carbon atoms of cycloalkyl may optionally be oxidized to form an oxo or sulfido group. Cycloalkyl further includes cycloalkylene. In some embodiments, cycloalkyl contains 0, 1 or 2 double bonds. In some embodiments, cycloalkyl contains 1 or 2 double bonds (partially unsaturated cycloalkyl). In some embodiments, cycloalkyl may be fused to aryl, heteroaryl, cycloalkyl and heterocycloalkyl. In some embodiments, cycloalkyl may be fused to aryl, cycloalkyl and heterocycloalkyl. In some embodiments, cycloalkyl may be fused to aryl and heterocycloalkyl. In some embodiments, cycloalkyl may be fused to aryl and cycloalkyl. Examples of cycloalkyl include cyclopropyl, cyclobutyl, cyclopentyl, cyclohexyl, cycloheptyl, cyclopentenyl, cyclohexenyl, cyclohexadienyl, cycloheptatrienyl, norcamphanyl, norpinanyl, norcarnyl, bicyclo[1.1.1]pentyl, bicyclo[2.1.1]hexyl and the like.

Unless otherwise specified, "aryl" refers to an aromatic hydrocarbon group, which is monocyclic or polycyclic; for example, a monocyclic aryl ring may be fused to one or more carbocyclic aromatic groups. Examples of aryl include, but are not limited to, phenyl, naphthyl, and phenanthryl.

Unless otherwise specified, "heteroaryl" refers to an aromatic group containing one or more heteroatoms (O, S, or N), and the heteroaryl is monocyclic or polycyclic. For example, a monocyclic heteroaryl ring is fused to one or more carbocyclic aromatic groups or other monocyclic heterocycloalkyl groups. Examples of heteroaryl include, but are not limited to, pyridinyl, pyridazinyl, imidazolyl, pyrimidinyl, pyrazolyl, triazolyl, pyrazinyl, quinolinyl, isoquinolinyl, furanyl, thienyl, isoxazolyl, thiazolyl, oxazolyl, isothiazolyl, pyrrolyl, indolyl, benzimidazolyl, benzofuranyl, benzothiazolyl, benzothienyl, benzoxazolyl, benzopyridinyl, pyrrolopyrimidinyl, 1H-pyrrolo[3,2-b]pyridinyl, 1H-pyrrolo[2,3-c]pyridinyl, 1H-pyrrolo[3,2-c]pyridinyl, 1H-pyrrolo[2,3-b]pyridinyl,

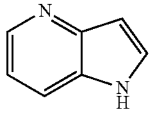, 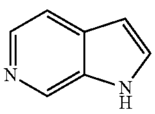, 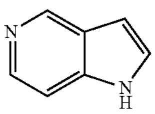, and

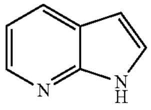.

Unless otherwise specified, "heterocycloalkyl" refers to a non-aromatic ring or ring system, which may optionally contain one or more alkenylene as part of the ring structure, having at least one heteroatom ring member independently selected from boron, phosphorus, nitrogen, sulfur, oxygen, and phosphorus. Partially unsaturated heterocycloalkyl may be referred to as "heterocycloalkenyl" if heterocycloalkyl contains at least one double bond, or “heterocycloalkynyl” if the heterocycloalkyl contains at least one triple bond. Heterocycloalkyl may include monocyclic, bicyclic, spiro ring, or polycyclic systems (e.g., having two fused or bridged rings). In some embodiments, heterocycloalkyl is a monocyclic group having 1, 2, or 3 heteroatoms independently selected from nitrogen, sulfur, and oxygen. The ring carbon atoms and heteroatoms of heterocycloalkyl may optionally be oxidized to form oxo or sulfido groups or other oxidized bonds (e.g., C(O), S(O), C(S) or S(O)2, N-oxides, etc.), or the nitrogen atoms may be quaternized. Heterocycloalkyl may be attached via a ring carbon atom or a ring heteroatom. In some embodiments, heterocycloalkyl contains 0 to 3 double bonds. In some embodiments, heterocycloalkyl contains 0 to 2 double bonds. The definition of heterocycloalkyl further includes moieties having one or more aromatic rings fused to (i.e., sharing a bond with) the heterocycloalkyl ring, for example, benzo-derivatives of piperidine, morpholine, azepin, thienyl, or the like. Heterocycloalkyl containing a fused aromatic ring may be attached via any ring atom, including ring atoms of the fused aromatic ring. Examples of heterocycloalkyl include, but are not limited to, azetidinyl, azepinyl, dihydrobenzofuranyl, dihydrofuranyl, dihydropyranyl, N-morpholinyl, 3-oxa-9-azaspiro[5.5]undecyl, 1-oxa-8-azaspiro[4.5]decyl, piperidinyl, piperazinyl, oxopiperazinyl, pyranyl, pyrrolidinyl, quininyl, tetrahydrofuranyl, tetrahydropyranyl, 1,2,3,4-tetrahydroquinolinyl, tropanyl, 4,5,6,7-tetrahydrothiazolo[5,4-c]pyridinyl, 4,5,6,7-tetrahydro-1H-imidazo[4,5-c] pyridine, N-methylpiperidinyl, tetrahydroimidazolyl, pyrazolidinyl, butyrolactam, valerolactam, imidazolidinonyl, hydantoinyl, dioxolanyl, phthalimidyl, pyrimidine-2,4(1H,3H)-dione, 1,4-dioxanyl, morpholinyl, thiomorpholinyl, thiomorpholinyl-S-oxide, thiomorpholinyl-S,S-oxide, piperazinyl, pyranyl, pyridonyl, 3-pyrrolinyl, thiopyranyl, pyronyl, tetrahydrothienyl, 2-azaspiro[3.3]heptanyl, indolinyl,

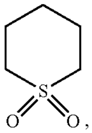,
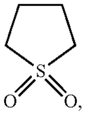,
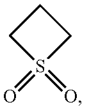,
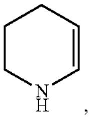,
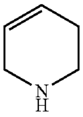,

, and
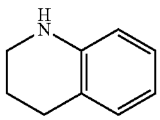.

Unless otherwise specified, “oxo” refers to =O; for example, a group formed by substitution of carbon with one oxo is “carbonyl

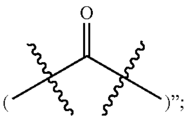”;

a group formed by substitution of sulfur with one oxo is “sulfinyl

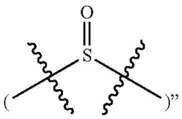”

and a group formed by substitution of sulfur with two oxos is “sulfonyl

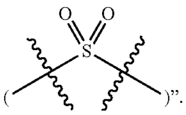”.

Unless otherwise specified, “halogen” (or halo) refers to fluorine, chlorine, bromine or iodine. The term “halo” (or “halogenated”) before a group name indicates that the group is partially or fully halogenated, that is, substituted in any combination with F, Cl, Br or I, preferably with F or Cl.

“Optional” or “optionally” means that the subsequently described event or circumstance may, but does not necessarily, occur, and the description includes instances where the event or circumstance occurs and instances where the event or circumstance does not occur.

The substituent “—O—$CH_2$—O—” means that two oxygen atoms in the substituent are linked to two adjacent carbon atoms in the heterocycloalkyl, aryl or heteroaryl, for example:

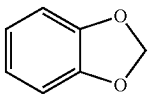.

When the number of a linker group is 0, such as —$(CH_2)_0$—, it means that the linker group is a single bond.

When one of the variables is selected from a chemical bond, it means that the two groups linked by this variable are linked directly. For example, when L in X-L-Y represents a chemical bond, it means that the structure is actually X-Y The term “membered ring” includes any cyclic structure. The term “membered” is intended to refer to the number of backbone atoms that form a ring. For example, cyclohexyl, pyridinyl, pyranyl and thiopyranyl are six-membered rings, and cyclopentyl, pyrrolyl, furanyl and thienyl are five-membered rings.

The term “moiety” refers to a specific portion or functional group of a molecule. A chemical moiety is generally considered to be a chemical entity contained in or attached to a molecule.

Unless otherwise stated, the absolute configuration of a stereooenic center is represented by a wedged solid bond () and a wedged dashed bond (), and the relative configuration of a stereogenic center is represented by a straight solid bond () and a straight dashed bond (). A wavy line () represents a wedged solid bond () or a wedged dashed bond (), or a wavy line () represents a straight solid bond () or a straight dashed bond ().

Unless otherwise stated, a single bond or a double bond is represented by .

Specific Pharmaceutical and Medical Terminology

The term "acceptable", as used herein, means that a formula component or an active ingredient does not unduly and adversely affect a general therapeutic target's health.

The terms "treatment", "treatment course", and "therapy", as used herein, include alleviating, inhibiting, or ameliorating a symptom or condition of a disease; inhibiting the development of complications; ameliorating or preventing underlying metabolic syndrome; inhibiting the development of a disease or symptom, e.g., controlling the progression of a disease or condition; alleviating a disease or symptom; leading to disease or symptom regression; and alleviating a complication caused by a disease or symptom, or preventing or treating a sign caused by a disease or symptom. As used herein, a compound or pharmaceutical composition, when administered, can ameliorate a disease, symptom, or condition, which particularly refers to ameliorating the severity, delaying the onset, slowing the progression, or reducing the duration of the disease. Fixed or temporary administration, or continuous or intermittent administration, may be attributed to or associated with the administration.

"Active ingredient" refers to the compound of general formula (1), and pharmaceutically acceptable inorganic or organic salts of the compound of general formula (1). The compound of the present invention may contain one or more asymmetric centers (chiral center or axial chirality) and thus occurs in the forms of a racemate, a racemic mixture, a single enantiomer, a diastereomeric compound and a single diastereomer. Asymmetric centers that may be present depend on the nature of the various substituents on the molecule. Each of such asymmetric centers will independently produce two optical isomers, and all possible optical isomers, diastereomeric mixtures and pure or partially pure compounds are included within the scope of the present invention. The present invention is meant to include all such isomeric forms of these compounds.

The terms such as "compound", "composition", "agent", or "medicine or medicament" are used interchangeably herein and all refer to a compound or composition that, when administered to an individual (human or animal), is capable of inducing a desired pharmacological and/or physiological response by local and/or systemic action.

The term "administered, administering, or administration" refers herein to the direct administration of the compound or composition, or the administration of a prodrug, derivative, analog, or the like of the active compound.

Although the numerical ranges and parameters defining the broad scope of the present invention are approximations, the related numerical values set forth in the specific examples have been presented herein as precisely as possible. Any numerical value, however, inherently contains a standard deviation necessarily resulting from certain methods of testing. Herein, "about" generally means that the actual value is within a particular value or range ±10%, 5%, 1% or 0.5%. Alternatively, the term "about" indicates that the actual numerical value falls within the acceptable standard error of a mean, as considered by those skilled in the art. All ranges, quantities, numerical values, and percentages used herein (e.g., to describe an amount of a material, a length of time, a temperature, an operating condition, a quantitative ratio, and the like) are to be understood as being modified by the word "about", except in the experimental examples or where otherwise explicitly indicated. Accordingly, unless otherwise contrarily stated, the numerical parameters set forth in the specification and the appended claims are all approximations that may vary as desired. At least, these numerical parameters should be understood as the significant digits indicated or the numerical values obtained using conventional rounding rules.

Unless otherwise defined in the specification, the scientific and technical terms used herein have the same meaning as commonly understood by those skilled in the art. Furthermore, nouns in their singular forms used in the specification encompass their plural forms, unless contradicted by context; nouns in their plural forms used also encompass their singular forms.

Therapeutic Use

The compound of general formula (1) or the pharmaceutical composition of the present invention is generally useful for inhibiting SHP2 protein, and therefore, for treating one or more disorders related to the activity of SHP2 protein. Therefore, in certain embodiments, the present invention provides a method for treating SHP2 protein-mediated disorders, which comprises the step of administering to a patient in need thereof the compound of general formula (1) or the pharmaceutically acceptable composition thereof of the present invention. In some embodiments, a method for treating cancer is provided, the method including administering to an individual in need thereof an effective amount of any aforementioned pharmaceutical composition including the compound of structural general formula (1). In some embodiments, the cancer includes, but is not limited to, hematologic malignancies (leukemias, lymphomas, and myelomas including multiple myeloma, myelodysplastic syndrome and myeloproliferative family syndrome), solid tumors (carcinomas such as prostate, breast, lung, colon, pancreas, kidney, ovary and soft tissue cancers, osteosarcoma, and interstitial tumors), and the like.

Route of Administration

The compound and the pharmaceutically acceptable salt thereof of the present invention can be made into various formulations including a safe and effective amount of the compound or the pharmaceutically acceptable salt thereof of the present invention, and a pharmaceutically acceptable excipient or carrier, wherein the "safe and effective amount" means that the amount of the compound is sufficient to significantly improve the condition without causing serious adverse effects. The safe and effective amount of the compound is determined according to the age, condition, course of treatment, and other specific conditions of a treated subject.

The "pharmaceutically acceptable excipient or carrier" refers to one or more compatible solid or liquid fillers or gel substances that are suitable for human use and must be of sufficient purity and sufficiently low toxicity. "Compatible" herein means that the components of the composition are capable of intermixing with the compound of the present invention and with each other, without significantly diminishing the pharmaceutical efficacy of the compound. Examples of pharmaceutically acceptable excipients or carriers include cellulose and derivatives thereof (e.g., sodium carboxymethylcellulose, sodium ethylcellulose, or cellulose acetate), gelatin, talc, solid lubricants (e.g., stearic acid or magnesium stearate), calcium sulfate, vegetable oil (e.g., soybean oil, sesame oil, peanut oil, or olive oil), polyols (e.g., propylene glycol, glycerol, mannitol, or sorbitol), emulsifiers (e.g., Tween®), wetting agents (e.g., sodium lauryl sulfate), colorants, flavoring agents, stabilizers, antioxidants, preservatives, pyrogen-free water, etc.

When the compound of the present invention is administered, it may be administered orally, rectally, parenterally (intravenously, intramuscularly, or subcutaneously), or topically.

Solid dosage forms for oral administration include capsules, tablets, pills, pulvises, and granules. In these solid dosage forms, the active compound is mixed with at least one conventional inert excipient (or carrier), such as sodium citrate or dicalcium phosphate, or with the following ingredients: (a) fillers or extenders, such as starch, lactose, sucrose, glucose, mannitol, and silicic acid; (b) binders, such as hydroxymethyl cellulose, alginate, gelatin, polyvinylpyrrolidone, sucrose, and acacia; (c) humectants, such as glycerol; (d) disintegrants, such as agar, calcium carbonate, potato or tapioca starch, alginic acid, certain complex silicates, and sodium carbonate; (e) solution retarders, such as paraffin; (f) absorption accelerators, such as quaternary ammonium compounds; (g) wetting agents, such as cetyl alcohol and glycerol monostearate; (h) adsorbents, such as kaolin; and (i) lubricants, such as talc, calcium stearate, magnesium stearate, solid polyethylene glycol and sodium lauryl sulfate, or mixtures thereof. In the case of capsules, tablets, and pills, the dosage forms may further include buffers.

Solid dosage forms such as tablets, dragees, capsules, pills, and granules can be prepared using coatings and shells such as enteric coatings and other materials well known in the art. They may include opacifying agents, and the active compound or compound in such a composition may be released in a certain part of the digestive tract in a delayed manner. Examples of embedding components that can be used are polymeric substances and wax-based substances.

If necessary, the active compound can also be in microcapsule form with one or more of the excipients described above.

Liquid dosage forms for oral administration include pharmaceutically acceptable emulsions, solutions, suspensions, syrups, and elixirs. In addition to the active compound, the liquid dosage form may include inert diluents commonly used in the art, such as water or other solvents, solubilizers and emulsifiers, for example, ethanol, isopropanol, ethyl carbonate, ethyl acetate, propylene glycol, 1,3-butanediol, dimethylformamide, and oils, especially cottonseed oil, peanut oil, corn germ oil, olive oil, castor oil and sesame oil, or mixtures of these substances.

Besides such inert diluents, the composition may further include adjuvants, such as wetting agents, emulsifiers, suspending agents, sweeteners, flavoring agents, and perfuming agents.

In addition to the active compound, suspensions may include suspending agents, such as ethoxylated isostearyl alcohols, polyoxyethylene sorbitol and sorbitan esters, microcrystalline cellulose, aluminum methylate and agar, or mixtures of these substances.

Compositions for parenteral injection may include physiologically acceptable sterile aqueous or anhydrous solutions, dispersions, suspensions or emulsions, and sterile powders for redissolving into sterile injectable solutions or dispersions. Suitable aqueous and non-aqueous carriers, diluents, solvents, or excipients include water, ethanol, polyols, and suitable mixtures thereof.

Dosage forms for topical administration of the compound of the present invention include ointments, pulvises, patches, sprays, and inhalants. The active ingredient is mixed under sterile conditions with a physiologically acceptable carrier and any preservatives, buffers or propellants that may be required if necessary.

The compound of the present invention may be administered alone or in combination with other pharmaceutically acceptable compounds. When the pharmaceutical composition is used, a safe and effective amount of the compound of the present invention is administered to a mammal (such as a human) to be treated, wherein the dose of administration is a pharmaceutically effective dose. For a human of 60 kg, the daily dose of administration is usually 1-2000 mg, preferably 50-1000 mg. In determining a specific dose, such factors as the route of administration, the health condition of the patient and the like will also be considered, which are well-known to skilled physicians.

The above features mentioned in the present invention or those mentioned in the examples may be combined arbitrarily. All the features disclosed in this specification may be used with any composition form and the various features disclosed in this specification may be replaced with any alternative features that provide the same, equivalent, or similar purpose. Thus, unless otherwise specified, the features disclosed herein are merely general examples of equivalent or similar features.

DETAILED DESCRIPTION

Various specific aspects, features, and advantages of the compounds, methods, and pharmaceutical compositions described above will be set forth in detail in the following description, which will make the content of the present invention very clear. It should be understood that the detailed description and examples below describe specific examples for reference only. After reading the description of the present invention, those skilled in the art can make various changes or modifications to the present invention, and such equivalents also fall within the scope of the present application defined herein.

In all the examples, $^1$H-NMR spectra were recorded with a Varian Mercury 400 nuclear magnetic resonance spectrometer, and chemical shifts are expressed in δ (ppm); silica gel for separation was 200-300 mesh silica gel if not specified, and the ratio of the eluents was a volume ratio.

The following abbreviations are used in the present invention: $Ac_2O$ for acetic anhydride; $(Boc)_2O$ for di-tert-butyl dicarbonate; BnBr for benzyl bromide; $CDCl_3$ for deuterated chloroform; $Cs_2CO_3$ for cesium carbonate; EtOAc for ethyl acetate; Hexane for n-hexane; HPLC for high-performance liquid chromatography; MeCN for acetonitrile; DCM for dichloromethane; DIPEA for diisopropylethylamine; Dioxane for 1,4-dioxane; DMF for N,N-dimethylformamide; DMP for Dess-Martin oxidant; DMAP for 4-(dimethylamino)pyridine; DMSO for dimethyl sulfoxide; EtOH for ethanol; EtMgBr for ethylmagnesium bromide; h for hour; IPA for isopropanol; ISCO® for a Biotage Isolera Prime flash preparative liquid chromatograph; min for minute; $K_2CO_3$ for potassium carbonate; KOAc for potassium acetate; KOH for potassium hydroxide; $K_3PO_4$ for potassium phosphate; LDA for lithium diisopropylamide; $LiBH_4$ for lithium borohydride; min for minute; MeOH for methanol; MS for mass spectrometry; MsOH for methanesulfonic acid; n-BuLi for n-butyllithium; NMR for nuclear magnetic resonance; NIS for iodosuccinimide; Pd/C for palladium on carbon; $Pd(PPh_3)_4$ for tetrakis(triphenylphosphine)palladium; $Pd_2(dba)_3$ for tris(dibenzylideneacetone)dipalladium (0); $Pd(dppf)Cl_2$ for [1,1'-bis(diphenylphosphino)ferrocene] dichloropalladium (II); PE for petroleum ether; $POBr_3$ for phosphorus oxybromide; $POCl_3$ for phosphorus oxychloride; PPA for polyphosphoric acid; TEA for triethylamine; TFA for trifluoroacetic acid; $T_3P$ for 1-propanephosphonic anhydride; TsOH for p-toluenesulfonic acid; $Ti(OEt)_4$ for titanium ethoxide; XantPhos for 4,5-bis(diphenylphosphino)-9,9-dimethylxanthene; TfOH for trifluoromethanesulfonic acid; TLC for thin-layer chromatography; XPhos for 2-dicyclohexylphosphonium-2',4',6'-triisopropylbiphenyl.

Preparation Example 1. Synthesis of Intermediate A-1

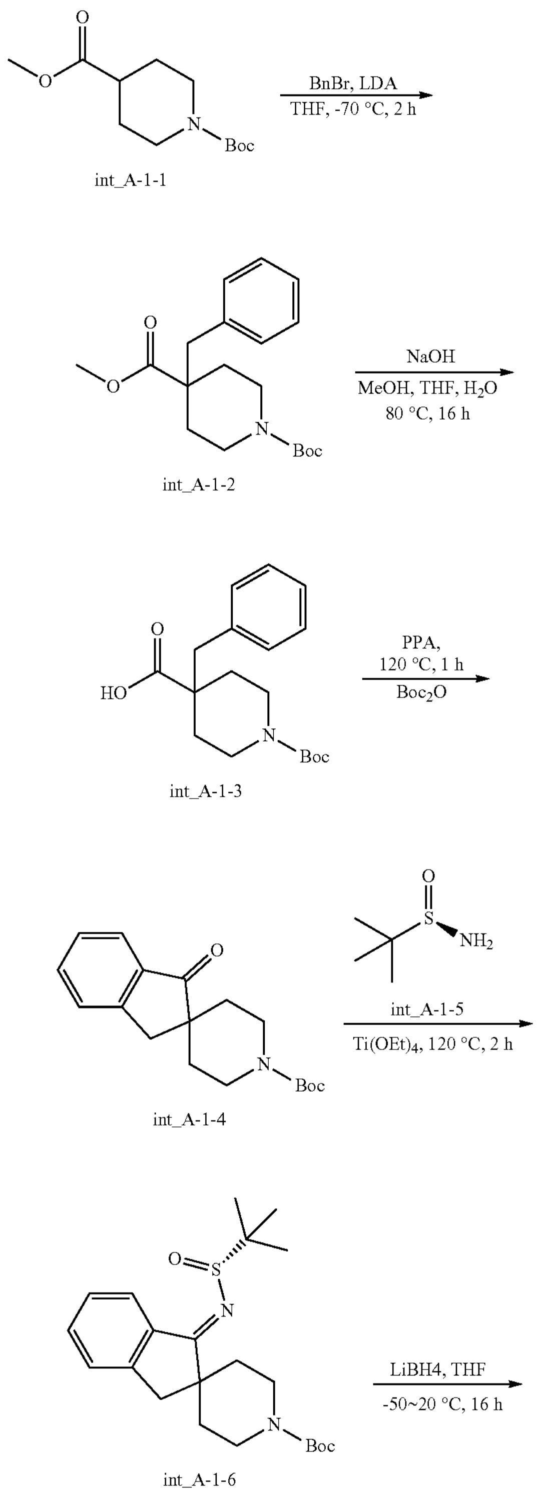

-continued

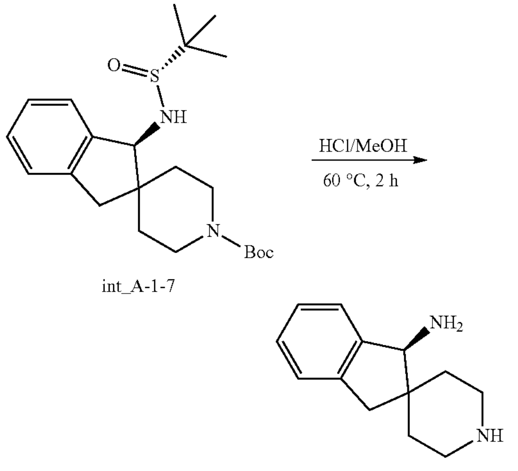

A-1

Step 1: Synthesis of Compound int_A-1-2:

int_A-1-2

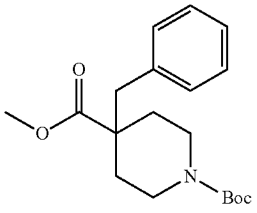

Int_A-1-1 (46 g, 189.07 mmol) was dissolved in THF (500.0 mL). LDA (2 M, 122.89 mL) was added dropwise to the reaction solution at −78 °C under nitrogen atmosphere. After the addition was completed, the reaction solution was stirred at −78 °C for 1 h. To the reaction solution was added dropwise BnBr (33.95 g, 198.52 mmol, 23.58 mL). After the addition was completed, the reaction solution was stirred at −78 °C for another 1 h. LC-MS monitoring showed the reaction was completed. The reaction solution was quenched with a saturated aqueous ammonium chloride solution (200 mL) at −10 °C. The aqueous phase was extracted with ethyl acetate (150 mL×3), and the organic phase was dried over anhydrous sodium sulfate. The organic phase was concentrated under reduced pressure to give a crude product (60 g). The crude product was directly used in the next step.

ESI-MS m/z: 334 $[M+H]^+$.

Step 2: Synthesis of Compound int_A-1-3:

int_A-1-3

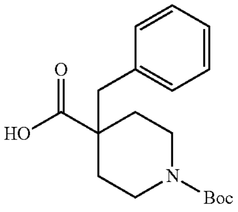

Int_A-1-2 (66 g, 198 mmol) was dissolved in methanol (300 mL) and THF (300 mL). An aqueous NaOH solution (2 M, 296 mL) and water (296 mL) were added at room temperature. The reaction solution was reacted at 80 °C for 16 h. LC-MS monitoring showed the reaction was completed. The reaction solution was concentrated under reduced pressure to remove methanol and THF, and then an aqueous hydrochloric acid solution (2 M, 500 mL) was added to the reaction solution. The mixture was stirred at room temperature for 3 h. A white solid was precipitated. The reaction solution was filtered to give a white solid (41 g, 64.8% yield).

$^1$H NMR: (400 MHz, DMSO-d6) δ=7.30-7.18 (m, 3H), 7.14-7.10 (m, 2H), 3.77 (br d, J=13.6 Hz, 2H), 2.79 (s, 4H), 1.85 (br d, J=13.3 Hz, 2H), 1.38 (s, 9H), 1.36-1.30 (m, 2H).

Step 3: Synthesis of Compound int_A-1-4:

int_A-1-4

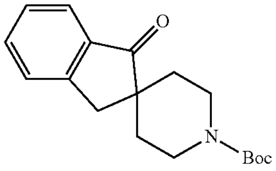

Int_A-1-3 (41 g, 128 mmol) was dissolved in PPA (123 g, 366 mmol). Under argon atmosphere, the mixture was heated to 120 °C and stirred for 2 h. LC-MS monitoring showed the reaction was completed. The reaction solution was cooled to 80 °C. Water (200 mL) was added slowly to the reaction solution, and an aqueous NaOH solution (2 M, 1 L) and $Boc_2O$ (4.19 g, 192 mmol) were added. The mixed solution was reacted at 25 °C for 2 h. The aqueous phase was extracted with ethyl acetate (200 mL×3), and the organic phase was dried over anhydrous sodium sulfate. The organic phase was concentrated under reduced pressure to give a crude product, and the crude product was purified by preparative column chromatography ($SiO_2$, EtOAc/PE=1/3) to give a white solid (17 g, 43.9% yield).

$^1$H NMR: (400 MHz, DMSO-d6) δ=7.75-7.65 (m, 2H), 7.60 (d, J=7.6 Hz, 1H), 7.49-7.42 (m, 1H), 3.96 (br d, J=12.1 Hz, 2H), 3.13 (s, 2H), 2.98 (br s, 2H), 1.65-1.56 (m, 2H), 1.43 (s, 9H), 1.36 (br d, J=12.8 Hz, 2H).

Step 4: Synthesis of Compound int_A-1-6:

int_A-1-6

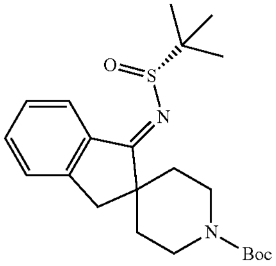

Int_A-1-4 (4 g, 13.27 mmol) and int_A-1-5 (3.22 g, 26.54 mmol) were dissolved in $Ti(OEt)_4$ (30 mL). The reaction solution was heated to 120 °C and reacted for 2 h. LC-MS monitoring showed the reaction was completed. The reaction solution was cooled to room temperature, and then poured into water. A white solid was precipitated. The mixed solution was filtered to give a filtrate. The aqueous phase was extracted with ethyl acetate (100 mL×3), and the organic phase was dried over anhydrous sodium sulfate. The organic phase was concentrated under reduced pressure to give a crude product, which was directly concentrated under reduced pressure to give a crude product (5.37 g). The crude product was directly used in the next step.

ESI-MS m/z: 405 $[M+H]^+$.

Step 5: Synthesis of Compound int_A-1-7:

int_A-1-7

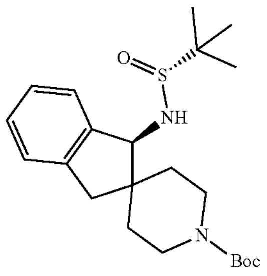

Int_A-1-6 (5.37 g, 13.27 mmol) was dissolved in THE (5 mL). $LiBH_4$ (433.72 mg, 19.91 mmol) was added at −50 °C. After the addition was completed, the reaction solution was heated to room temperature and reacted for 16 h. LC-MS monitoring showed the reaction was completed. $10 \cdot H_2O$ $Na_2SO_4$ (5 g) was added to the reaction solution, and the reaction solution was stirred for another 1 h. The reaction solution was filtered to give a filtrate, and the filtrate was concentrated under reduced pressure to give a crude product. The crude product was purified by preparative column chromatography ($SiO_2$, EtOAc/PE=1/1) to give a white solid (2 g, 37.06% yield).

$^1$H NMR: (400 MHz, CHLOROFORM-d) δ=7.35-7.31 (m, 1H), 7.28-7.20 (m, 3H), 4.52 (d, J=9.5 Hz, 1H), 4.04 (br d, J=13.3 Hz, 2H), 3.55 (br s, 1H), 3.13-2.88 (m, 3H), 2.72 (br d, J=15.8 Hz, 1H), 1.79-1.59 (m, 2H), 1.53 (br dd, J=2.5, 13.1 Hz, 1H), 1.47 (s, 9H), 1.34-1.28 (m, 11H).

Step 6: Synthesis of Compound int_A-1:

A-1

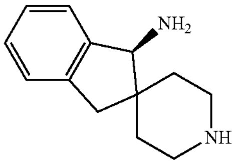

Int_A-1-7 (2 g, 4.92 mmol) was dissolved in methanol (5 mL). HCl (7.97 g, 218 mmol) was introduced into the reaction solution. The reaction solution was heated to 60 °C and reacted for 2 h. LC-MS monitoring showed the reaction was completed. The reaction solution was concentrated under reduced pressure to give a crude product (1.15 g, 97.92% yield). The crude product was directly used in the next step.

MS (ESI): 203 $[M+H]^+$.

Preparation Examples 2-25. Synthesis of Intermediates A-2 to A-25

The target intermediates A-2 to A-25 in Table 1 were obtained by the synthesis methods described above using different starting materials.

TABLE 1
| Intermediate | Intermediate structure | MS (M + H)+ |
|---|---|---|
| A-2 | 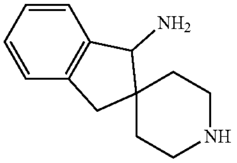 [SMILES: NC1c2ccccc2CC12CCNCC2] | 203 |
| A-3 | 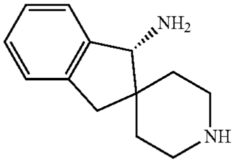 [SMILES: N[C@H]1c2ccccc2CC12CCNCC2] | 203 |
| A-4 | 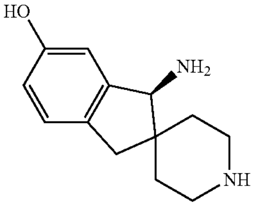 [SMILES: N[C@@H]1c2cc(O)ccc2CC12CCNCC2] | 219 |
| A-5 | 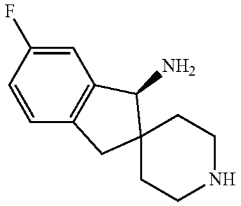 [SMILES: N[C@@H]1c2cc(F)ccc2CC12CCNCC2] | 221 |
| A-6 | 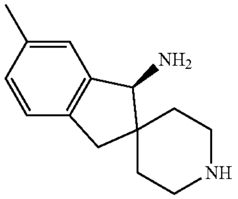 [SMILES: Cc1ccc2c(c1)[C@@H](N)C1(CCNCC1)C2] | 217 |
| A-7 | 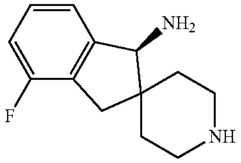 [SMILES: N[C@@H]1c2cccc(F)c2CC12CCNCC2] | 221 |
| A-8 | 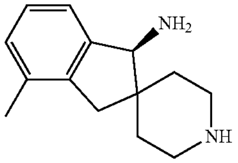 [SMILES: Cc1cccc2c1CC1(CCNCC1)[C@@H]2N] | 217 |
| A-9 | 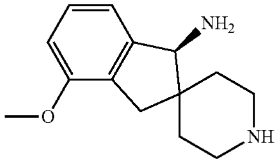 [SMILES: COc1cccc2c1CC1(CCNCC1)[C@@H]2N] | 233 |
TABLE 1-continued
| Intermediate | Intermediate structure | MS (M + H)+ |
|---|---|---|
| A-10 | 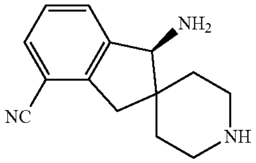 [SMILES: N#Cc1cccc2c1CC1(CCNCC1)[C@@H]2N] | 228 |
| A-11 | 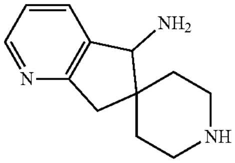 [SMILES: NC1c2cccnc2CC12CCNCC2] | 204 |
| A-12 | 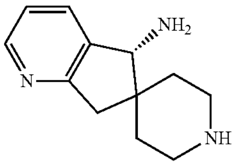 [SMILES: N[C@H]1c2cccnc2CC12CCNCC2] | 204 |
| A-13 | 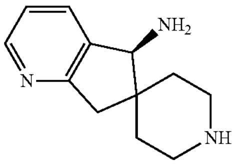 [SMILES: N[C@@H]1c2cccnc2CC12CCNCC2] | 204 |
| A-14 | 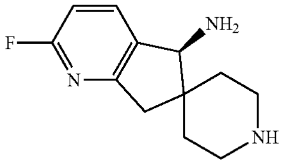 [SMILES: N[C@@H]1c2ccc(F)nc2CC12CCNCC2] | 222 |
| A-15 | 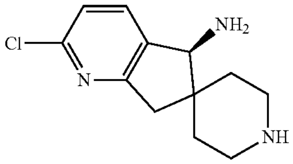 [SMILES: N[C@@H]1c2ccc(Cl)nc2CC12CCNCC2] | 238 |
| A-16 | 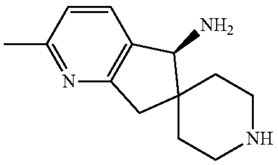 [SMILES: Cc1ccc2c(n1)CC1(CCNCC1)[C@@H]2N] | 218 |
| A-17 | 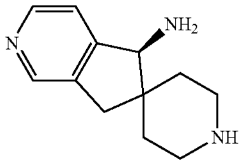 [SMILES: N[C@@H]1c2ccncc2CC12CCNCC2] | 204 |
| A-18 | 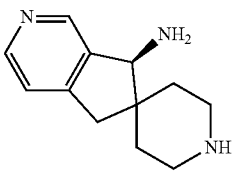 [SMILES: N[C@@H]1c2cnccc2CC12CCNCC2] | 204 |

TABLE 1-continued
| Intermediate | Intermediate structure | MS $(M + H)^+$ |
|---|---|---|
| A-19 | 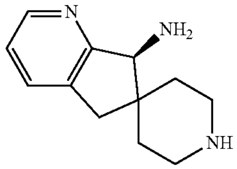 [SMILES: N[C@@H]1c2ncccc2CC12CCNCC2] | 204 |
| A-20 | 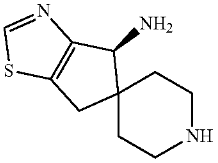 [SMILES: N[C@@H]1c2ncsc2CC12CCNCC2] | 210 |
| A-21 | 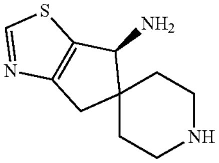 [SMILES: N[C@@H]1c2scnc2CC12CCNCC2] | 210 |
| A-22 | 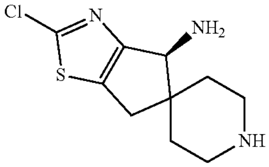 [SMILES: N[C@@H]1c2nc(Cl)sc2CC12CCNCC2] | 244 |
| A-23 | 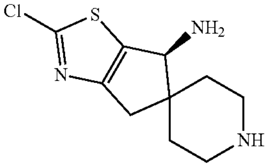 [SMILES: N[C@@H]1c2sc(Cl)nc2CC12CCNCC2] | 244 |
| A-24 | 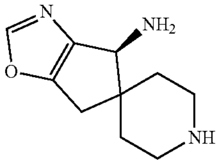 [SMILES: N[C@@H]1c2ncoc2CC12CCNCC2] | 194 |
| A-25 | 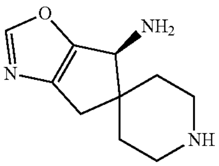 [SMILES: N[C@@H]1c2ocnc2CC12CCNCC2] | 194 |
Preparation Example 26. Synthesis of Intermediate B-1
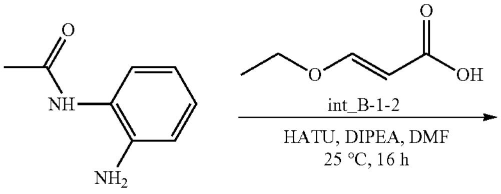
int_B-1-1
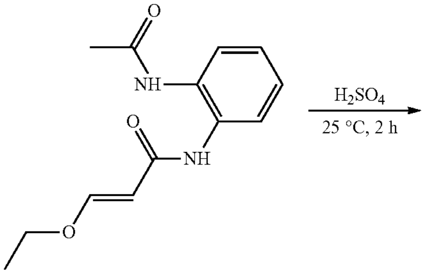
int_B-1-3
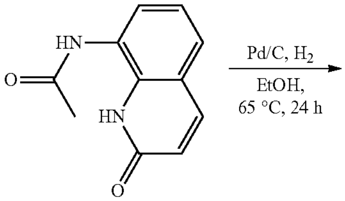
int_B-1-4
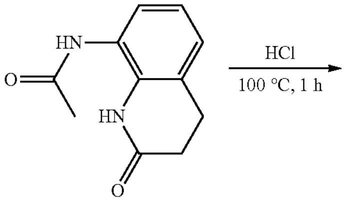
int_B-1-5
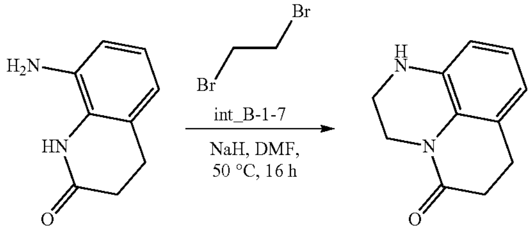
int_B-1-6
B-1

Step 1: Synthesis of Compound int_B-1-3:

int_B-1-3

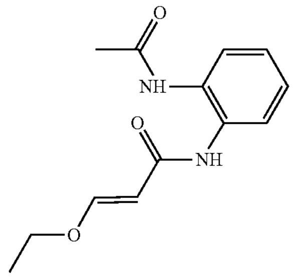

Int_B-1-1 (15.0 g, 129 mmol) was dissolved in DMF (300 mL). DIPEA (33.4 g, 258 mmol, 45.00 mL), HATU (98.2 g, 258 mmol) and int_B-1-2 (19.4 g, 129 mmol) were added. The mixture was reacted at room temperature for 16 h. LC-MS monitoring showed the reaction was completed. The reaction solution was concentrated under reduced pressure to remove the solvent. The residue was dissolved in water (50 mL). The aqueous phase was extracted with ethyl acetate (100 mL×3). The organic phase was dried over anhydrous sodium sulfate and concentrated under reduced pressure to give a crude product (19 g, 53.3% yield). The crude product was directly used in the next step.

MS (ESI): 249 $[M+H]^+$.

Step 2: Synthesis of Compound int_B-1-4:

int_B-1-4

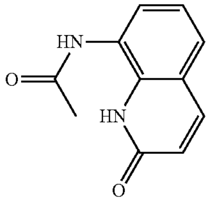

Int_B-1-3 (19.0 g, 68.9 mmol) was slowly dissolved in concentrated sulfuric acid (90 mL). The mixture was reacted at room temperature for 2 h. LC-MS monitoring showed the reaction was completed. The mixture was slowly poured into ice water, and filtered to give a solid (7 g, 49.3% yield).

MS (ESI): 203 $[M+H]^+$.

Step 3: Synthesis of Compound int_B-1-5:

int_B-1-5

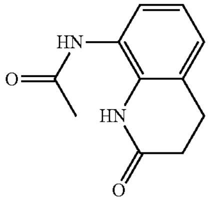

Int_B-1-4 (7.00 g, 33.9 mmol) was dissolved in ethanol (300 mL), and Pd/C (700 mg, 10%) was added. The reaction system was purged with hydrogen three times. Under hydrogen atmosphere, the mixture was heated to 65 °C and reacted for 24 h. LC-MS monitoring showed the reaction was completed. The solvent was removed by concentration under reduced pressure to give a crude product (4.8 g, 67.9% yield). The crude product was directly used in the next step.

MS (ESI): 205 $[M+H]^+$.

Step 4: Synthesis of Compound int_B-1-6:

int_B-1-6

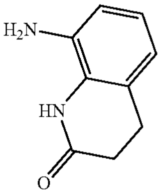

Int_B-1-5 (4.50 g, 22.0 mmol) was dissolved in 20% hydrochloric acid (45 mL), and Pd/C (700 mg, 10%) was added. The mixture was heated to 100 °C and reacted for 3 h. LC-MS monitoring showed the reaction was completed. The reaction solution was poured into ice water, and the pH was adjusted to 10. A precipitate was produced. The mixture was filtered to give a solid (2.05 g, 56.2% yield).

MS (ESI): 163 $[M+H]^+$.

Step 4: Synthesis of Compound B-1:

B-1

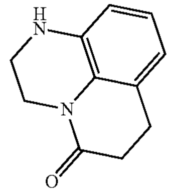

Int_B-1-6 (0.4 g, 2.47 mmol) was dissolved in DMF (40 mL). NaH (591.85 mg, 14.80 mmol, 60% purity) and int_B-1-7 (2.32 g, 12.33 mmol, 930.35 μL) were added at 0 °C under nitrogen atmosphere. The mixture was reacted at room temperature for 16 h. LC-MS monitoring showed the reaction was completed. The solvent was removed by concentration under reduced pressure to give a crude product. The crude product was diluted with water (30 mL). The aqueous phase was extracted with ethyl acetate (30 mL×3), and the organic phase was dried over anhydrous sodium sulfate. The organic phase was concentrated under reduced pressure to give a crude product. The crude product was purified by preparative column chromatography (ISCO©; 5 g Sepa Flash® Silica Flash Column, Eluent of 0-10% DCM/MeOH, gradient @50 mL/min) to give a white solid (110 mg, 21.3% yield).

$^1H$ NMR (400 MHz, DMSO-d6) δ=6.75-6.70 (m, 1H), 6.50 (d, J=7.6 Hz, 1H), 6.42 (d, J=7.3 Hz, 1H), 5.95 (br s, 1H), 3.79-3.74 (m, 2H), 3.21-3.17 (m, 2H), 2.79-2.74 (m, 2H), 2.48 (br s, 2H).

MS (ESI): 189 $[M+H]^+$.

Preparation Example 27. Synthesis of Intermediate R-7

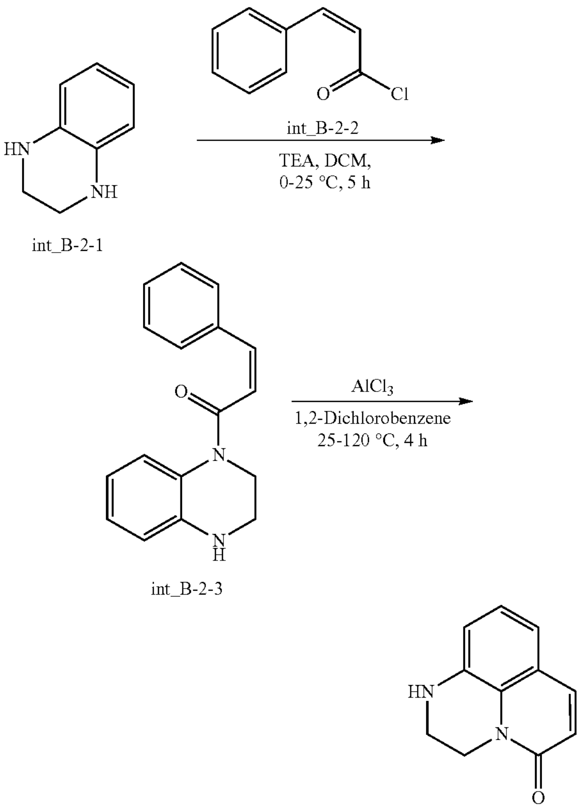

Step 1: Synthesis of Compound int_B-2-3:

int_B-2-3

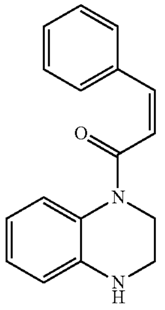

Int_B-2-1 (5.00 g, 37.3 mmol) was dissolved in DCM (50 mL) at 0 °C. The reaction solution was incubated at 0 °C, and int_B-2-2 (6.52 g, 39.1 mmol, 5.62 mL) was added slowly. The mixture was reacted at room temperature for 5 h. LC-MS monitoring showed the reaction was completed. The reaction solution was diluted with water (25 mL), and the aqueous phase was extracted with DCM (100 mL×3). The organic phase was dried over anhydrous sodium sulfate, and concentrated under reduced pressure to give a crude product. The crude product was purified by preparative column chromatography (ISCO®; 5 g Sepa Flash® Silica Flash Column, Eluent of 0-50% Ethyl acetate/Petroleum ether, gradient @50 mL/min) to give a white solid (4 g, 40.6% yield).

MS (ESI): 265 [M+H]+.

Step 2: Synthesis of Compound B-2:

B-2

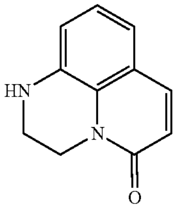

Int_B-2-3 (5.60 g, 21.1 mmol) was dissolved in 1,2-dichlorobenzene (100 mL). $AlCl_3$ (26.6 g, 199 mmol) was added at room temperature, and the mixture was reacted at 120 °C for 4 h. LC-MS monitoring showed the reaction was completed. The reaction solution was diluted with water (100 mL). The pH of the aqueous phase was adjusted to 8 with an aqueous sodium hydroxide solution. The aqueous phase was extracted with DCM (100 mL×3). The organic phase was dried over anhydrous sodium sulfate, and concentrated under reduced pressure to give a crude product. The crude product was purified by preparative column chromatography (ISCO®; 5 g Sepa Flash® Silica Flash Column, Eluent of 0-100% Ethyl acetate/Petroleum ether, gradient @50 mL/min) to give a brown solid (0.5 g, 12.7% yield). $^1$H NMR (400 MHz, DMSO-d6) δ=7.82 (d, J=9.5 Hz, 1H), 7.06-6.95 (m, 2H), 6.83 (dd, J=1.3, 7.5 Hz, 1H), 6.55 (d, J=9.5 Hz, 1H), 4.05 (t, J=5.1 Hz, 2H), 3.34 (t, J=5.1 Hz, 2H).

MS (ESI): 187 [M+H]+.

Preparation Example 28. Synthesis of Intermediate B-3

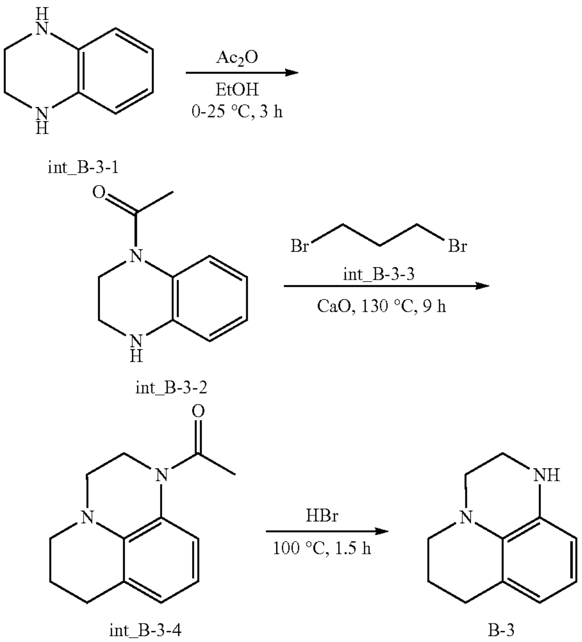

Step 1: Synthesis of Compound int_B-3-2:

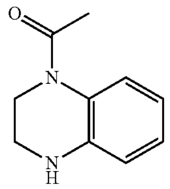

int_B-3-2

Int_B-3-1 (20.0 g, 149 mmol) was dissolved in ethanol (200 mL). The reaction solution was cooled to 0 °C, and then acetic anhydride (15.2 g, 149 mmol, 14.0 mL) was added slowly. The mixture was reacted at room temperature for 3 h. LC-MS monitoring showed the reaction was completed. The reaction solution was diluted with water (100 mL), and the aqueous phase was extracted with DCM (200 mL×3). The organic phase was dried over anhydrous sodium sulfate, and concentrated under reduced pressure to give a crude product (20 g, 76.1% yield), which was directly used in the next step.

MS (ESI): 177 $[M+H]^+$.

Step 2: Synthesis of Compound int_B-3-4:

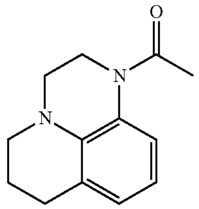

int_B-3-4

Int_B-3-2 (22.0 g, 125 mmol) and calcium oxide (18.9 g, 337 mmol) were dissolved in 1,3-dibromopropane (120 mL). The mixture was reacted at 130 °C for 9 h under nitrogen atmosphere. LC-MS monitoring showed the reaction was completed. The reaction solution was diluted with water (50 mL), and the aqueous phase was extracted with ethyl acetate (100 mL×3). The organic phase was dried over anhydrous sodium sulfate, and concentrated under reduced pressure to give a crude product. The crude product was purified by preparative column chromatography (SiO2, Ethyl acetate/Petroleum ether=0/1-3/10) to give a yellow oil (11 g, 40.7% yield).

$^1$H NMR (400 MHz, CHLOROFORM-d) δ=6.80 (br d, J=7.3 Hz, 2H), 6.50 (t, J=7.7 Hz, 1H), 3.89 (br t, J=5.4 Hz, 2H), 3.30 (t, J=5.5 Hz, 2H), 3.24 (t, J=5.8 Hz, 2H), 2.77 (t, J=6.3 Hz, 2H), 2.26-2.22 (m, 3H), 2.01-1.94 (m, 2H).

MS (ESI): 217 $[M+H]^+$.

Step 3: Synthesis of Compound B-3:

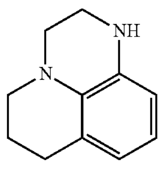

B-3

Int_B-3-4 (2.50 g, 11.6 mmol) was dissolved in an aqueous HBr solution (120 mL). The mixture was reacted at 100 °C for 1.5 h under nitrogen atmosphere. LC-MS monitoring showed the reaction was completed. The solvent was removed by concentration under increased pressure. The reaction solution was diluted with a 10% aqueous sodium hydroxide solution (10 mL), and the aqueous phase was extracted with ethyl acetate (30 mL×3). The organic phase was dried over anhydrous sodium sulfate, and concentrated under reduced pressure to give a crude product (1.7 g, 84.4% yield), which was directly used in the next step.

$^1$H NMR (400 MHz, DMSO-d6) δ=6.31 (br s, 1H), 6.20-6.11 (m, 2H), 5.37 (br s, 1H), 3.32 (br s, 2H), 3.00 (br s, 4H), 2.62 (t, J=6.5 Hz, 2H), 1.94-1.83 (m, 2H).

MS (ESI): 175 $[M+H]^+$.

Preparation Examples 29-32. Synthesis of Intermediates B-4 to B-7

The target intermediates B-4 to B-7 in Table 2 were obtained by the synthesis methods described above using different starting materials.

TABLE 2

| Intermediate | Intermediate structure | MS $(M + H)^+$ |
|---|---|---|
| B-4 | 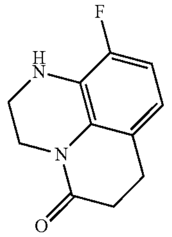 [SMILES: O=C1CCc2ccc(F)c3c2N1CCN3] | 207 |
| B-5 | 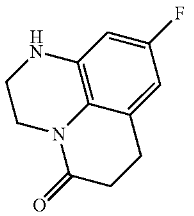 [SMILES: O=C1CCc2cc(F)cc3c2N1CCN3] | 207 |
| B-6 | 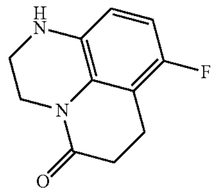 [SMILES: O=C1CCc2c(F)ccc3c2N1CCN3] | 207 |
| B-7 | 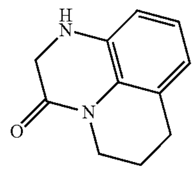 [SMILES: O=C1CNc2cccc3c2N1CCC3] | 189 |

Example 1. Synthesis of Compound 1

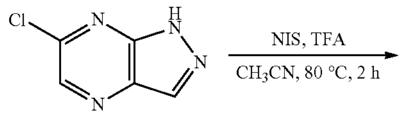

int_1-1

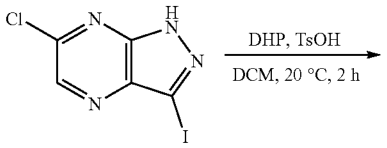

int_1-2

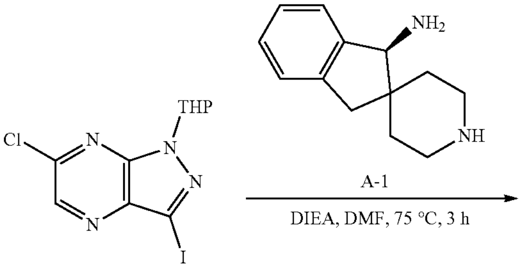

int_1-3

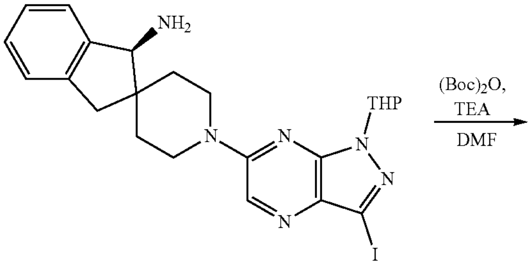

int_1-4

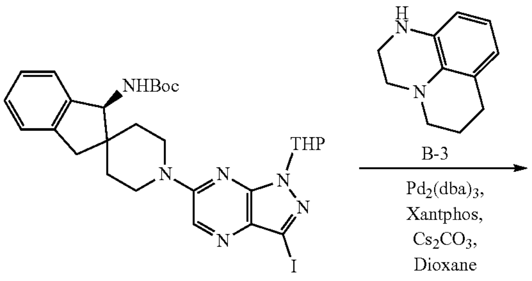

int_1-5

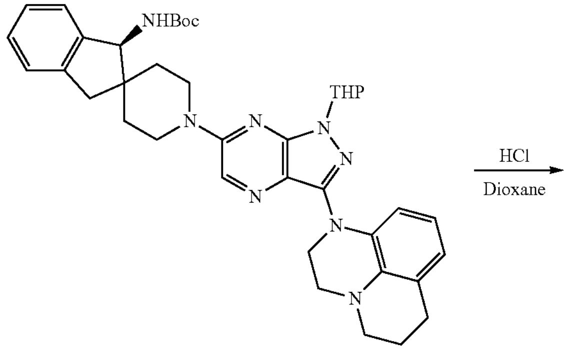

int_1-6

-continued

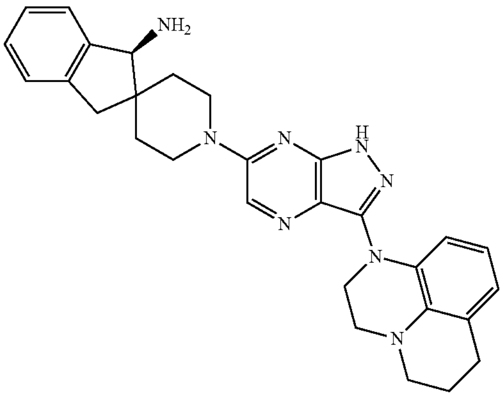

1

Step 1: Synthesis of Compound int_1-2:

int_1-2

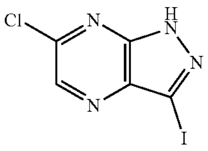

Int_1-1 (2 g, 12.94 mmol) and NIS (5.82 g, 25.88 mmol) were dissolved in acetonitrile (50 mL). Trifluoroacetic acid (4.42 g, 38.82 mmol) was added at room temperature. The mixture was heated to 80 °C and reacted for 2 h. LC-MS monitoring showed the reaction was completed. The reaction solution was cooled to room temperature and filtered. The filter cake was collected and dried to give a product (3.1 g, 85.42% yield).

MS (ESI): 281 $[M+H]^+$.

Step 2: Synthesis of Compound int_1-3:

int_1-3

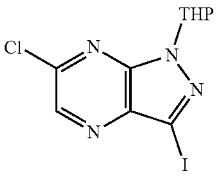

Int_1-2 (3.1 g, 11.05 mmol) and TsOH (951.72 mg, 5.53 mmol) were dissolved in DCM (50 mL). DHP (1.12 g, 13.26 mmol, 1.21 mq) was added at 0 °C. The mixture was reacted at room temperature for 2 h. LC-MS monitoring showed the reaction was completed. The mixture was concentrated directly. The residue was subjected to column chromatography ($SiO_2$, Petroleum ether/Ethyl acetate=10:1) to give a white solid (2.3 g, 57.1% yield).

$^1H$ NMR: (400 MHz, CHLOROFORM-d) δ=8.62-8.55 (m, 1H), 5.99 (dd, J=2.5, 10.3 Hz, 1H), 4.19-4.10 (m, 1H), 3.82 (dt, J=2.6, 11.5 Hz, 1H), 2.75-2.59 (m, 1H), 2.24-2.14 (m, 1H), 2.00 (br dd, J=2.5, 13.1 Hz, 1H), 1.90-1.74 (m, 2H), 1.67 (br dd, J=4.1, 7.7 Hz, 1H).

Step 3: Synthesis of Compound int_1-4:

int_1-4

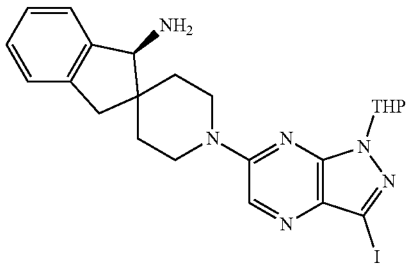

Int_1-3 (1.97 g, 5.39 mmol) and A-1 (1.17 g, 4.90 mmol) were dissolved in DMF (30 mL).

DIPEA (3.80 g, 29.40 mmol, 5.12 mL) was added at room temperature. Under argon atmosphere, the mixture was heated to 75 °C and reacted for 3 h. LC-MS monitoring showed the reaction was completed. The filtrate was concentrated. The residue was subjected to column chromatography ($SiO_2$, Petroleum ether/Ethyl acetate=0/1) to give a yellow solid (2 g, 76.95% yield).

$^1$H NMR: (400 MHz, CHLOROFORM-d) δ=8.22 (s, 1H), 7.37 (br d, J=5.3 Hz, 1H), 7.28-7.22 (m, 3H), 5.80 (dd, J=2.5, 10.5 Hz, 1H), 4.45-4.24 (m, 2H), 4.16-3.99 (m, 2H), 3.80-3.69 (m, 1H), 3.45-3.26 (m, 2H), 3.19-3.06 (m, 1H), 2.78 (br d, J=15.8 Hz, 1H), 2.73-2.59 (m, 1H), 2.20-2.12 (m, 1H), 1.99-1.87 (m, 2H), 1.86-1.59 (m, 8H), 1.50-1.42 (m, 1H).

Step 4: Synthesis of Compound int_1-5:

int_1-5

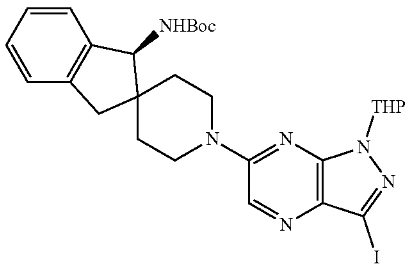

Int_1-4 (780 mg, 1.47 mmol) was dissolved in DMF (5 mL). TEA (298 mg, 2.94 mmol) and $Boc_2O$ (321 mg, 1.47 mmol) were added. The mixture was reacted at room temperature overnight. LC-MS monitoring showed the reaction was completed. The reaction solution was concentrated to dryness by rotary evaporation to give a crude product. The crude product was subjected to column chromatography to give a product (785 mg, 84.6% yield).

MS (ESI): 631 $[M+H]^+$.

Step 5: Synthesis of Compound int_1-6:

int_1-6

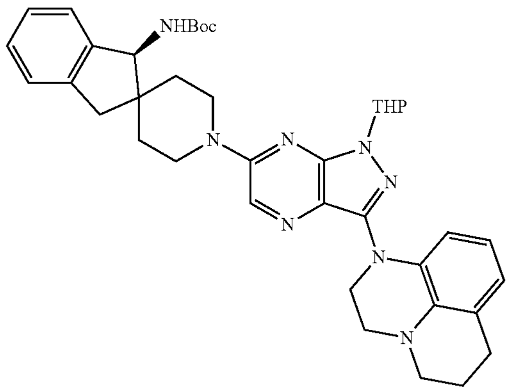

Int_1-5 (63 mg, 0.1 mmol) was dissolved in dioxane (5 mL). B-3 (17.4 mg, 0.1 mmol), $Pd_2(dba)_3$ (9 mg, 0.01 mmol), Xantphos (6 mg, 0.01 mmol) and cesium carbonate (49 mg, 0.15 mmol) were added. Under nitrogen atmosphere, the reaction solution was heated to 100 °C and reacted overnight. LC-MS monitoring showed the reaction was completed. The reaction solution was concentrated to dryness by rotary evaporation under reduced pressure. The residue was subjected to silica gel column chromatography to give a product (40 mg, 59.1% yield).

MS (ESI): 677 $[M+H]^+$.

Step 6: Synthesis of Compound 1:

1

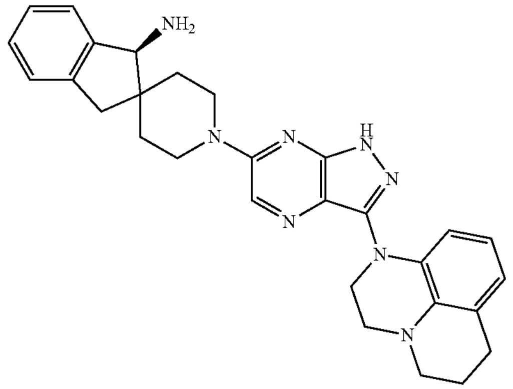

Int_1-6 (40 mg, 0.059 mmol) was dissolved in ethyl acetate (2 mL). A solution of hydrochloric acid in dioxane (4 M, 2 mL) was added. The mixture was reacted at room temperature for 3 h under nitrogen atmosphere. LC-MS monitoring showed the reaction was completed. The reaction solution was concentrated to dryness by rotary evaporation under reduced pressure.

The residue was subjected to silica gel column chromatography to give a product (15 mg, 51.7% yield).

$^1$H NMR (400 MHz, Methanol-d4) δ 8.52 (s, 1H), 8.17 (s, 1H), 7.45 (d, J=7.3 Hz, 1H), 7.38-7.24 (m, 3H), 6.67 (dd, J=8.1, 1.4 Hz, 1H), 6.54-6.46 (m, 1H), 6.38 (t, J=7.7 Hz, 1H), 4.41 (dd, J=29.8, 13.8 Hz, 2H), 4.25 (s, 2H), 4.05-3.96 (m, 2H), 3.51-3.35 (m, 2H), 3.22-3.15 (m, 2H), 3.15-3.02 (m, 2H), 2.77 (t, J=6.5 Hz, 2H), 2.02 (dt, J=11.5, 6.3 Hz, 2H), 1.84 (q, J=9.7 Hz, 3H), 1.65 (s, 2H).

MS (ESI): 493 $[M+H]^+$.

Example 2. Synthesis of Compound 3

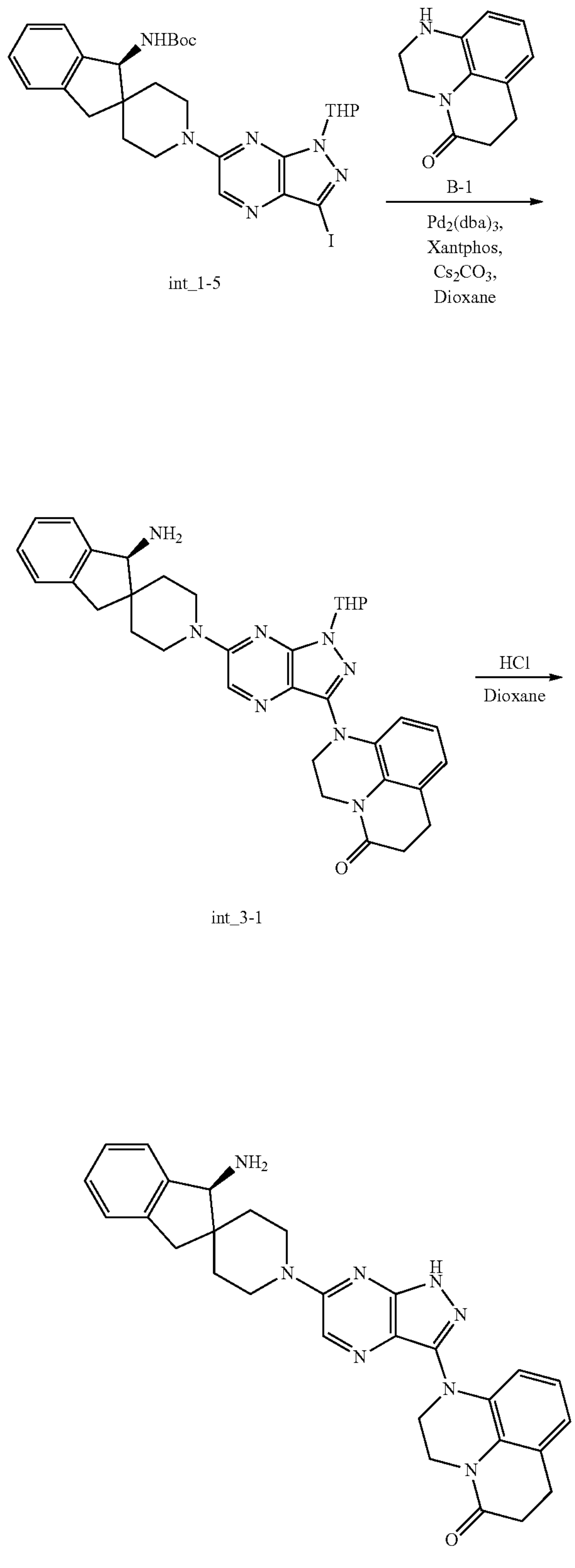

int_1-5 int_3-1

3

Step 1: Synthesis of Compound int_3-1:

int_3-1

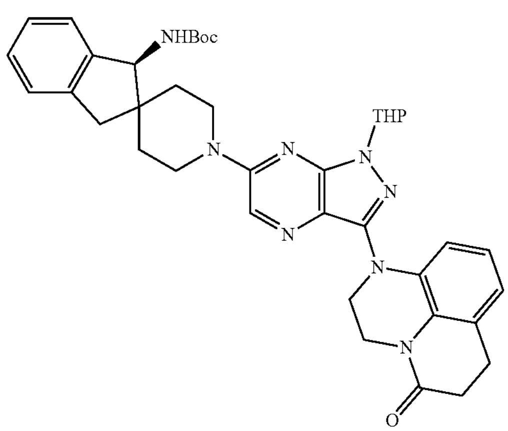

Int_1-5 (911 mg, 1.44 mmol) was dissolved in dioxane (20 mL). B-1 (272 mg, 1.44 mmol), $Pd_2(dba)_3$ (131 mg, 0.14 mmol), Xantphos (83 mg, 0.14 mmol) and cesium carbonate (706 mg, 2.16 mmol) were added. Under nitrogen atmosphere, the reaction solution was heated to 100 °C and reacted overnight. LC-MS monitoring showed the reaction was completed. The reaction solution was concentrated to dryness by rotary evaporation under reduced pressure. The residue was subjected to silica gel column chromatography to give a product (850 mg, 85.2% yield).

MS (ESI): 691 $[M+H]^+$.

Step 2: Synthesis of Compound 3:

3

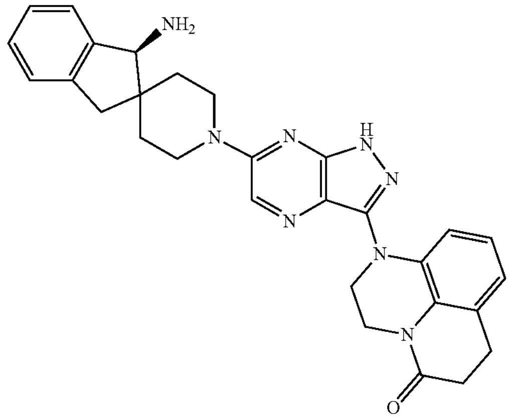

Int_3-1 (850 mg, 1.23 mmol) was dissolved in ethyl acetate (10 mL). A solution of hydrochloric acid in dioxane (4 M, 10 mL) was added. The mixture was reacted at room temperature for 3 h under nitrogen atmosphere. LC-MS monitoring showed the reaction was completed. The reaction solution was concentrated to dryness by rotary evaporation under reduced pressure. The residue was subjected to silica gel column chromatography to give a product (380 mg, 61% yield).

$^1H$ NMR (400 MHz, CHLOROFORM-d) δ 8.13 (s, 1H), 7.33 (d, J=5.8 Hz, 1H), 7.24 (d, J=14.2 Hz, 6H), 6.87 (t, J=7.8 Hz, 1H), 6.75 (d, J=7.1 Hz, 1H), 4.29 (dd, J=12.9, 7.1 Hz, 2H), 4.17-4.05 (m, 4H), 4.00 (s, 1H), 3.39-3.25 (m, 2H), 3.11 (d, J=15.6 Hz, 1H), 2.94 (t, J=7.4 Hz, 2H), 2.79-2.67 (m, 3H), 1.94-1.78 (m, 2H), 1.28 (d, J=21.6 Hz, 2H).

MS (ESI): 507 $[M+H]^+$.

Example 3. Synthesis of Compound 6

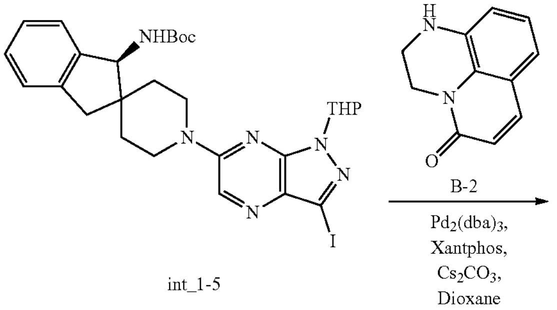

int_1-5

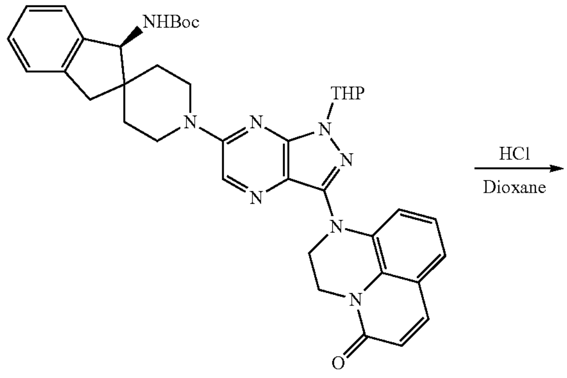

int_6-1

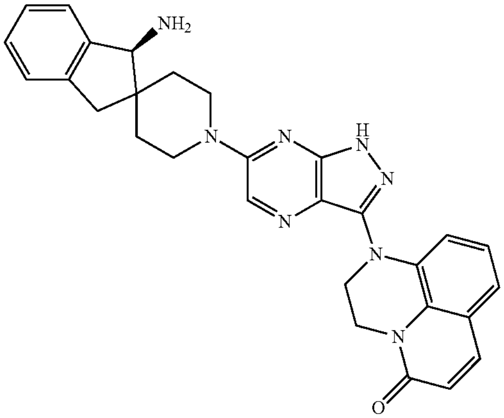

6

Step 1: Synthesis of compound int_6-1:

int_6-1

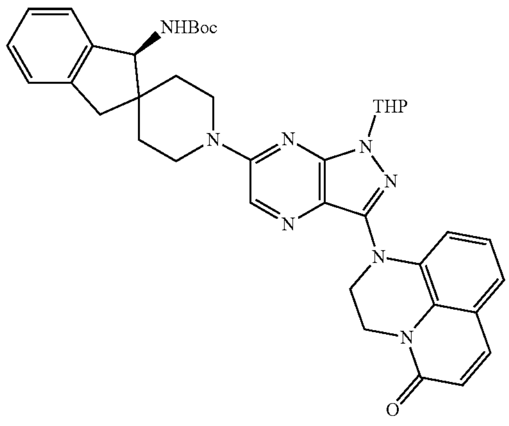

Int_1-5 (630 mg, 1.0 mmol) was dissolved in dioxane (20 mL). B-2 (190 mg, 1.0 mmol), $Pd_2(dba)_3$ (91 mg, 0.1 mmol), Xantphos (58 mg, 0.1 mmol) and cesium carbonate (490 mg, 1.5 mmol) were added. Under nitrogen atmosphere, the reaction solution was heated to 100 °C and reacted overnight. LC-MS monitoring showed the reaction was completed. The reaction solution was concentrated to dryness by rotary evaporation under reduced pressure. The residue was subjected to silica gel column chromatography to give a product (600 mg, 87.1% yield).

MS (ESI): 689 $[M+H]^+$.

Step 2: Synthesis of Compound 6:

6

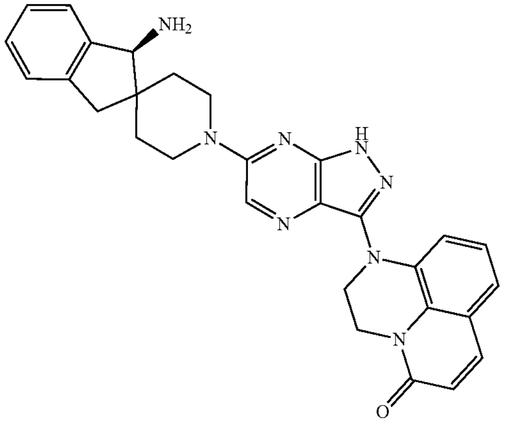

Int_6-1 (700 mg, 1.02 mmol) was dissolved in ethyl acetate (10 mL). A solution of hydrochloric acid in dioxane (4 M, 10 mL) was added. The mixture was reacted at room temperature for 3 h under nitrogen atmosphere. LC-MS monitoring showed the reaction was completed. The reaction solution was concentrated to dryness by rotary evaporation under reduced pressure. The residue was subjected to silica gel column chromatography to give a product (375 mg, 74.3% yield).

$^1H$ NMR (400 MHz, DMSO-d6) δ 12.64 (s, 1H), 8.34 (s, 1H), 7.91 (d, J=9.5 Hz, 1H), 7.49 (d, J=7.2 Hz, 1H), 7.38 (d, J=8.1 Hz, 1H), 7.35-7.18 (m, 4H), 7.05 (t, J=7.9 Hz, 1H), 6.62 (d, J=9.5 Hz, 1H), 4.35 (dd, J=22.1, 14.2 Hz, 2H), 4.27-4.04 (m, 3H), 3.24-3.06 (m, 5H), 2.92 (d, J=16.1 Hz, 1H), 1.78 (ddd, J=21.5, 13.6, 6.4 Hz, 2H), 1.49 (dd, J=28.6, 13.3 Hz, 2H).

MS (ESI): 505 $[M+H]^+$.

Example 4. Synthesis of Compound 12

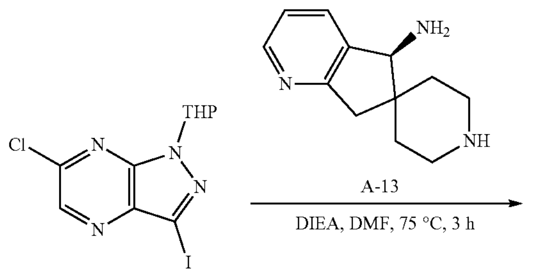

int_1-3

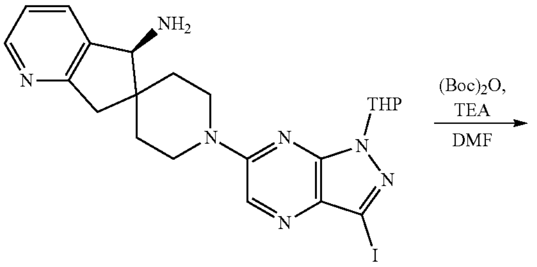

int_12-1

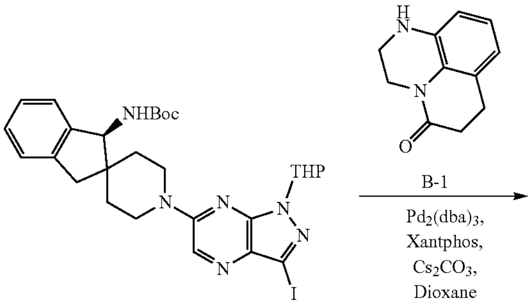

int_12-2

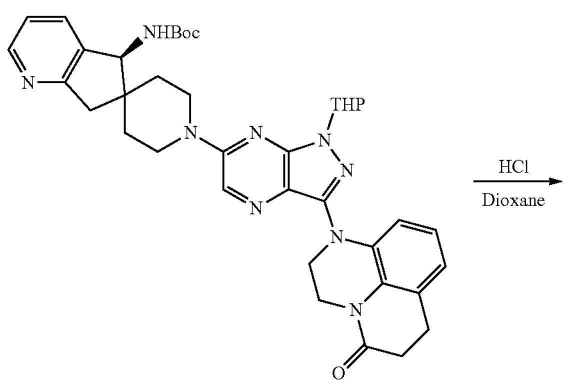

int_12-3

-continued

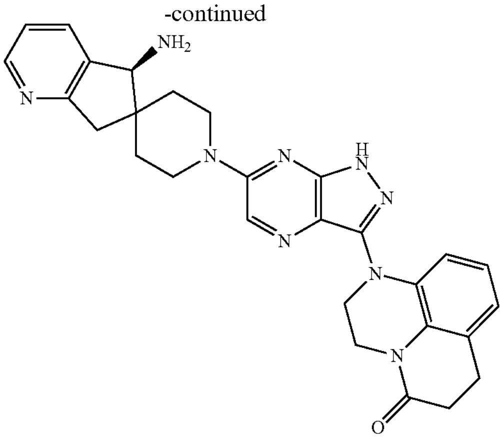

12

Step 1: Synthesis of Compound int_12-1:

int_12-1

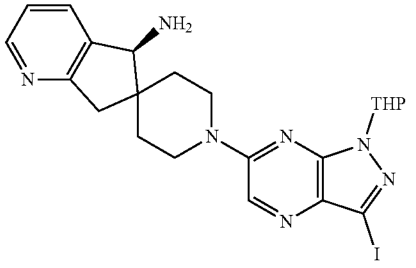

Int_1-3 (2 g, 5.39 mmol) and A-13 (1.2 g, 4.90 mmol) were dissolved in DMF (30 mL). DIPEA (3.80 g, 29.40 mmol, 5.12 mL) was added at room temperature. Under argon atmosphere, the mixture was heated to 75 °C and reacted for 3 h. LC-MS monitoring showed the reaction was completed. The filtrate was concentrated. The residue was subjected to column chromatography ($SiO_2$, Petroleum ether/Ethyl acetate=0/1) to give a yellow solid (2.3 g, 88% yield).

MS (ESI): 532 $[M+H]^+$.

Step 2: Synthesis of Compound int_12-2:

int_12-2

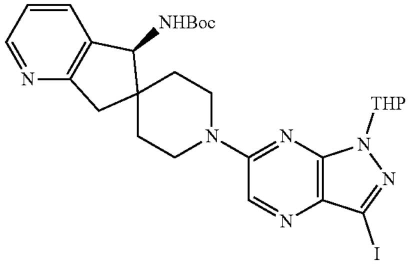

Int_12-1 (800 mg, 1.5 mmol) was dissolved in DMF (5 mL). TEA (298 mg, 2.94 mmol) and $Boc_2O$ (321 mg, 1.47 mmol) were added. The mixture was reacted at room temperature overnight. LC-MS monitoring showed the reaction was completed. The reaction solution was concentrated to dryness by rotary evaporation to give a crude product. The crude product was subjected to column chromatography to give a product (750 mg, 79% yield).

MS (ESI): 632 $[M+H]^+$.

Step 3: Synthesis of Compound int_12-3:

int_12-3

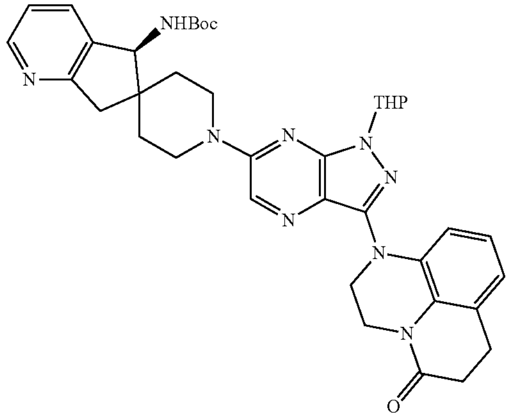

Int_12-2 (65 mg, 0.1 mmol) was dissolved in dioxane (5 mL). B-1 (18 mg, 0.1 mmol), $Pd_2(dba)_3$ (9 mg, 0.01 mmol), Xantphos (6 mg, 0.01 mmol) and cesium carbonate (49 mg, 0.15 mmol) were added. Under nitrogen atmosphere, the reaction solution was heated to 100 °C and reacted overnight. LC-MS monitoring showed the reaction was completed. The reaction solution was concentrated to dryness by rotary evaporation under reduced pressure. The residue was subjected to silica gel column chromatography to give a product (38 mg, 55% yield).

MS (ESI): 692 $[M+H]^+$.

Step 4: Synthesis of Compound 12:

12

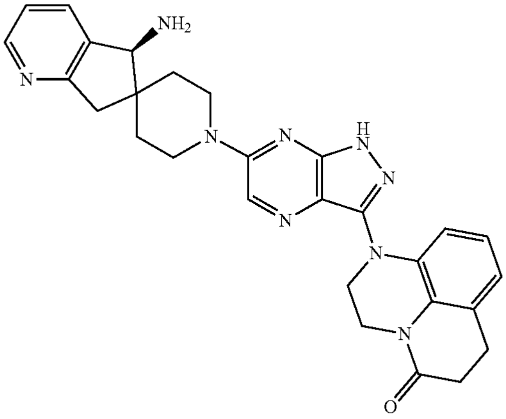

Int_12-3 (35 mg, 0.05 mmol) was dissolved in ethyl acetate (2 mL). A solution of hydrochloric acid in dioxane (4 M, 2 mL) was added. The mixture was reacted at room temperature for 3 h under nitrogen atmosphere. LC-MS monitoring showed the reaction was completed. The reaction solution was concentrated to dryness by rotary evaporation under reduced pressure. The residue was subjected to silica gel column chromatography to give a product (18 mg, 71% yield).

$^1$H NMR (400 MHz, CHLOROFORM-d) δ 8.43 (d, J=5.0 Hz, 1H), 8.13 (s, 1H), 7.65 (d, J=7.6 Hz, 1H), 7.22 (d, J=8.3 Hz, 1H), 7.15 (t, J=6.4 Hz, 1H), 6.86 (t, J=7.8 Hz, 1H), 6.74 (d, J=7.3 Hz, 1H), 4.34 (d, J=13.7 Hz, 2H), 4.10 (q, J=6.7, 4.9 Hz, 4H), 4.04 (s, 1H), 3.26 (dd, J=22.5, 12.8 Hz, 3H), 2.97-2.86 (m, 3H), 2.69 (t, J=7.4 Hz, 2H), 2.06 (s, 1H), 2.00 (s, 2H), 1.95-1.88 (m, 1H), 1.67 (d, J=13.6 Hz, 1H), 1.41 (d, J=12.6 Hz, 1H).

MS (ESI): 508 $[M+H]^+$.

Examples 5-49. Synthesis of Compound 2, Compounds 4-5, Compounds 7-11 and Compounds 13-49

The target compound 2, compounds 4-5, compounds 7-11 and compounds 13-49 in Table 3 were obtained using the synthesis methods described above with different starting materials.

TABLE 3

| Compound | Compound structure | MS $(M + H)^+$ |
| --- | --- | --- |
| 2 | 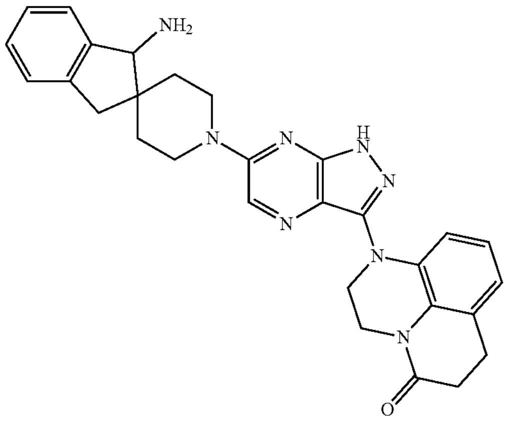 [SMILES: NC1c2ccccc2CC12CCN(c1cnc3c(N4CCN5C(=O)CCc6cccc4c65)n[nH]c3n1)CC2] | 507 |

TABLE 3-continued
| Compound | Compound structure | MS (M + H)+ |
|---|---|---|
| 4 | 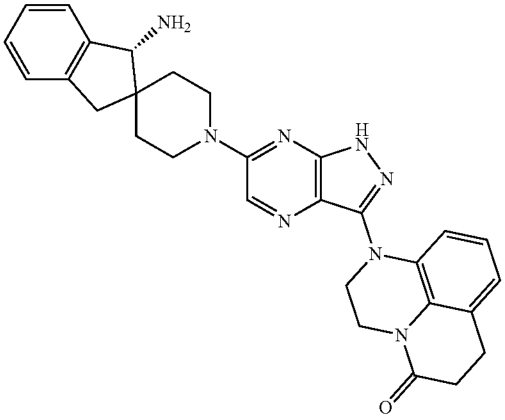 [SMILES: N[C@H]1c2ccccc2CC12CCN(c1cnc3c(N4CCN5C(=O)CCc6cccc4c65)n[nH]c3n1)CC2] | 507 |
| 5 | 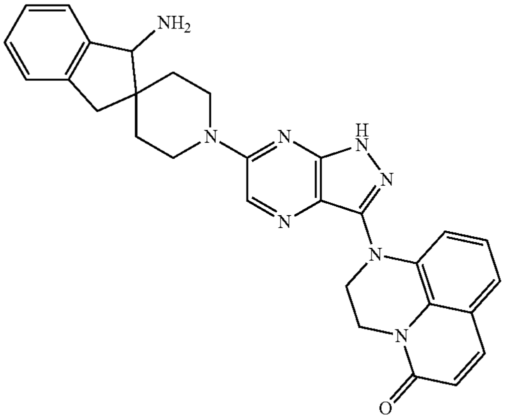 [SMILES: NC1c2ccccc2CC12CCN(c1cnc3c(N4CCn5c(=O)ccc6cccc4c65)n[nH]c3n1)CC2] | 505 |
| 7 | 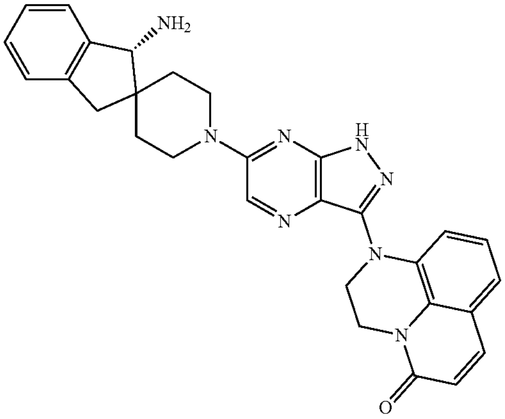 [SMILES: N[C@H]1c2ccccc2CC12CCN(c1cnc3c(N4CCn5c(=O)ccc6cccc4c65)n[nH]c3n1)CC2] | 505 |

TABLE 3-continued
| Compound | Compound structure | MS (M + H)+ |
| --- | --- | --- |
| 8 | 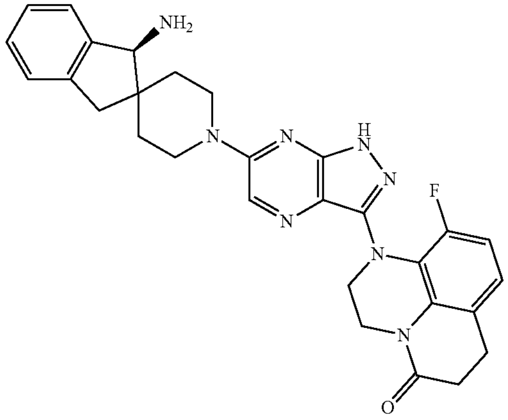 [SMILES: N[C@@H]1c2ccccc2CC12CCN(c1cnc3c(N4CCN5C(=O)CCc6ccc(F)c4c65)n[nH]c3n1)CC2] | 525 |
| 9 | 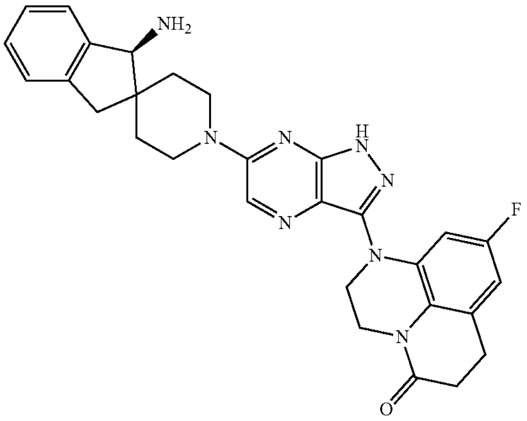 [SMILES: N[C@@H]1c2ccccc2CC12CCN(c1cnc3c(N4CCN5C(=O)CCc6cc(F)cc4c65)n[nH]c3n1)CC2] | 525 |
| 10 | 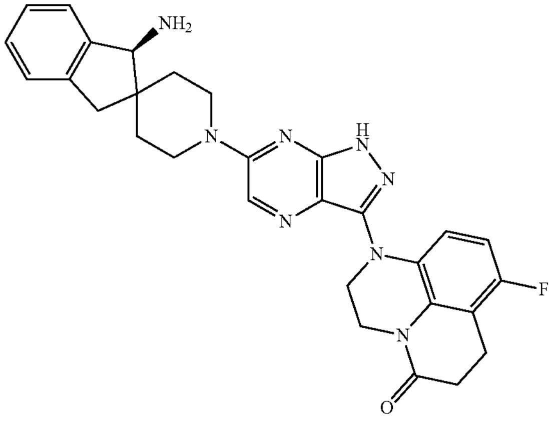 [SMILES: N[C@@H]1c2ccccc2CC12CCN(c1cnc3c(N4CCN5C(=O)CCc6c(F)ccc4c65)n[nH]c3n1)CC2] | 525 |

TABLE 3-continued
| Compound | Compound structure | MS (M + H)+ |
|---|---|---|
| 11 | 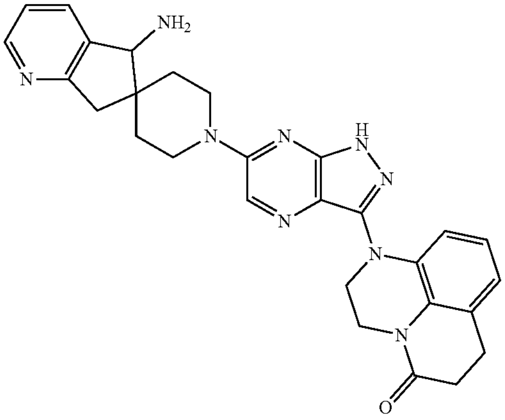 [SMILES: NC1c2cccnc2CC12CCN(c1cnc3c(N4CCN5C(=O)CCc6cccc4c65)n[nH]c3n1)CC2] | 508 |
| 13 | 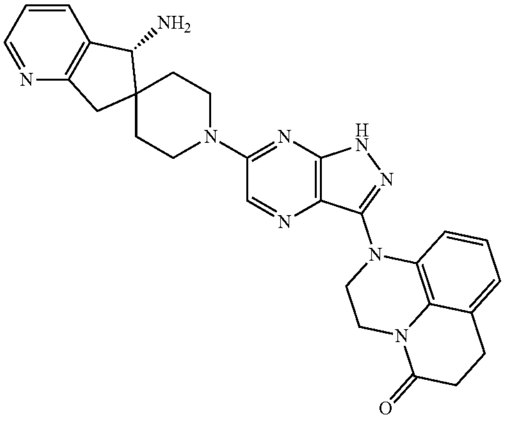 [SMILES: N[C@H]1c2cccnc2CC12CCN(c1cnc3c(N4CCN5C(=O)CCc6cccc4c65)n[nH]c3n1)CC2] | 508 |
| 14 | 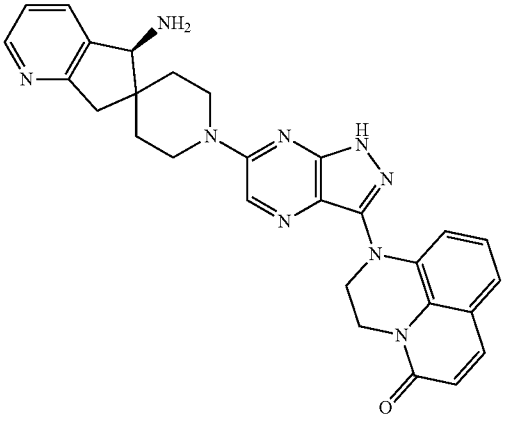 [SMILES: N[C@@H]1c2cccnc2CC12CCN(c1cnc3c(N4CCn5c(=O)ccc6cccc4c65)n[nH]c3n1)CC2] | 506 |

TABLE 3-continued
| Compound | Compound structure | MS (M + H)+ |
| --- | --- | --- |
| 15 | 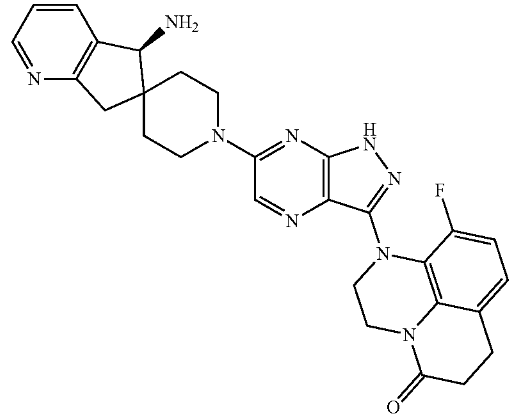 [SMILES: N[C@@H]1c2cccnc2CC12CCN(c1cnc3c(N4CCN5C(=O)CCc6ccc(F)c4c65)n[nH]c3n1)CC2] | 526 |
| 16 | 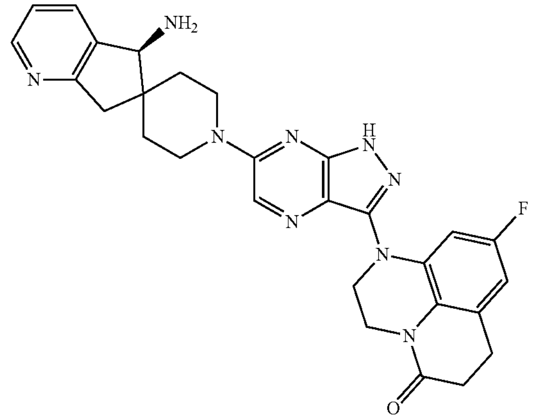 [SMILES: N[C@@H]1c2cccnc2CC12CCN(c1cnc3c(N4CCN5C(=O)CCc6cc(F)cc4c65)n[nH]c3n1)CC2] | 526 |
| 17 | 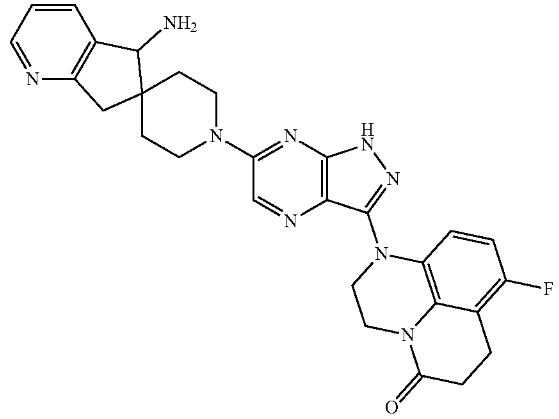 [SMILES: NC1c2cccnc2CC12CCN(c1cnc3c(N4CCN5C(=O)CCc6c(F)ccc4c65)n[nH]c3n1)CC2] | 526 |

TABLE 3-continued
| Compound | Compound structure | MS (M + H)+ |
|---|---|---|
| 18 | 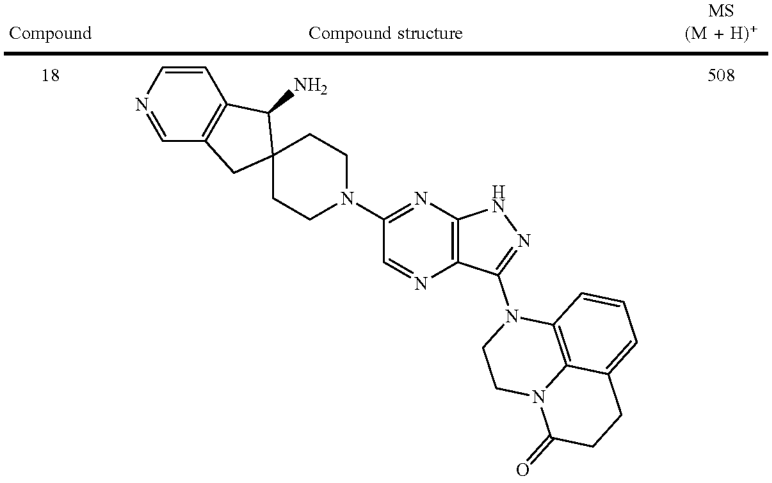 | 508 |
| 19 | 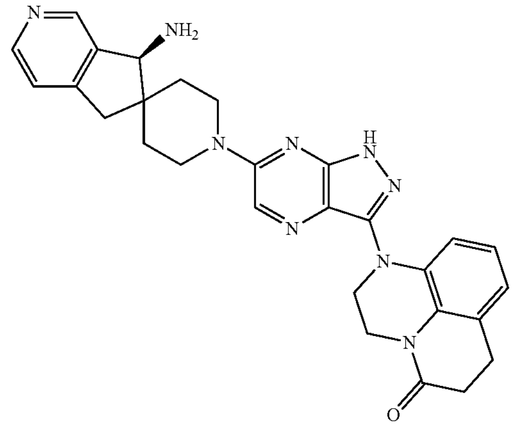 [SMILES: N[C@@H]1c2cnccc2CC12CCN(c1cnc3c(N4CCN5C(=O)CCc6cccc4c65)n[nH]c3n1)CC2] | 508 |
| 20 | 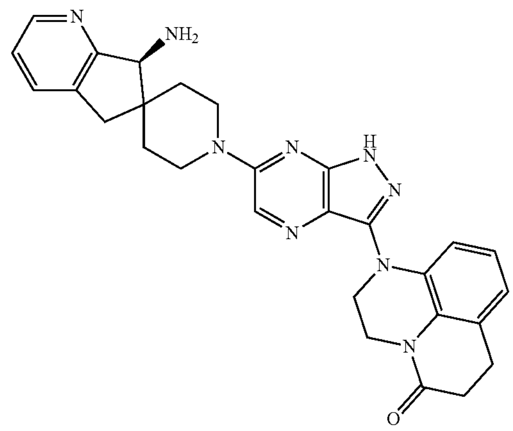 [SMILES: N[C@@H]1c2ncccc2CC12CCN(c1cnc3c(N4CCN5C(=O)CCc6cccc4c65)n[nH]c3n1)CC2] | 508 |

TABLE 3-continued
| Compound | Compound structure | MS (M + H)+ |
|---|---|---|
| 21 | 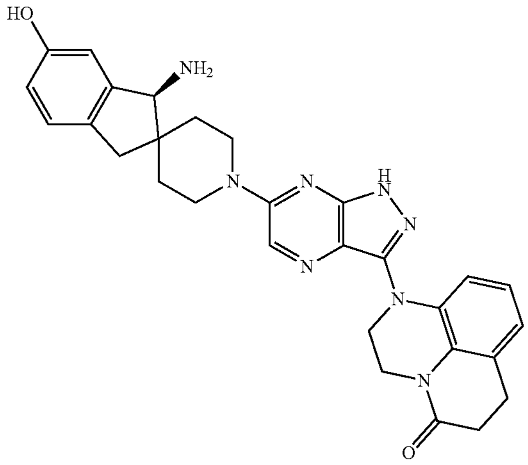 [SMILES: N[C@@H]1c2cc(O)ccc2CC12CCN(c1cnc3c(N4CCN5C(=O)CCc6cccc4c65)n[nH]c3n1)CC2] | 523 |
| 22 | 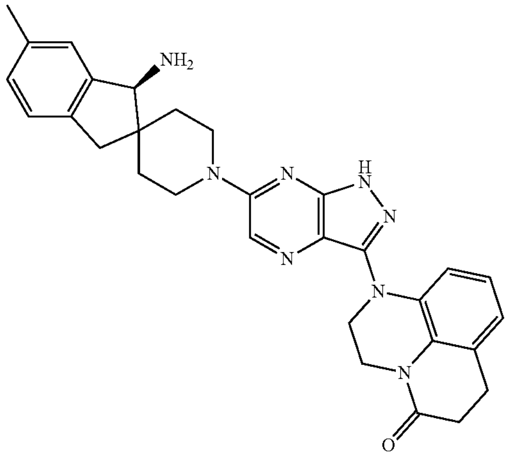 [SMILES: Cc1ccc2c(c1)[C@@H](N)C1(CCN(c3cnc4c(N5CCN6C(=O)CCc7cccc5c76)n[nH]c4n3)CC1)C2] | 521 |
| 23 | 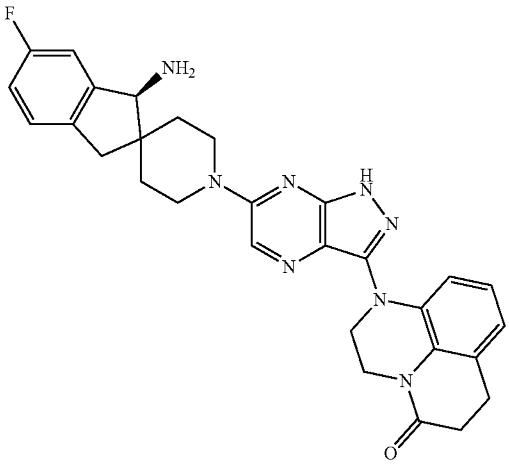 [SMILES: N[C@@H]1c2cc(F)ccc2CC12CCN(c1cnc3c(N4CCN5C(=O)CCc6cccc4c65)n[nH]c3n1)CC2] | 525 |

TABLE 3-continued
| Compound | Compound structure | MS (M + H)+ |
| --- | --- | --- |
| 24 | 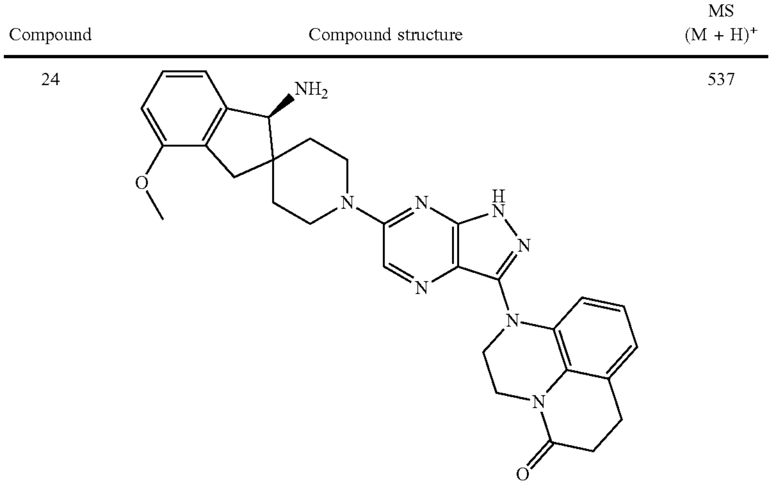 | 537 |
| 25 | 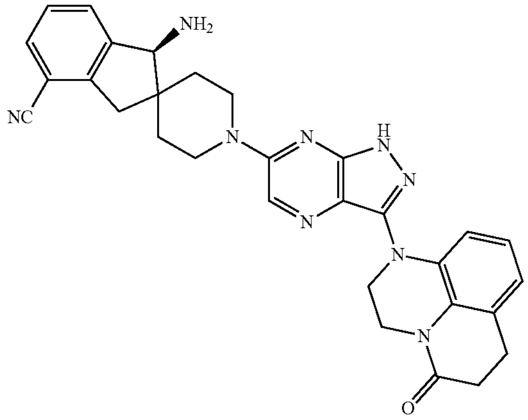 [SMILES: N#Cc1cccc2c1CC1(CCN(c3cnc4c(N5CCN6C(=O)CCc7cccc5c76)n[nH]c4n3)CC1)[C@@H]2N] | 532 |
| 26 | 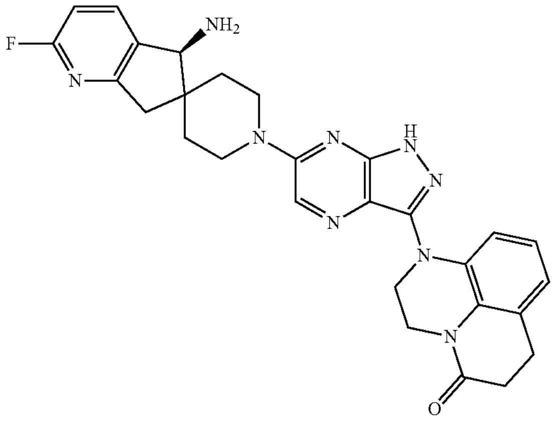 [SMILES: N[C@@H]1c2ccc(F)nc2CC12CCN(c1cnc3c(N4CCN5C(=O)CCc6cccc4c65)n[nH]c3n1)CC2] | 526 |

TABLE 3-continued
| Compound | Compound structure | MS (M + H)+ |
| --- | --- | --- |
| 27 | 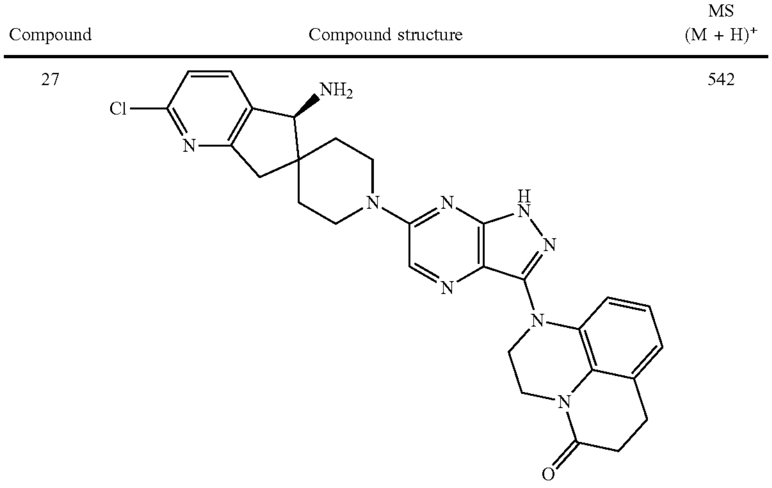 | 542 |
| 28 | 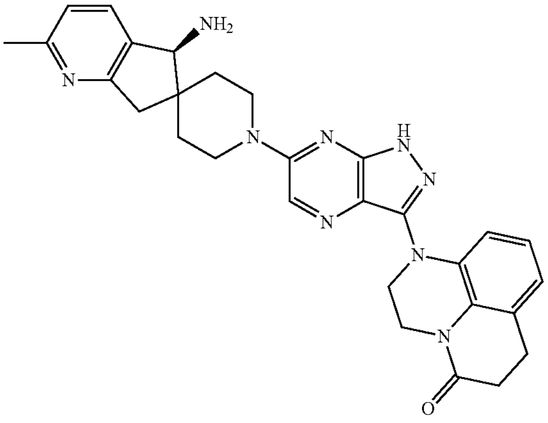 [SMILES: Cc1ccc2c(n1)CC1(CCN(c3cnc4c(N5CCN6C(=O)CCc7cccc5c76)n[nH]c4n3)CC1)[C@@H]2N] | 522 |
| 29 | 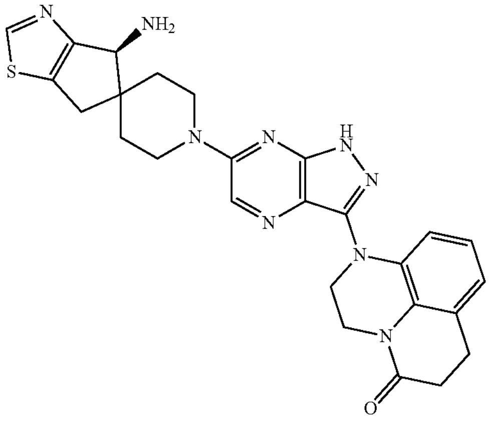 [SMILES: N[C@@H]1c2ncsc2CC12CCN(c1cnc3c(N4CCN5C(=O)CCc6cccc4c65)n[nH]c3n1)CC2] | 514 |

TABLE 3-continued
| Compound | Compound structure | MS (M + H)$^+$ |
|---|---|---|
| 30 | 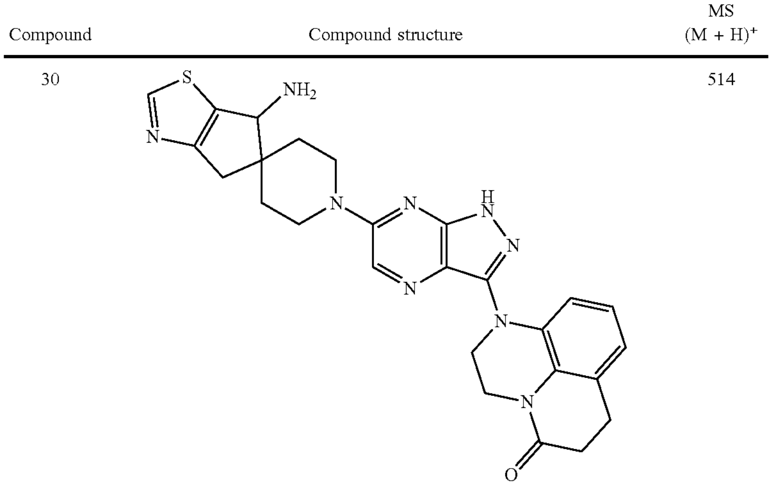 | 514 |
| 31 | 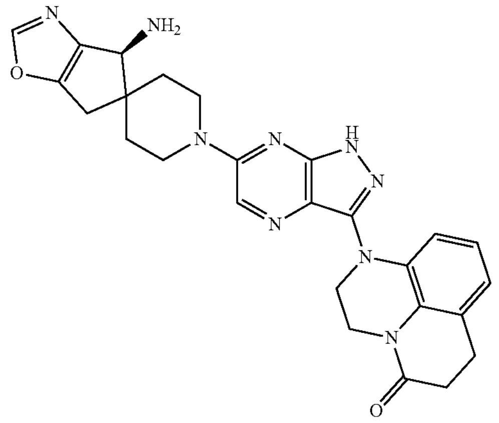 [SMILES: N[C@@H]1c2ncoc2CC12CCN(c1cnc3c(N4CCN5C(=O)CCc6cccc4c65)n[nH]c3n1)CC2] | 498 |
| 32 | 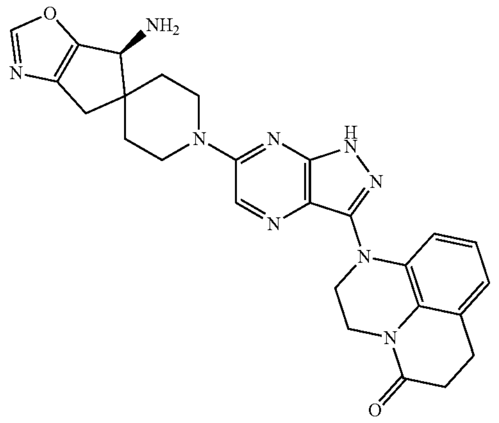 [SMILES: N[C@@H]1c2ocnc2CC12CCN(c1cnc3c(N4CCN5C(=O)CCc6cccc4c65)n[nH]c3n1)CC2] | 498 |

TABLE 3-continued
| Compound | Compound structure | MS $(M + H)^+$ |
|---|---|---|
| 33 | 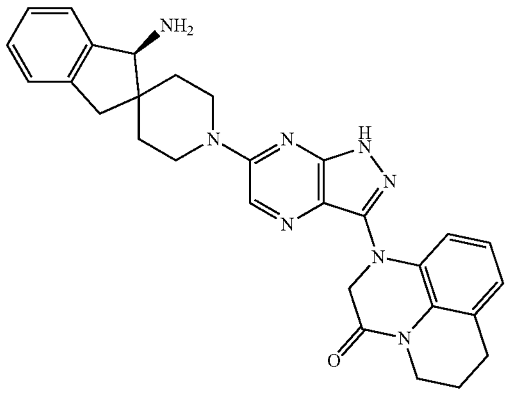 [SMILES: N[C@@H]1c2ccccc2CC12CCN(c1cnc3c(N4CC(=O)N5CCCc6cccc4c65)n[nH]c3n1)CC2] | 507 |
| 34 | 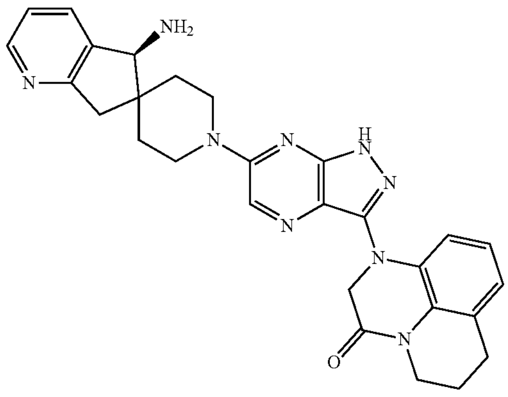 [SMILES: N[C@@H]1c2cccnc2CC12CCN(c1cnc3c(N4CC(=O)N5CCCc6cccc4c65)n[nH]c3n1)CC2] | 508 |
| 35 | 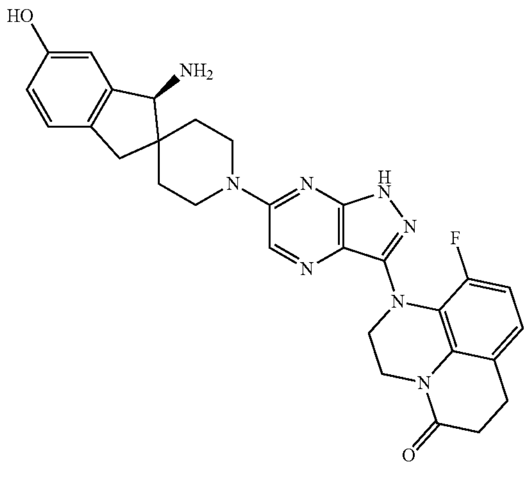 [SMILES: N[C@@H]1c2cc(O)ccc2CC12CCN(c1cnc3c(N4CCN5C(=O)CCc6ccc(F)c4c65)n[nH]c3n1)CC2] | 541 |

TABLE 3-continued
| Compound | Compound structure | MS (M + H)⁺ |
| --- | --- | --- |
| 36 | 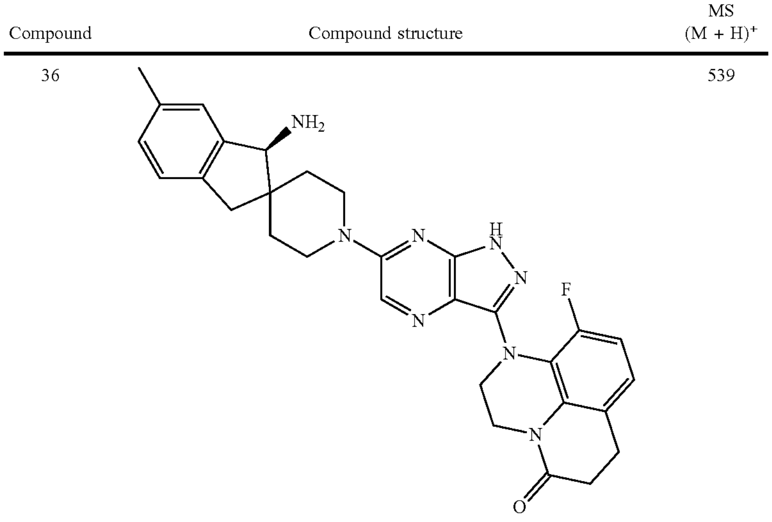 | 539 |
| 37 | 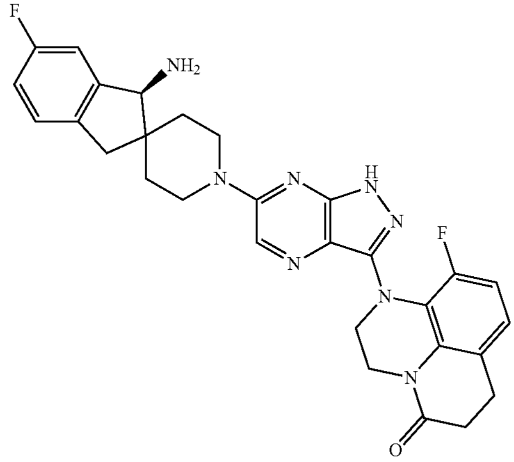 [SMILES: N[C@@H]1c2cc(F)ccc2CC12CCN(c1cnc3c(N4CCN5C(=O)CCc6ccc(F)c4c65)n[nH]c3n1)CC2] | 543 |
| 38 | 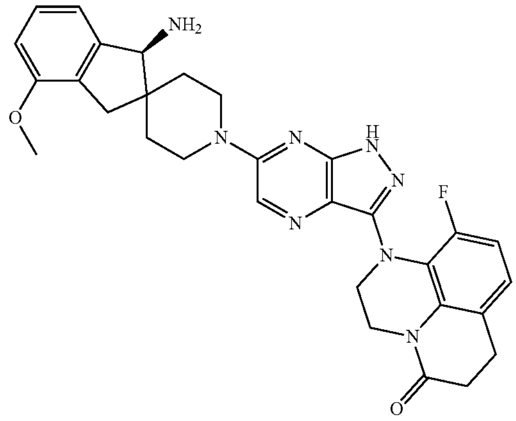 [SMILES: COc1cccc2c1CC1(CCN(c3cnc4c(N5CCN6C(=O)CCc7ccc(F)c5c76)n[nH]c4n3)CC1)[C@@H]2N] | 555 |

TABLE 3-continued
| Compound | Compound structure | MS (M + H)+ |
|---|---|---|
| 39 | 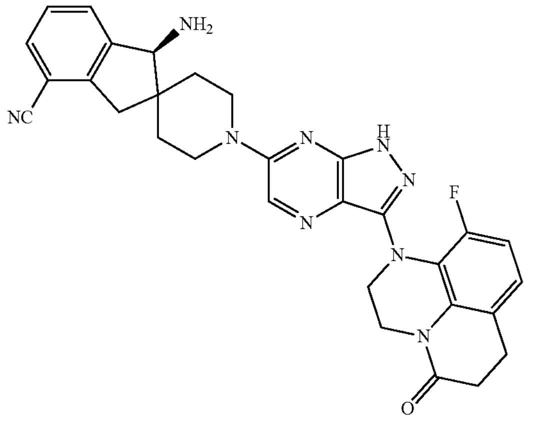 [SMILES: N#Cc1cccc2c1CC1(CCN(c3cnc4c(N5CCN6C(=O)CCc7ccc(F)c5c76)n[nH]c4n3)CC1)[C@@H]2N] | 550 |
| 40 | 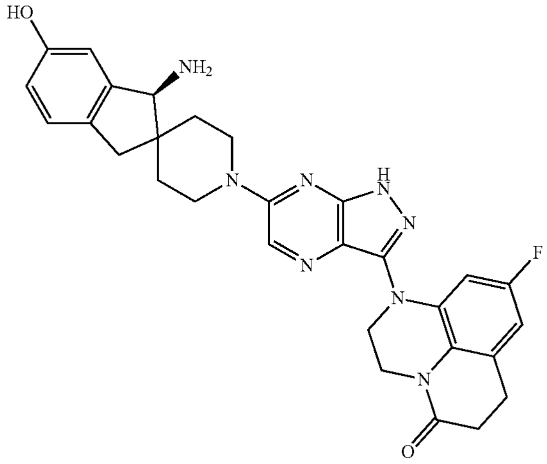 [SMILES: N[C@@H]1c2cc(O)ccc2CC12CCN(c1cnc3c(N4CCN5C(=O)CCc6cc(F)cc4c65)n[nH]c3n1)CC2] | 541 |
| 41 | 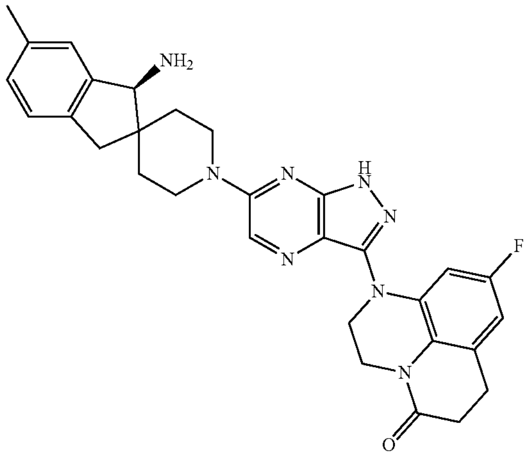 [SMILES: Cc1ccc2c(c1)[C@@H](N)C1(CCN(c3cnc4c(N5CCN6C(=O)CCc7cc(F)cc5c76)n[nH]c4n3)CC1)C2] | 539 |

TABLE 3-continued
| Compound | Compound structure | MS (M + H)+ |
| --- | --- | --- |
| 42 | 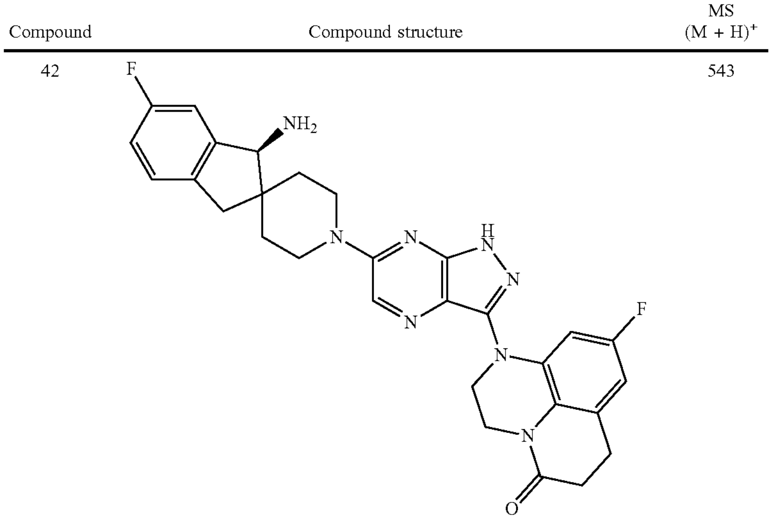 | 543 |
| 43 | 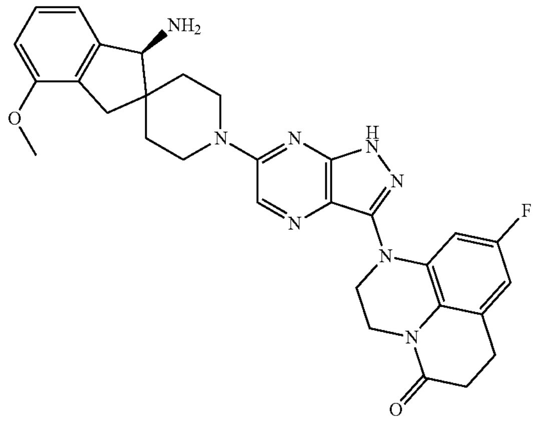 [SMILES: COc1cccc2c1CC1(CCN(c3cnc4c(N5CCN6C(=O)CCc7cc(F)cc5c76)n[nH]c4n3)CC1)[C@@H]2N] | 555 |
| 44 | 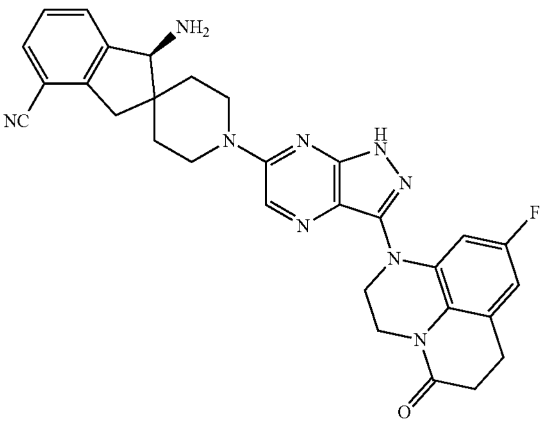 [SMILES: N#Cc1cccc2c1CC1(CCN(c3cnc4c(N5CCN6C(=O)CCc7cc(F)cc5c76)n[nH]c4n3)CC1)[C@@H]2N] | 550 |

TABLE 3-continued
| Compound | Compound structure | MS (M + H)$^+$ |
| --- | --- | --- |
| 45 | 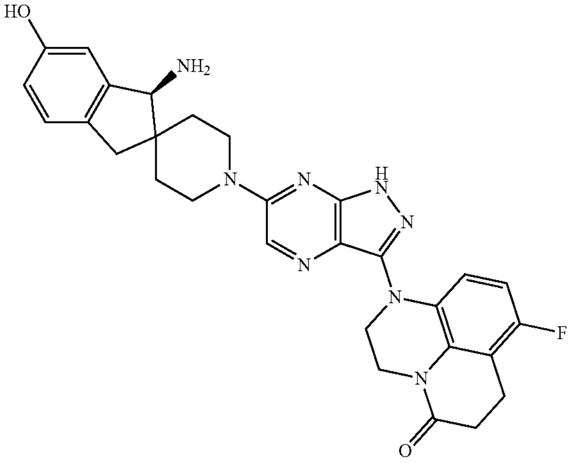 [SMILES: N[C@@H]1c2cc(O)ccc2CC12CCN(c1cnc3c(N4CCN5C(=O)CCc6c(F)ccc4c65)n[nH]c3n1)CC2] | 541 |
| 46 | 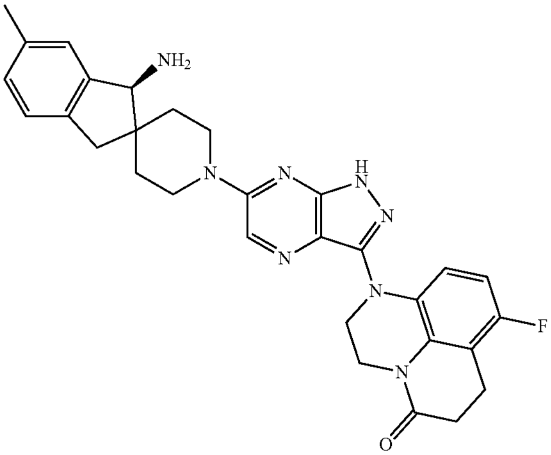 [SMILES: Cc1ccc2c(c1)[C@@H](N)C1(CCN(c3cnc4c(N5CCN6C(=O)CCc7c(F)ccc5c76)n[nH]c4n3)CC1)C2] | 539 |
| 47 | 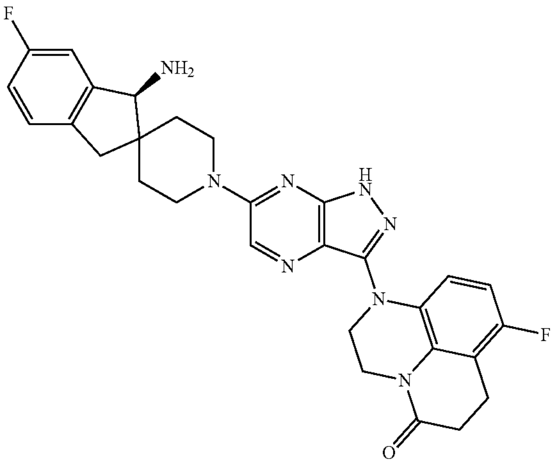 [SMILES: N[C@@H]1c2cc(F)ccc2CC12CCN(c1cnc3c(N4CCN5C(=O)CCc6c(F)ccc4c65)n[nH]c3n1)CC2] | 543 |

TABLE 3-continued

| Compound | Compound structure | MS (M + H)+ |
|---|---|---|
| 48 | 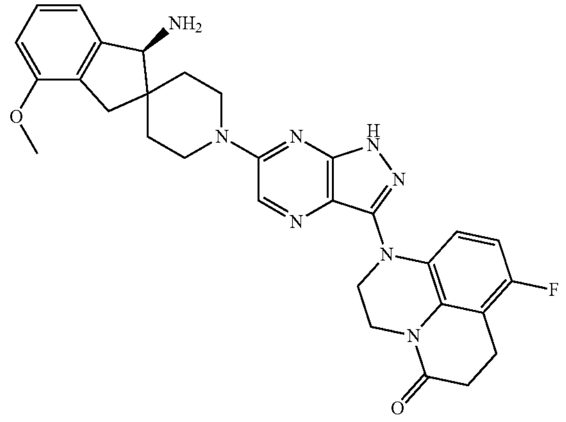 [SMILES: COc1cccc2c1CC1(CCN(c3cnc4c(N5CCN6C(=O)CCc7c(F)ccc5c76)n[nH]c4n3)CC1)[C@@H]2N] | 555 |
| 49 | 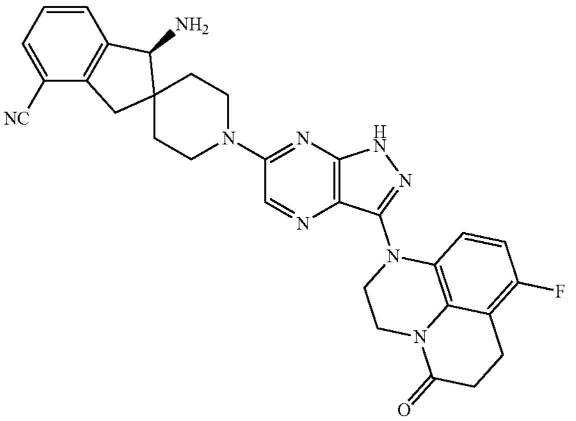 [SMILES: N#Cc1cccc2c1CC1(CCN(c3cnc4c(N5CCN6C(=O)CCc7c(F)ccc5c76)n[nH]c4n3)CC1)[C@@H]2N] | 550 |

Example 50. In Vitro Anti-Proliferative Activity of Compounds of the Present Invention Against MIA PaCa-2 Cells MIA PaCa-2 cells were seeded on a 96-well plate at 3000 cells/well. After overnight adherence culture, DMSO or the compounds serially diluted 1:5 from 5 M were added. The viability was assessed 72 h after dosing by measuring the intracellular ATP content. The inhibition percentages of viable cells by the compounds were calculated by comparing with the DMSO group, and the $IC_{50}$ values were calculated. The results are shown in Table 4 below.

TABLE 4

In vitro anti-proliferative activity of compounds of the present invention against MIA PaCa-2 cells ($IC_{50}$, nM)

| Compound | $IC_{50}$ | Compound | $IC_{50}$ | Compound | $IC_{50}$ | Compound | $IC_{50}$ |
|---|---|---|---|---|---|---|---|
| 1 | 35.1 | 3 | 5.1 | 6 | 6.5 | 9 | 8.9 |
| 10 | 12.1 | 12 | 5.8 | 14 | 7.2 | 16 | 9.3 |
| 17 | 10.8 | 21 | 11.3 | 24 | 9.6 | 26 | 8.1 |
| 27 | 15.9 | 35 | 17.3 | 36 | 12.5 | 37 | 13.9 |
| 38 | 15.6 | 40 | 18.1 | 41 | 13.5 | 42 | 10.1 |
| 45 | 11.5 | 46 | 14.0 | 47 | 9.5 | 48 | 19.2 |

As can be seen from the data in Table 4, the compounds of the present invention have unexpectedly strong in vitro anti-proliferative activity against MIA PaCa-2 cells.

Although specific embodiments of the present invention have been described above, it will be appreciated by those skilled in the art that these embodiments are merely illustrative and that many changes or modifications can be made to these embodiments without departing from the principles and spirit of the present invention. The protection scope of the present invention is therefore defined by the appended claims.

The invention claimed is:

1. A compound of general formula (1) or an isomer, a crystalline form, a pharmaceutically acceptable salt, a hydrate or a solvate thereof:

(1)

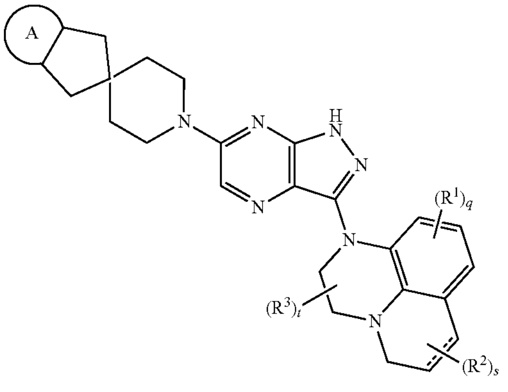

wherein in general formula (1):

each $R^1$ is independently —H, halogen, —OH, —$OR^4$, —$NR^4R^5$, —CN, —$S(O)_pR^4$, (C1-C3) alkyl, (C1-C3) haloalkyl, (C2-C4) alkenyl, (C2-C4) alkynyl or (C3-C5) cycloalkyl, wherein the (C1-C3) alkyl, (C1-C3) haloalkyl, (C2-C4) alkenyl, (C2-C4) alkynyl or (C3-C5) cycloalkyl is each independently and optionally substituted with 1, 2, 3 or 4 of the following groups: —H, halogen, —OH, —$OCH_3$ and —CN;

each $R^2$ is independently —H, halogen, —OH, —$OR^4$, —$NR^4R^5$, —CN, —$S(O)_pR^4$ or (C1-C3) alkyl, wherein the (C1-C3) alkyl is independently and optionally substituted with 1, 2, 3 or 4 of the following groups: —H, halogen, —OH, —$OCH_3$ and —CN; or two $R^2$ linked to the same carbon atom form one oxo;

each $R^3$ is independently —H, halogen, —OH, —$OR^4$, —$NR^4R^5$, —CN, —$S(O)_pR^4$ or (C1-C3) alkyl, wherein the (C1-C3) alkyl is independently and optionally substituted with 1, 2, 3 or 4 of the following groups: —H, halogen, —OH, —$OCH_3$ and —CN; or two $R^3$ linked to the same carbon atom form one oxo;

ring A is phenyl or (5-6 membered) heteroaryl, wherein the phenyl or (5-6 membered) heteroaryl is each independently and optionally substituted with 1, 2, 3 or 4 of the following groups: —H, halogen, —OH, —$OR^4$, —$NR^4R^5$, —CN, —$S(O)_pR^4$, (C1-C3) alkyl, (C1-C3) haloalkyl, (C2-C4) alkenyl, (C2-C4) alkynyl or (C3-C5) cycloalkyl, wherein the (C1-C3) alkyl, (C1-C3) haloalkyl, (C2-C4) alkenyl, (C2-C4) alkynyl or (C3-C5) cycloalkyl is each independently and optionally substituted with 1, 2, 3 or 4 of the following groups: —H, halogen, —OH, —$OCH_3$ and —CN;

$R^4$ and $R^5$ are each independently —H, (C1-C3) alkyl, (C1-C3) haloalkyl or (C3-C5) cycloalkyl, or $R^4$ and $R^5$ on the same nitrogen atom, together with the N atom to which they are linked, form (3-6 membered) heterocycloalkyl, wherein the (3-6 membered) heterocycloalkyl is optionally substituted with 1, 2, 3 or 4 of the following groups: —H, halogen, $R^6$ and —$OR^6$;

$R^6$ is —H, (C1-C3) alkyl or (C3-C5) cycloalkyl; and p is an integer of 0, 1 or 2, q is an integer of 0, 1, 2 or 3, s is an integer of 0, 1, 2, 3 or 4, and t is an integer of 0, 1, 2, 3 or 4.

2. The compound or the isomer, the crystalline form, the pharmaceutically acceptable salt, the hydrate or the solvate thereof according to claim 1, wherein in general formula (1), each $R^1$ is independently —H, halogen, —OH, —$OR^4$, —$NR^4R^5$, —CN, —$S(O)_pR^4$, (C1-C3) alkyl, (C1-C3) haloalkyl, (C2-C4) alkenyl, (C2-C4) alkynyl or (C3-C5) cycloalkyl, wherein the (C1-C3) alkyl, (C1-C3) haloalkyl, (C2-C4) alkenyl, (C2-C4) alkynyl or (C3-C5) cycloalkyl is each independently and optionally substituted with 1, 2, 3 or 4 of the following groups: —H, —F, —OH, —$OCH_3$ and —CN.

3. The compound or the isomer, the crystalline form, the pharmaceutically acceptable salt, the hydrate or the solvate thereof according to claim 2, wherein in general formula (1), each $R^1$ is independently —H, —F, —OH, —$OCH_3$, —$N(CH_3)_2$, —CN, —$S(O)_2CH_3$,

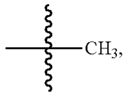 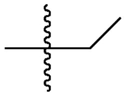, 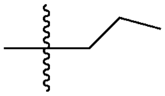,

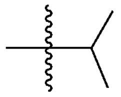, 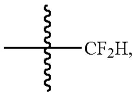 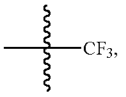

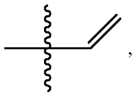, 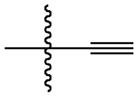, 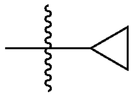,

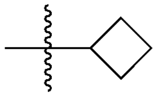 or 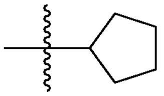;

preferably, q is 1, and $R^1$ is independently —H or —F.

4. The compound or the isomer, the crystalline form, the pharmaceutically acceptable salt, the hydrate or the solvate thereof according to claim 1, wherein in general formula (1), each $R^2$ is independently —H, halogen, —OH, —$OR^4$, —$NR^4R^5$, —CN, —$S(O)_pR^4$ or (C1-C3) alkyl, wherein the (C1-C3) alkyl is independently and optionally substituted with 1, 2, 3 or 4 of the following groups: —H, —F, —OH, —$OCH_3$ and —CN; or two $R^2$ linked to the same carbon atom form one oxo.

5. The compound or the isomer, the crystalline form, the pharmaceutically acceptable salt, the hydrate or the solvate thereof according to claim 4, wherein in general formula (1), each $R^2$ is independently: —H, —F, —OH, —$OCH_3$, —$N(CH_3)_2$, —CN, —$S(O)_2CH_3$,

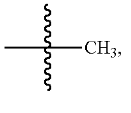 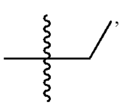, 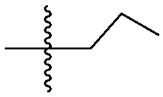 or

-continued

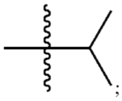

;

preferably, s is 2, and both $R^2$ are —H, or two $R^2$ linked to the same carbon atom form one oxo.

6. The compound or the isomer, the crystalline form, the pharmaceutically acceptable salt, the hydrate or the solvate thereof according to claim 1, wherein in general formula (1), each $R^3$ is independently —H, halogen, —OH, —$OR^4$, —$NR^4R^5$, —CN, —$S(O)_pR^4$ or (C1-C3) alkyl, wherein the (C1-C3) alkyl is independently and optionally substituted with 1, 2, 3 or 4 of the following groups: —H, —F, —OH, —$OCH_3$ and —CN; or two $R^3$ linked to the same carbon atom form one oxo.

7. The compound or the isomer, the crystalline form, the pharmaceutically acceptable salt, the hydrate or the solvate thereof according to claim 6, wherein in general formula (1), each $R^3$ is independently: —H, —F, —OH, —$OCH_3$, —$N(CH_3)_2$, —CN, —$S(O)_2CH_3$,

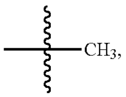

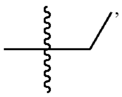

,

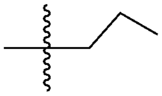

or

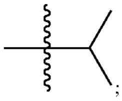

;

preferably, t is 1, and $R^3$ is —H; or tis 2, and two $R^3$ linked to the same carbon atom form one oxo.

8. The compound or the isomer, the crystalline form, the pharmaceutically acceptable salt, the hydrate or the solvate thereof according to claim 1, wherein in general formula (1), structural unit

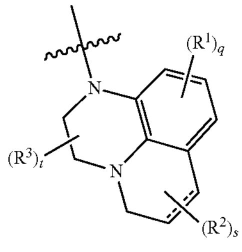

is:

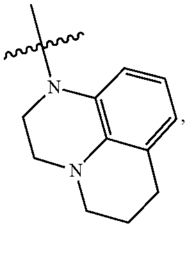

,

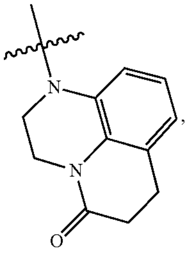

,

-continued

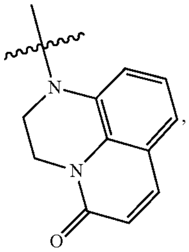

,

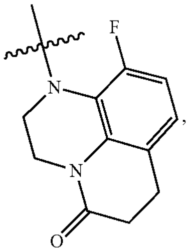

,

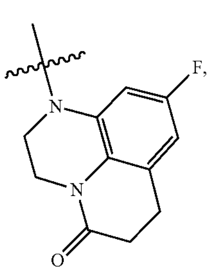

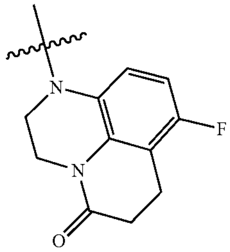

or

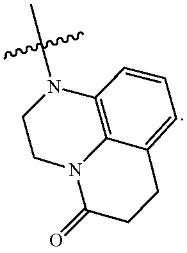

.

9. The compound or the isomer, the crystalline form, the pharmaceutically acceptable salt, the hydrate or the solvate thereof according to claim 1, wherein in general formula (1), ring A is phenyl or (5-6 membered) heteroaryl, wherein the phenyl or (5-6 membered) heteroaryl is each independently and optionally substituted with 1, 2, 3 or 4 of the following groups: —H, —F, —Cl, —OH, —$OCH_3$, —$N(CH_3)_2$, —CN, —$S(O)_2CH_3$,

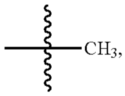

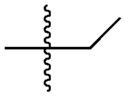

,

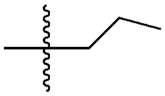

,

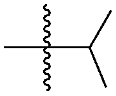

,

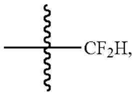

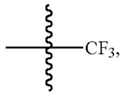

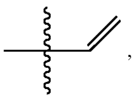

,

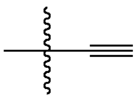

,

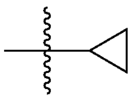

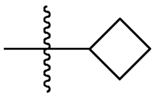

or

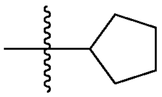

.

10. The compound or the isomer, the crystalline form, the pharmaceutically acceptable salt, the hydrate or the solvate thereof according to claim 1, wherein in general formula (1), structural unit

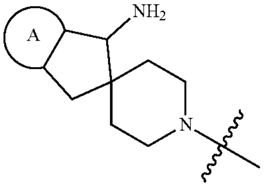
is:
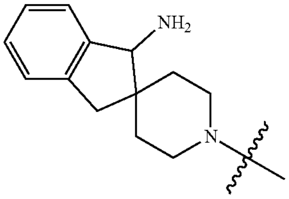
,
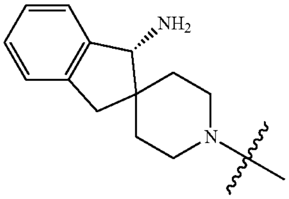
,
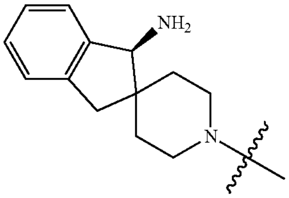
,
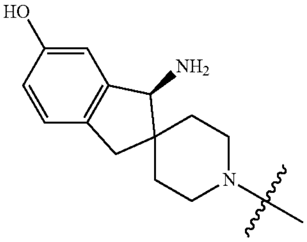
,
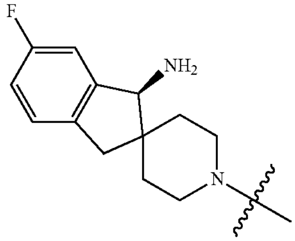
,
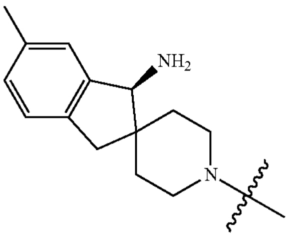
,
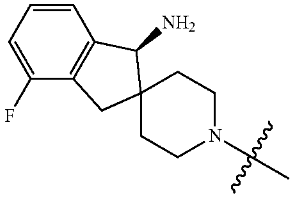
,
-continued
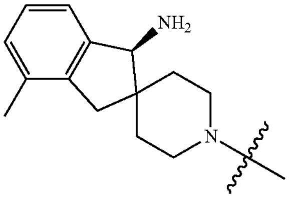
,
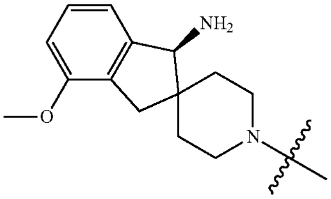
,
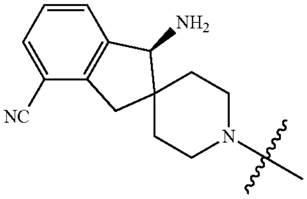
,
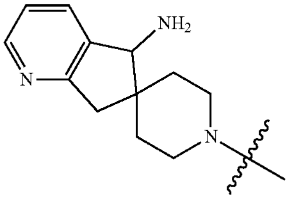
,
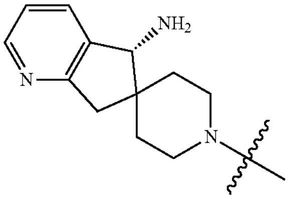
,
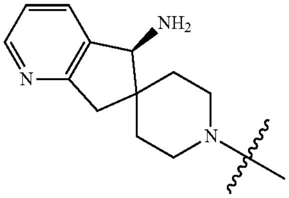
,
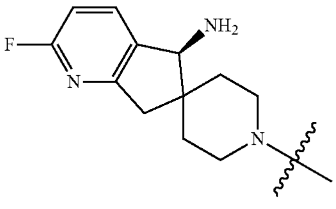
,
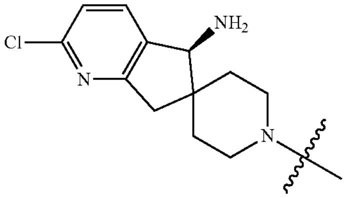

-continued
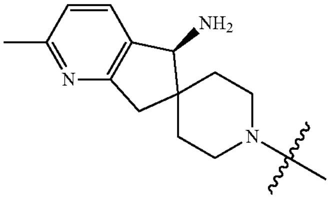
,
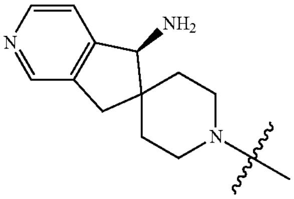
,
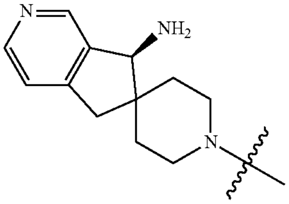
,
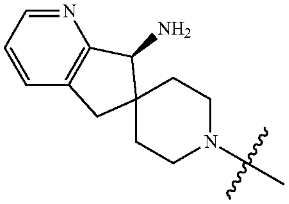
,
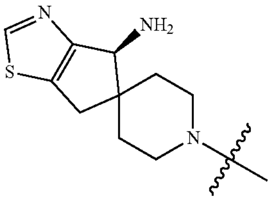
,
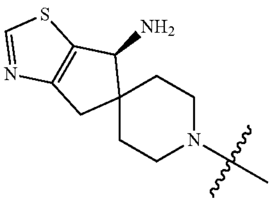
,
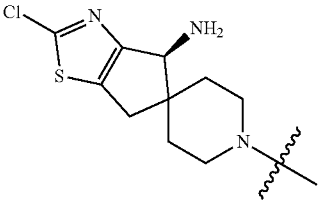
,
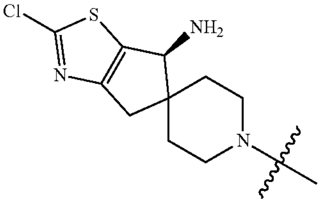
,
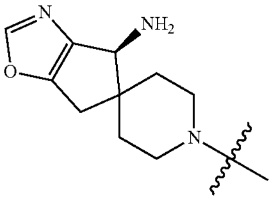
or
-continued
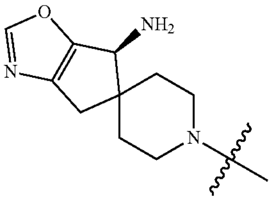
.
11. The compound or the isomer, the crystalline form, the pharmaceutically acceptable salt, the hydrate or the solvate thereof according to claim 1, wherein in general formula (1), the compound has one of the following structures:
1
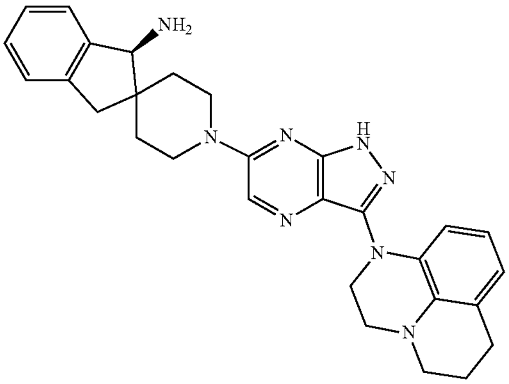
2
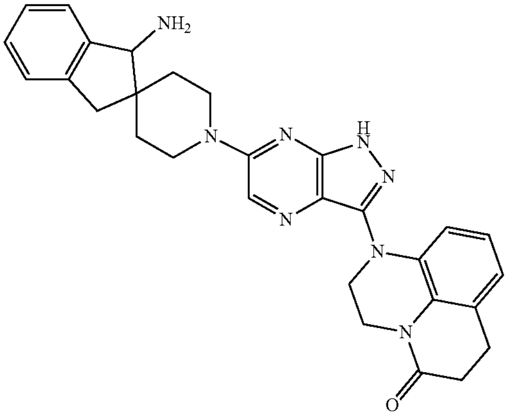
3
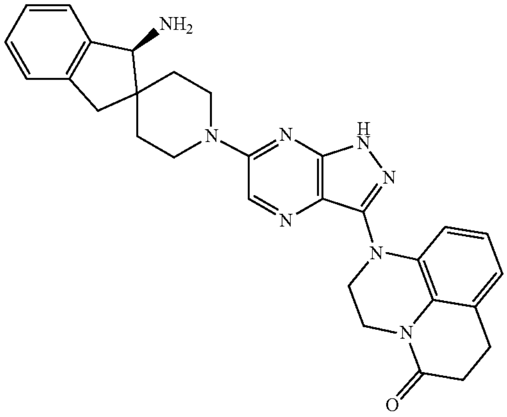

4
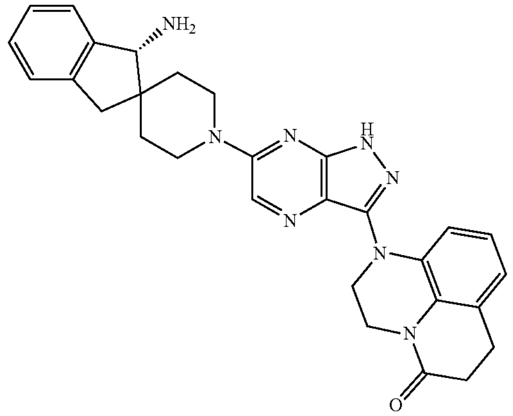
5
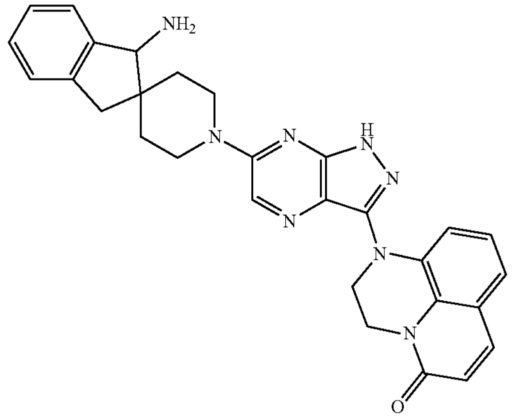
6
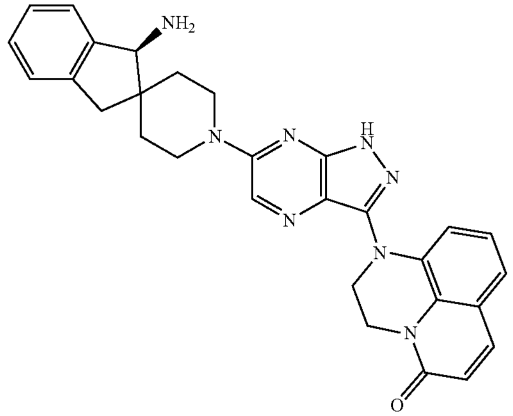
7
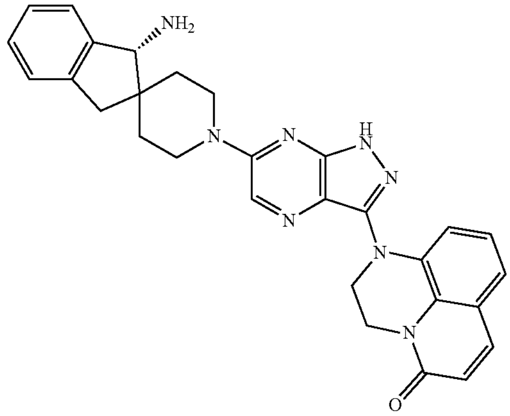
8
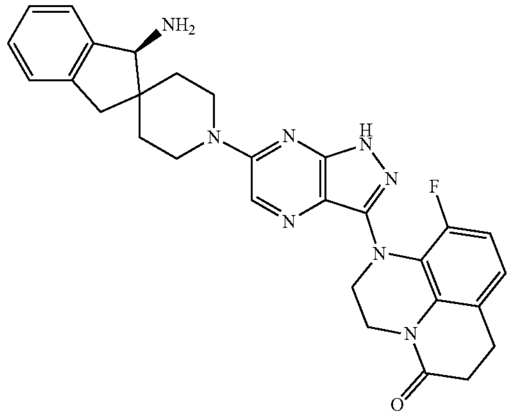
9
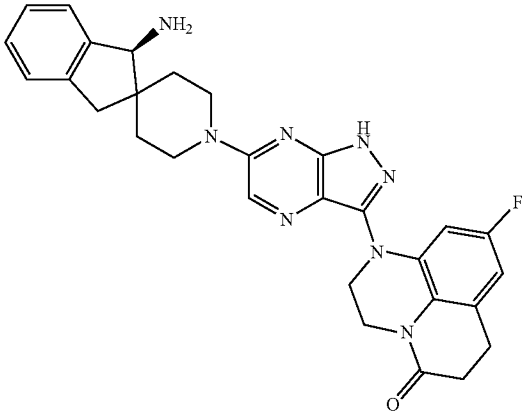

-continued
10
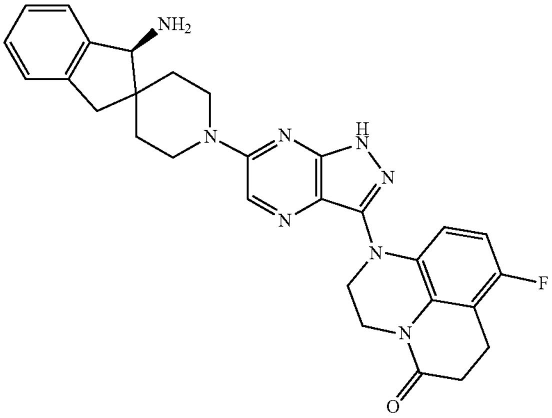
11
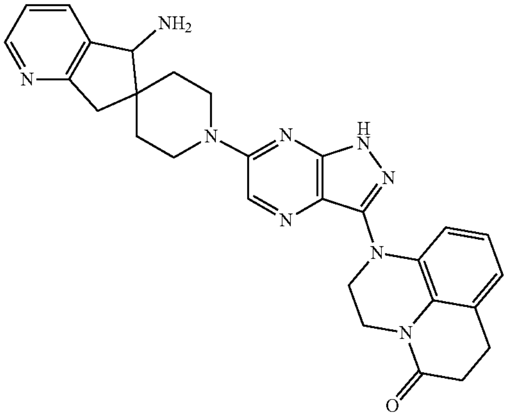
12
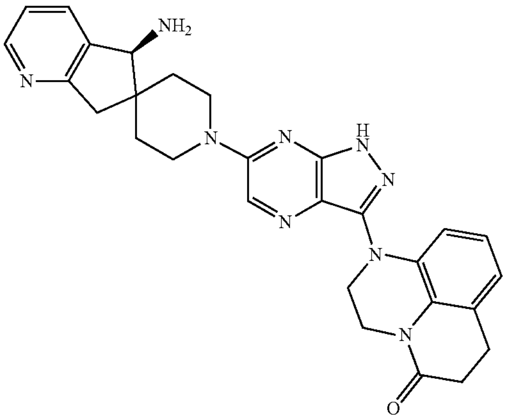
-continued
13
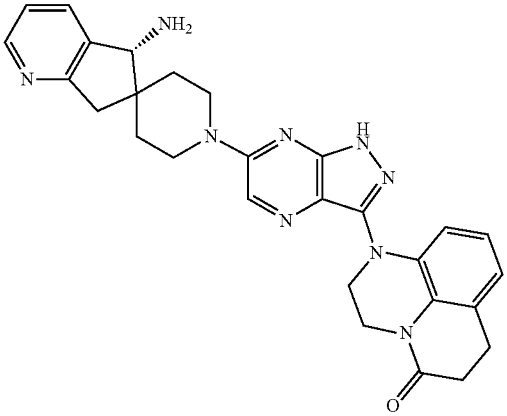
14
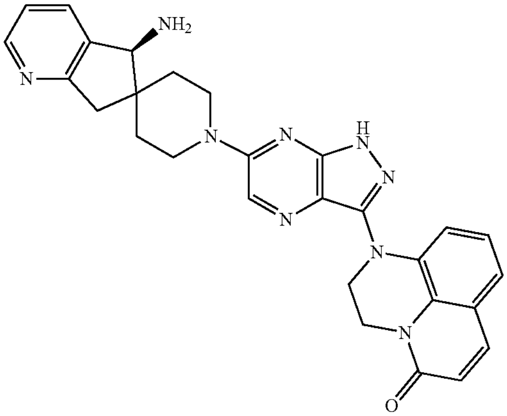
15
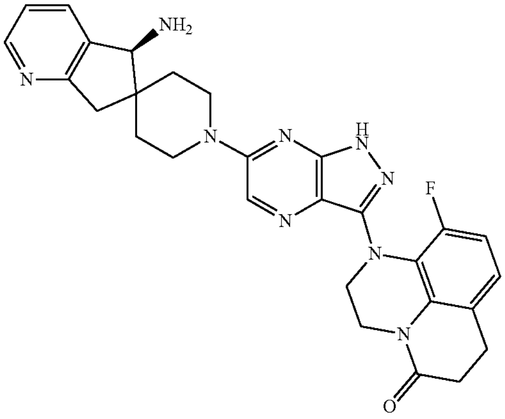

-continued
16
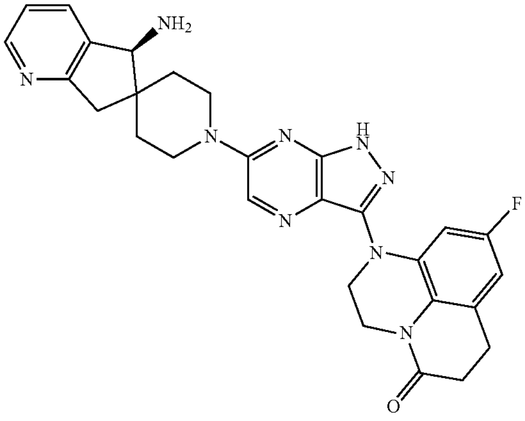
17
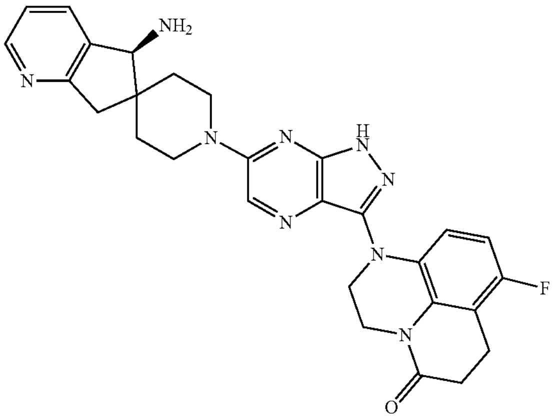
18
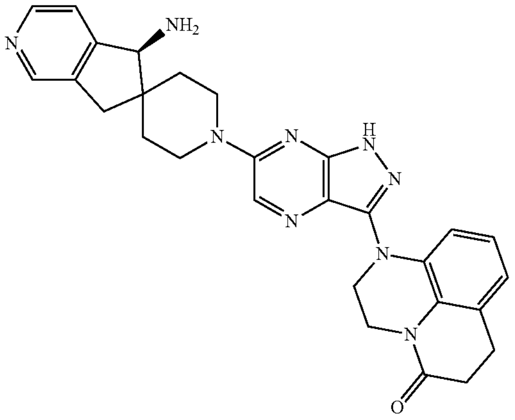
-continued
19
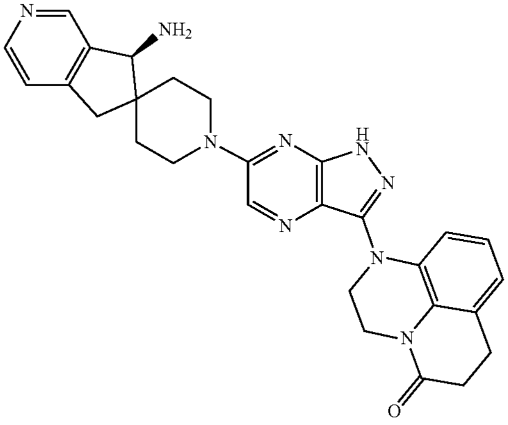
20
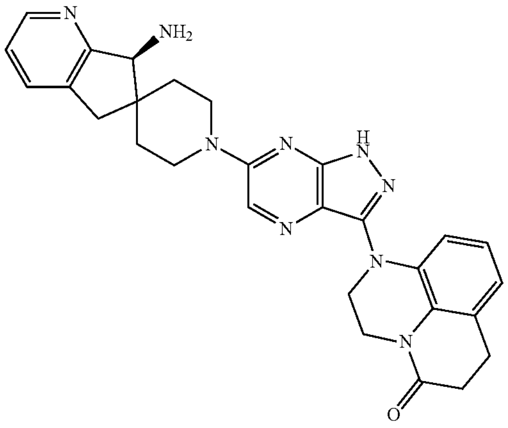
21
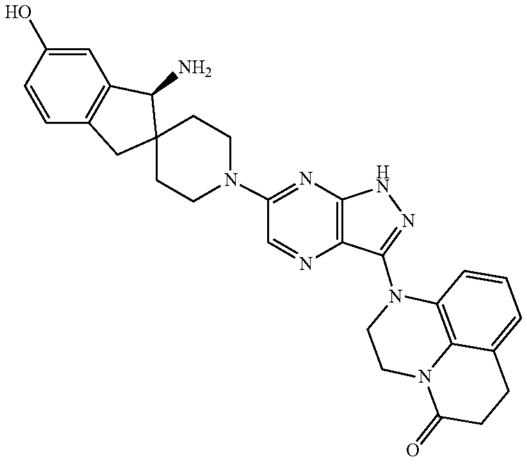

-continued
22
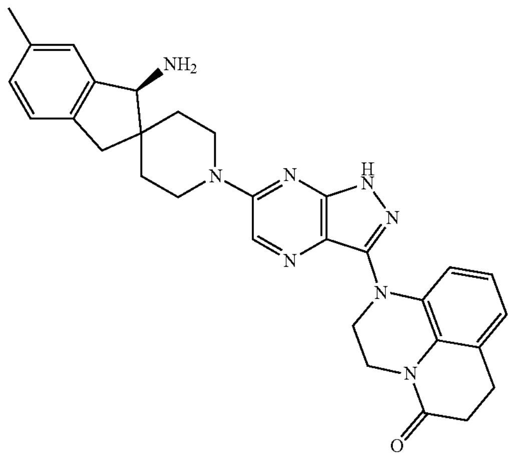
23
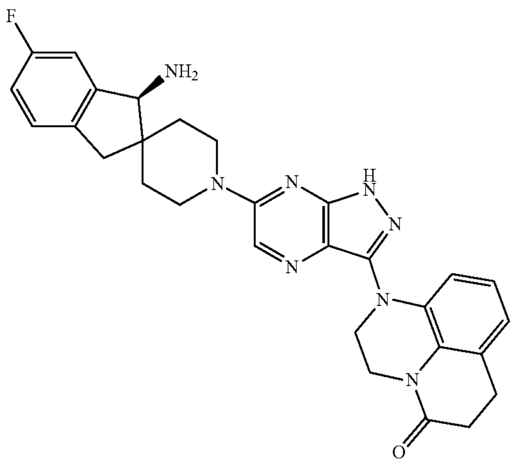
24
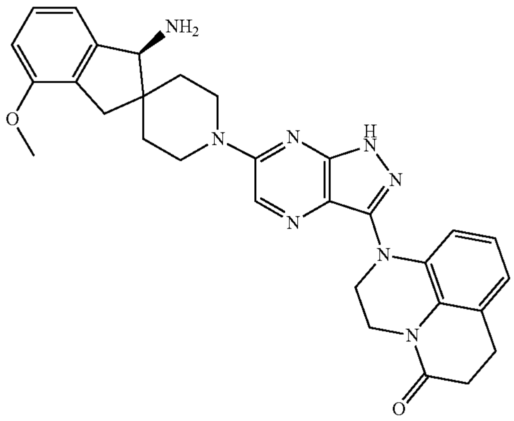
-continued
25
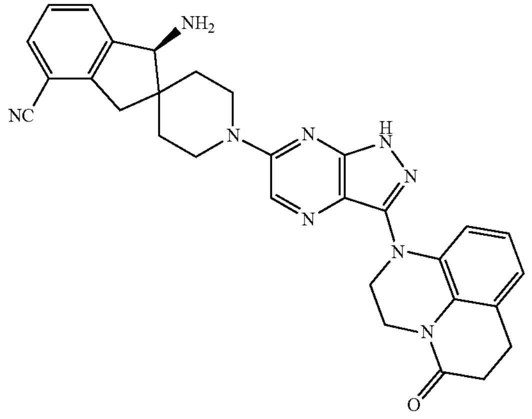
26
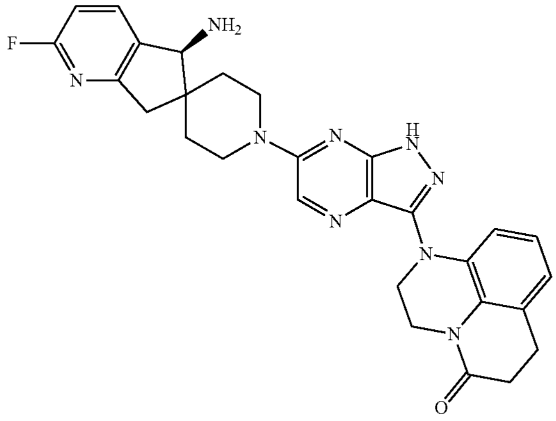
27
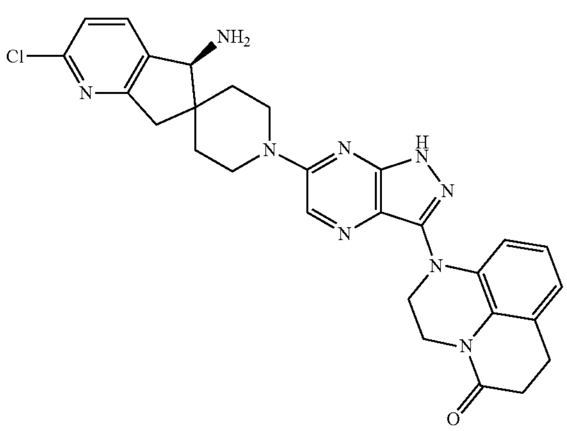

-continued
28
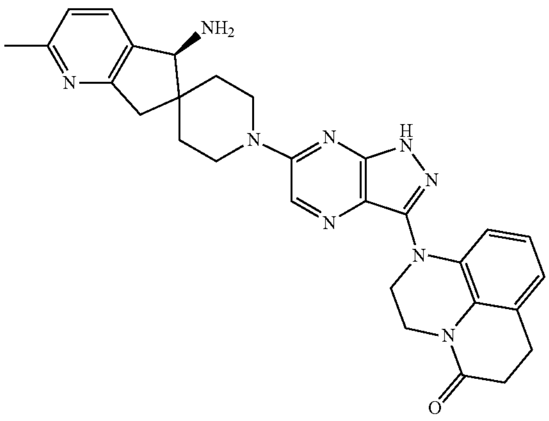
29
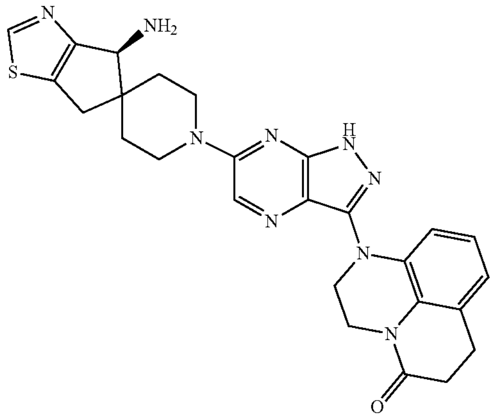
30
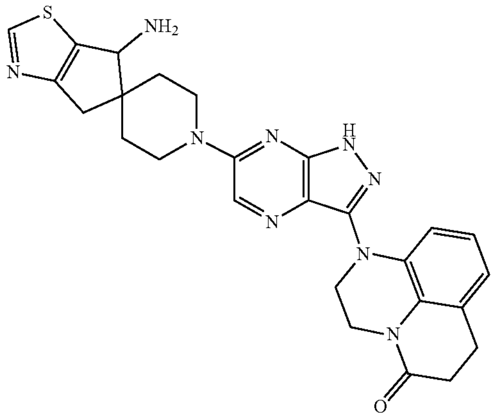
-continued
31
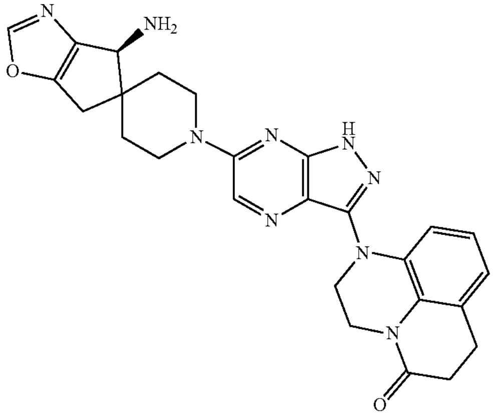
32
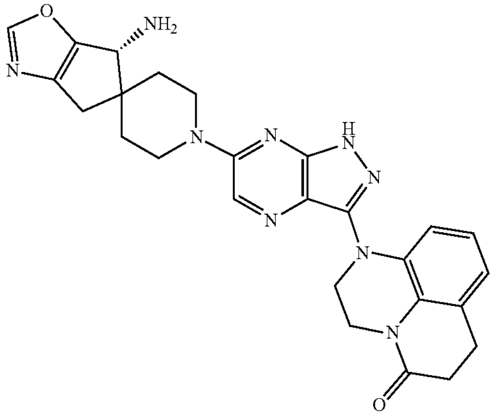
33
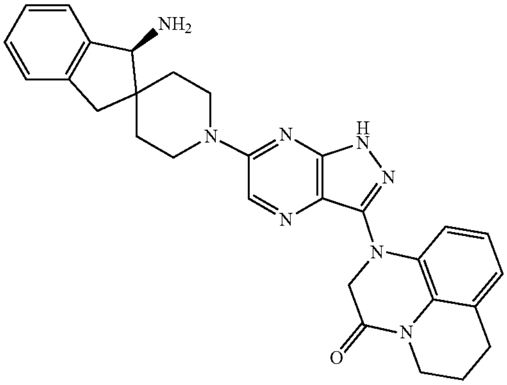
34
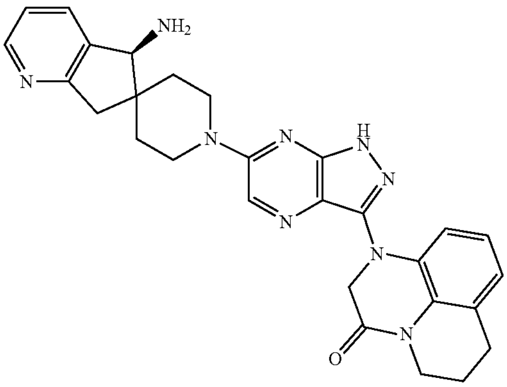

-continued
35
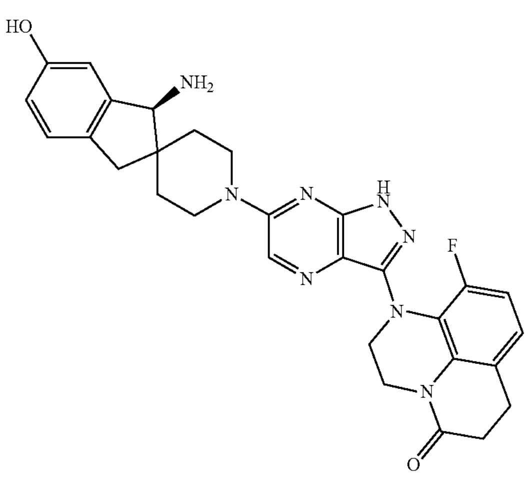
36
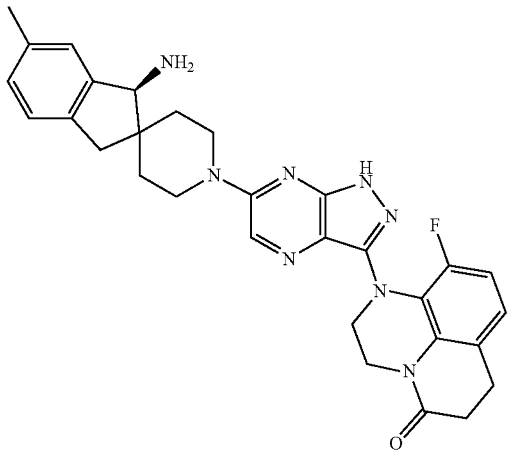
37
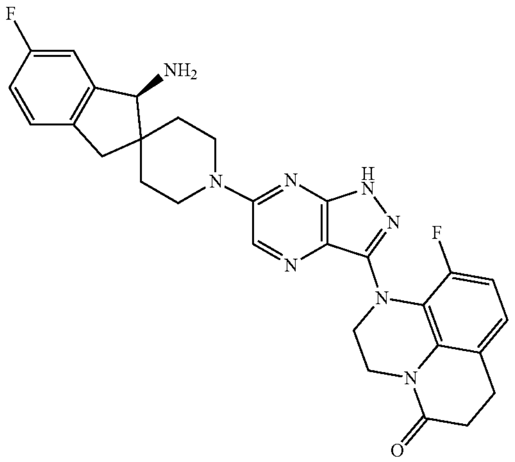
-continued
38
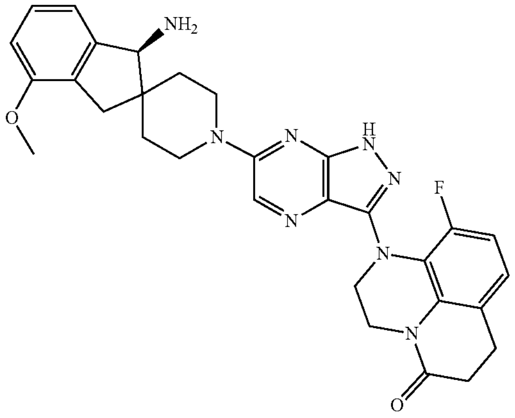
39
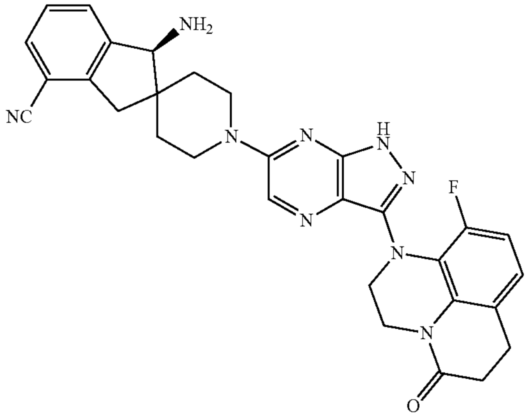
40
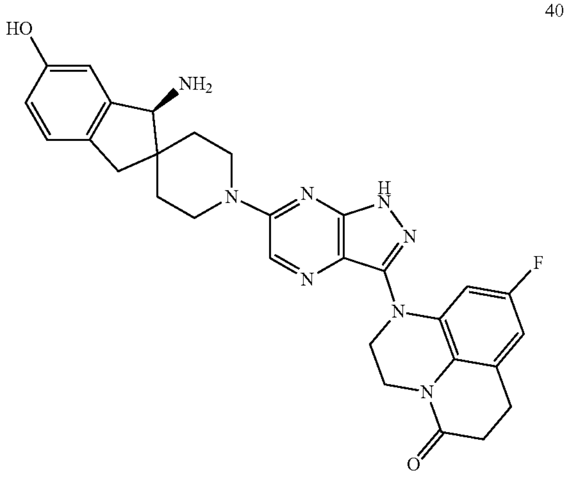

-continued
41
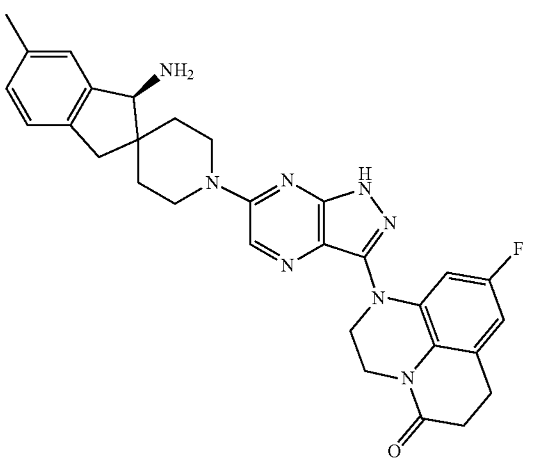
42
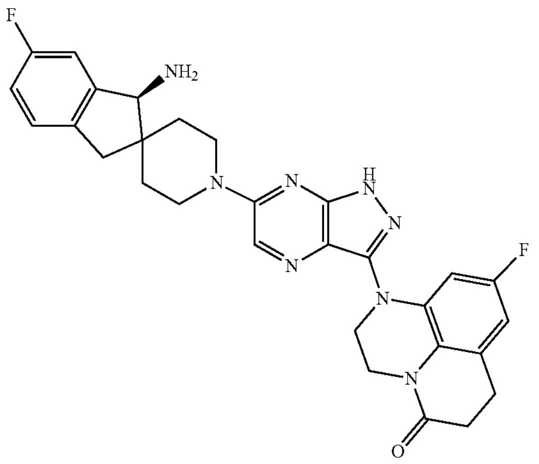
43
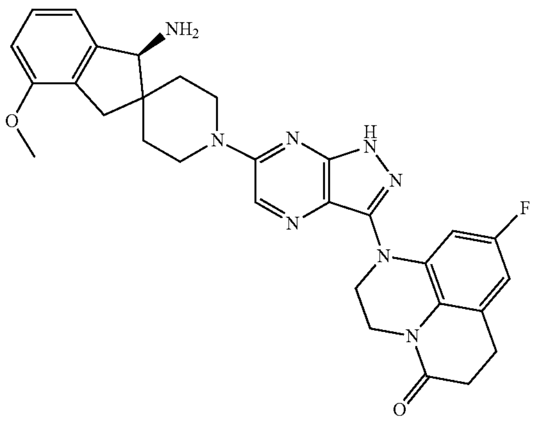
-continued
44
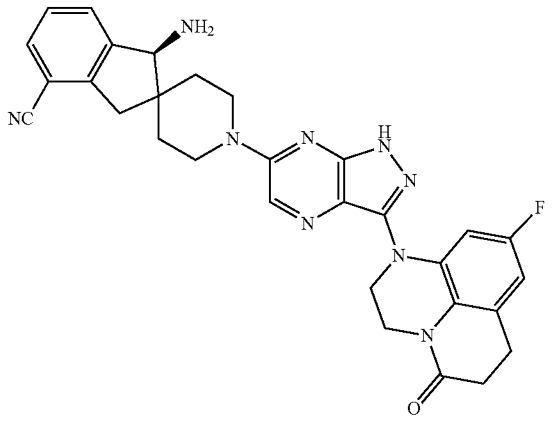
45
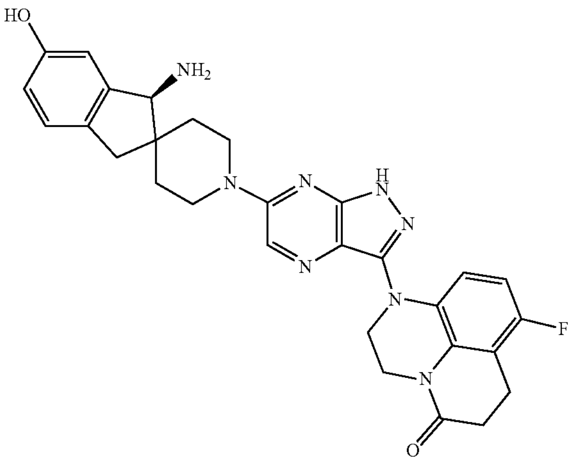
46
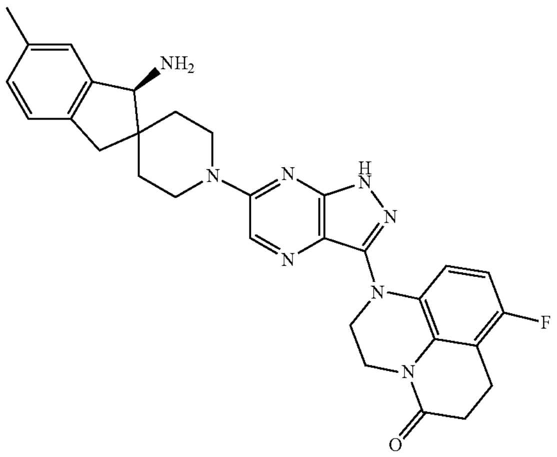

-continued
47
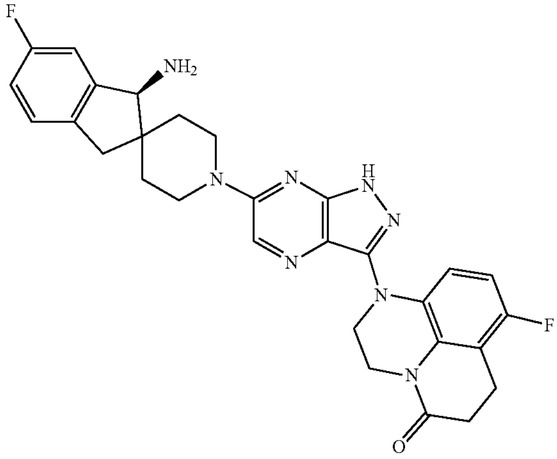
48
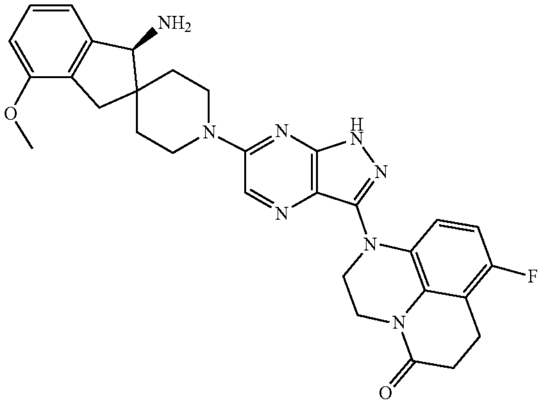
or
-continued
49
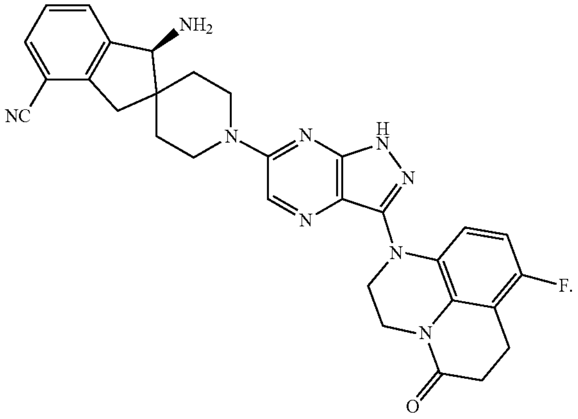
12. A pharmaceutical composition, comprising a pharmaceutically acceptable excipient or carrier; and the compound or the isomer, the crystalline form, the pharmaceutically acceptable salt, the hydrate or the solvate thereof according to claim 1 as an active ingredient.
* * * * *